(12) United States Patent
Culbertson et al.

(10) Patent No.: US 8,268,948 B2
(45) Date of Patent: Sep. 18, 2012

(54) POLYMERIC REAGENTS COMPRISING A TERMINAL VINYLIC GROUP AND CONJUGATES FORMED THEREFROM

(75) Inventors: Sean M. Culbertson, Gurley, AL (US); Samuel P. McManus, Huntsville, AL (US)

(73) Assignee: Nektar Therapeutics, San Francisco, CA (US)

(*) Notice: Subject to any disclaimer, the term of this patent is extended or adjusted under 35 U.S.C. 154(b) by 296 days.

(21) Appl. No.: 12/374,297

(22) PCT Filed: Jul. 20, 2007

(86) PCT No.: PCT/US2007/016486
§ 371 (c)(1),
(2), (4) Date: Oct. 16, 2009

(87) PCT Pub. No.: WO2008/011165
PCT Pub. Date: Jan. 24, 2008

(65) Prior Publication Data
US 2010/0048707 A1    Feb. 25, 2010

Related U.S. Application Data

(60) Provisional application No. 60/832,411, filed on Jul. 21, 2006.

(51) Int. Cl.
*A61K 8/42* (2006.01)
*C08F 32/08* (2006.01)
*A61P 43/00* (2006.01)
(52) U.S. Cl. .......................... 526/280; 514/562; 514/1.1
(58) Field of Classification Search .................. None
See application file for complete search history.

(56) References Cited

U.S. PATENT DOCUMENTS

| | | | |
|---|---|---|---|
| 4,424,311 | A | 1/1984 | Nagaoka et al. |
| 4,510,233 | A | 4/1985 | Yokoyama et al. |
| 5,629,384 | A | 5/1997 | Veronese et al. |
| 5,932,462 | A | 8/1999 | Harris et al. |
| 6,362,254 | B2 | 3/2002 | Harris et al. |
| 6,362,276 | B1 | 3/2002 | Harris et al. |
| 6,514,491 | B1 | 2/2003 | Bentley et al. |
| 2003/0031647 | A1 | 2/2003 | Zahm |
| 2004/0086991 | A1 | 5/2004 | Harris et al. |
| 2005/0079155 | A1 | 4/2005 | Marshall |
| 2006/0171920 | A1 | 8/2006 | Shechter et al. |
| 2006/0293499 | A1* | 12/2006 | Bentley et al. .............. 528/322 |
| 2007/0027073 | A1 | 2/2007 | Rubinstein et al. |

FOREIGN PATENT DOCUMENTS

| | | |
|---|---|---|
| EP | 1249846 | 10/2002 |
| GB | 2407501 | 5/2005 |
| JP | 2004126136 | * 4/2004 |
| WO | 2004089280 | 10/2004 |
| WO | 2005014049 | 2/2005 |
| WO | 2005073258 | 8/2005 |
| WO | WO 2006/138572 | 12/2006 |

OTHER PUBLICATIONS

Reutenauer et al. in Macromolecules (2001), 34(4), 755-760.*
Definition of Purify in http://www.thefreedictionary.com/purify).*
Bishop et al. in Science Separation and Technology (1988), 23(4-5), 507-511.*
European Extended Search Report corresponding to European Patent Application No. 07836169.8 date Aug. 4, 2010.
Bodanszky, et al., "Derivatives of S-9-fluorenylmethyl-L-Cysteine", Int. J. Peptide Protein Res., vol. 20, pp. 434-437, (1982).
Bordwell, et al., "Steric Inhibition of Synergistic Radical Stabilizing Effects", J. Org. Chem., vol. 55, pp. 58-63, (1990).
Eisenbeis et al. "A Practical Large Scale Synthesis of 9-(Hydroxymethyl)-Fluorene-4-Carboxylic Acid (HOFmCO2H)", Synthetic Communications, vol. 31, No. 22, pp. 3533-3536, (2001).
Gershonov, et al., "A Novel Approach for a Water-Soluble Long-Acting Insulin Prodrug: Design, Preparation, and Analysis of [(2-Sulfo)-9-fluorenylmethoxycarbonyl Derivatives of Insulin", J. Med. Chem., vol. 43, pp. 2530-2537, (2000).
Gershonov, et al., "New Concept for Long-Acting Insulin; Spontaneous Conversion of an Inactive Modified Insulin to the Active Hormone in Circulation: 9-Fluorenylmethoxycarbonyl Derivatives of Insulin", Diabetes, vol. 48, pp. 1437-1442, (Jul. 1999).
Greenwald, et al., "Drug delivery systems: anticancer prodrugs and their polymeric conjugates", Exp. Opin. Ther. Patents, vol. 7, No. 6, pp. 601-609, (1997).
Harris, et al., "Effect of Pegylation on Pharmaceuticals", Nature Reviews/Drug Discovery, vol. 2, pp. 214-221, (Mar. 2003).
Liu, et al., "A novel Fmoc-based anchorage for the synthesis of protected peptides on solid phase", Int. J. Peptide Protein Res., vol. 35, pp. 95-98, (1990).
Lottner, et al., "Hematoporphyrin-derived soluble porphyrin-platinum conjugates with combined cytotoxic and phototoxic antitumor activity", J. of Med. Chem., vol. 45, No. 10, (May 9, 2002).
Ouchi, et al., "Design of Antitumor Agent-Terminated Poly(Ethylene Glycol) Conjugates as Macromolecular Prodrug", Polymer Preprints, vol. 38, No. 1, pp. 582-583, (1997).
Ouchi, et al., "Synthesis and Antitumor Activity of Poly(Ethylene Glycol)s Linked to 5-Fluorouracil via a Urethane or Urea Bond", Drug Design and Discovery, vol. 9, pp. 93-105, (1997).
Peleg-Shulman, et al., "Reversible PEGylation: A Novel Technology to Release Native Interferon alpha2 over a Prolonged Time Period", J. Med. Chem., vol. 47, pp. 4897-4904, (2004).
Shechter, et al., "Prolonging the half-life of human interferon-alpha2 in circulation: Design, preparation, and analysis of (2-sulfo-9-fluorenylmethoxycarbonyl)7-interferon-alpha2", PNAS, vol. 98, No. 3, pp. 1212-1217, (Jan. 30, 2001).
Shechter, et al., "Reversible PEGylation of peptide YY3-36 prolongs its inhibition of food intake in mice", FEBS Letters, vol. 579, pp. 2439-2444, (2005).
Sims, et al., "A Method for the Estimation of Polyethylene Glycol in Plasma Protein Fractions", Analytical Biochemistry, vol. 107, pp. 60-63, (1980).

(Continued)

*Primary Examiner* — Timothy Thomas
*Assistant Examiner* — Dennis Heyer
(74) *Attorney, Agent, or Firm* — Mark A. Wilson

(57) ABSTRACT

The present invention provides conjugates having a degradable linkage and polymeric reagents useful in preparing such conjugates. Methods of making polymeric reagents and conjugates, as well as methods for administering conjugates and compositions, are also provided.

10 Claims, 3 Drawing Sheets

OTHER PUBLICATIONS

Tsubery, et al., "Prolonging the Action of Protein and Peptide Drugs by a Novel Approach of Reversible Polyethylene Glycol Modification", The J. of Bio. Chem., vol. 279, No. 37, Issue of Sep. 10, pp. 38118-38124, (2004).
Zalipsky, "Synthesis of an End-Group Functionalized Polyethylene Glycol-Lipid Conjugate for Preparation of Polymer-Grafted Liposomes", Bioconjugate Chem., vol. 4, pp. 296-299, (1993).
Zier, et al., "Polyethylene Glycol Bound Benzyl and Fluorenyl Derivatives as Solubilizing Side-Chain Protecting Groups in Peptide Synthesis", vol. 35, No. 7, pp. 1039-1042, (1994).
Enzon Pharmaceuticals, Macromolecular Engineering Technologies, pp. 1-14, (2004).
Nektar—Transforming Therapeutics, Nektar Molecule Engineering: Polyethyene Glycol and Derivatives for Advanced PEGylation, pp. 1-20, (Catalog—2003).
Nektar—Transforming Therapeutics, Nektar Advanced PEGylation: Polyethylene Glycol and Derivatives for Advanced PEGylation, pp. 1-24, (Catalog—2004).
NOF Corporation, PEG Derivatives, Phospholipid and Drug Delivery Materials for Pharmaceuticals, pp. 1-46, (Catalogue 2003-1st).
NOF Corporation, PEG Derivatives, Phospholipid and Drug Delivery Materials for Pharmaceuticals, pp. 1-50, (Catalogue 2003-2nd).
NOF Corporation, PEG Derivatives, Phospholipids and Drug Delivery Materials for Pharmaceutical Products and Formulations, pp. 1-59, (Catalogue Ver. 8—Apr. 2006).
Polypure, Products; PEG amines; PEG acids and amino acids; PEG thiols and disulfides; Biotins, (Apr. 2004).
Polypure, Products; PEG amines; PEG acids and amino acids; PEG thiols and disulfides, Biotins, (Apr. 2005).
Quanta Biodesign, Labeling, Derivatization and Crosslinking Reagents for Biological and Related Materials with dPEG, pp. 1-38, (Mar. 12, 2004).
Quanta Biodesign, Labeling, Modification and Crosslinking Reagents incorporating our unique monodispersed dPEG Technology, pp. 1-31, (Nov. 5, 2004).
Quanta Biodesign, Ltd., Leading innovator, producer and provider of monodisperse discrete PEG (dPEG) derivatives, (Product Catalog), pp. 1-51, (Updated: Jul. 18, 2005).
Quanta Biodesign, Ltd., Leading innovator, producer and provider of monodisperse discrete PEG (dPEG) derivatives, (Product Catalog), pp. 1-51, (Updated: Nov. 17, 2005).
Shearwater Polymers, Inc., pp. 2-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—2000).
Shearwater Corporation, Polyethylene Glycol and Derivatives for Biomedical Applications, pp. 1-17, (Catalog—2001).
PCT International Search Report and the Written Opinion in PCT Patent Application No. PCT/US2007/016486 mail date Jan. 23, 2008.
Office Communication dated Apr. 29, 2011, corresponding to European Patent Application No. 07836169.8-2109.
International Preliminary Report on Patentability, corresponding to PCT Application No. PCT/US2007/016486 mailed Feb. 5, 2009.

* cited by examiner

POLYMERIC REAGENTS COMPRISING A TERMINAL VINYLIC GROUP AND CONJUGATES FORMED THEREFROM

CROSS-REFERENCE TO RELATED APPLICATIONS

This application is a 35 USC §371 application of International Application No. PCT/US2007/016486 filed Jul. 20, 2007, designating the United States, which claims priority to U.S. Application No. 60/832,411 filed Jul. 21, 2006, both of which are hereby incorporated by reference in their entirety.

BACKGROUND OF THE INVENTION

The present invention relates generally to polymeric reagents useful in providing a conjugate between a polymer and another moiety. In addition, the invention relates to, among other things, compositions comprising the polymeric reagents, conjugates of the polymeric reagents, methods for synthesizing the polymeric reagents and methods for conjugating the polymeric reagents to active agents and other moieties.

BACKGROUND OF THE INVENTION

Conjugating a biologically active polypeptide to a water-soluble polymer avoids some of the drawbacks of injectable delivery. In particular, water-soluble polymer-biologically active polypeptide conjugates can allow for conjugates having reduced immunogenicity and antigenicity, increased water solubility, greatly increased half-lives compared to their unconjugated counterparts (as a result of decreased clearance through the kidney and/or decreased enzymatic degradation in the systemic circulation), and less frequent dosing requirements (as a result of having a greater half-life). Harris et al. have provided a review of the effects of conjugating a water-soluble polymer to an active agent. Harris et al. (2003) *Nat. Rev. Drug Discov.* 2(3):214-221.

A polyethylene glycol derivative can serve as the water-soluble polymer used to form conjugates with biologically active polypeptides. When an active agent is conjugated to a polymer of polyethylene glycol or "PEG," the conjugated active agent is conventionally referred to as being "PEGylated."

The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kenilworth, N.J.), MACUGEN® pegaptanib sodium injection (Pfizer Inc., New York, N.Y.), SOMAVERT® pegvisomant (Pfizer Inc., New York, N.Y.) and NEULASTA® PEG-filgrastim (Amgen Inc., Thousand Oaks, Calif.) demonstrates that administration of a conjugated form of an active agent can have significant advantages over the unconjugated counterpart.

"Reversible PEGylation"—the approach where the active agent (or a moiety having increased activity compared to the PEGylated active agent) is released in vivo—has been proposed in those instances where PEGylaton results in a conjugate that has relatively low pharmacologic activity. For example, U.S. Patent Application Publication No. 2005/0079155 describes conjugates using reversible linkages. As described in this publication, reversible linkages can be effected through the use of an enzyme substrate moiety. It has been pointed out, however, that approaches relying on enzymatic activity are dependent on the availability of enzymes. See Peleg-Schulman (2004) *J. Med. Chem.* 47:4897-4904. Thus, additional approaches that do not rely on enzymatic processes for degradation have been described as being desirable.

One such approach for reversible PEGylation describes a polymeric reagent comprising a fluorene moiety upon which a branched polymer is attached using maleimide chemistry. See Peleg-Schulman (2004) *J. Med. Chem.* 47:4897-4904 and WO 2004/089280. U.S. Patent Application Publication No. 2006/0293499, describes (among other things) conjugates having a degradable linkage and polymeric reagents useful in preparing such conjugates. Each polymeric reagent has a particular strategy (typically carried out through a particular functional group or groups) to provide the abilities to first initially attach the water-soluble polymer to the active agent and then subsequently release the active agent (or some pharmacologically active residue of the conjugate) in vivo.

Notwithstanding these described polymeric reagents, however, there continues a need to provide additional polymeric reagents, with (for example) different or alternative strategies for initial coupling to an active agent and subsequent release of a pharmacologically active residue in vivo. Thus, the present invention seeks to solve these and other needs in the art.

SUMMARY OF THE INVENTION

In one or more embodiments of the invention, a polymeric reagent of Formula I is provided, the polymeric reagent having the formula:

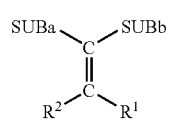

(Formula I)

wherein:

$R^1$ is H or an organic radical;

$R^2$ is H or an organic radical; and with respect to SUBa and SUBb, one of the following:

(i) SUBa is selected from the group consisting of —$R^3$, —$R^{me1}$, —$X^1$-(POLY$^1$)$_a$, and —$R^{de1}$—$X^1$-(POLY$^1$)$_a$, wherein $R^3$ is H or an organic radical, —$R^{me1}$ is an electron altering group having a single attachment site, $R^{de1}$ is an electron altering group having two attachment sites, $X^1$ is a spacer moiety, each POLY$^1$ is a water-soluble polymer, and (a) is an integer having a value of 1 through 3;

SUBb is selected from the group consisting of —$R^4$, —$R^{me2}$, —$X^2$-(POLY$^2$)$_b$, —$R^{de2}$—$X^1$-(POLY$^2$)$_b$, wherein $R^4$ is H or an organic radical, $R^{me2}$ is an electron altering group having a single attachment site, $R^{de2}$ is an electron altering group having two attachment sites, $X^2$ is a spacer moiety, each POLY$^2$ is a water-soluble polymer, and (b) is an integer having a value of 1 through 3;

with the proviso that at least one of SUBa and SUBb includes at least one water-soluble polymer and at least one of SUBa and SUBb includes at least one electron altering group (whether it be an electron altering group having a single attachment site or an electron altering group having two attachment sites); or (ii) SUBa and SUBb combine to form a structure of Formula Ia:

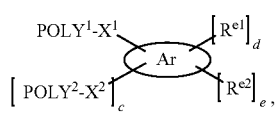
(Formula Ia)

wherein

is an aromatic-containing moiety, $X^1$ is a spacer moiety, $POLY^1$ is a water-soluble polymer, $X^2$ when present is a spacer moiety, $POLY^2$ when present is a water-soluble polymer, $R^{e1}$ when present is an electron altering group, $R^{e2}$ when present is an electron altering group, (c) is either zero or one, (d) is either zero or one, and (e) is either zero or one.

In one or more embodiments of the invention, a polymeric reagent of Formula II is provided, the polymeric reagent having the formula:

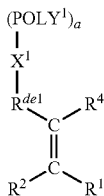
(Formula II)

wherein:
$R^1$ is H or an organic radical;
$R^2$ is H or an organic radical;
$R^4$ is H or an organic radical;
$R^{de1}$ is an electron altering group having two attachment sites;
$X^1$ is a spacer moiety;
$POLY^1$ is a water-soluble polymer; and
(a) is an integer having a value of 1 through 3.

In one or more embodiments of the invention, a polymeric reagent of Formula III is provided, the polymeric reagent having the formula:

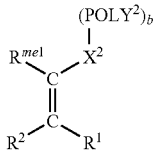
(Formula III)

wherein:
$R^1$ is H or an organic radical;
$R^2$ is H or an organic radical;
$R^{me1}$ is an electron altering group having two attachment sites;
$X^2$ is a spacer moiety;
$POLY^2$ is a water-soluble polymer; and
(b) is an integer having a value of 1 through 3.

In one or more embodiments of the invention, a polymeric reagent of Formula IV is provided, the polymeric reagent having the formula:

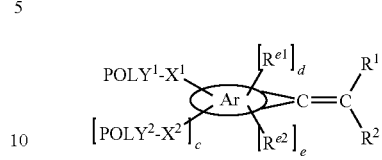
(Formula IV)

wherein:
$R^1$ is H or an organic radical;
$R^2$ is H or an organic radical;

is an aromatic-containing moiety;
$X^1$ is a spacer moiety;
$POLY^1$ is a water-soluble polymer;
$X^2$, when present, is spacer moiety;
$POLY^2$, when present, is a water-soluble polymer;
$R^{e1}$, when present, is an electron altering group;
$R^{e2}$, when present, is an electron altering group;
(c) is either zero or one;
(d) is either zero or one; and
(e) is either zero or one.

In one or more embodiments of the invention, a polymeric reagent of Formula V is provided, the polymeric reagent having the formula:

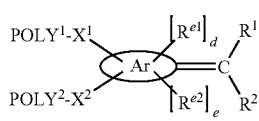
(Formula V)

wherein:
$POLY^1$ is a first water-soluble polymer;
$POLY^2$ is a second water-soluble polymer;
$X^1$ is a first spacer moiety;
$X^2$ is a second spacer moiety;

is an aromatic-containing moiety;
$R^1$ is H or an organic radical;
$R^2$ is H or an organic radical;
(d) is either zero or one;
(e) is either zero or one;
$R^{e1}$, when present, is a first electron altering group; and
$R^{e2}$, when present, is a second electron altering group.

In one or more embodiments of the invention, a polymeric reagent of Formula VI is provided, the polymeric reagent having the formula:

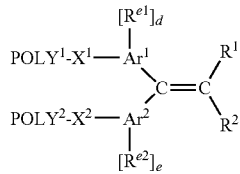

(Formula VI)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group; and
R$^{e2}$, when present, is a second electron altering group.

In one or more embodiments of the invention, a polymeric reagent of Formula VII is provided, the polymeric reagent having the formula:

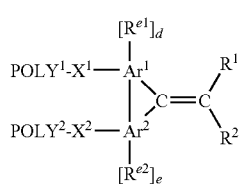

(Formula VII)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group; and
R$^{e2}$, when present, is a second electron altering group.

In one or more embodiments of the invention, a polymeric reagent of Formula VIII is provided, the polymeric reagent having the formula:

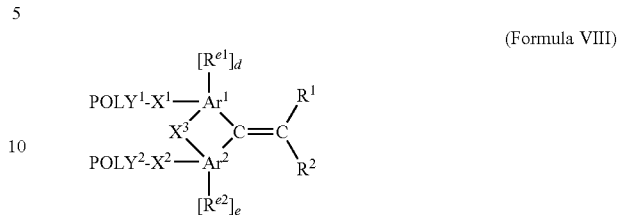

(Formula VIII)

wherein:
POLY$^1$ is a first water-soluble polymer;
POLY$^2$ is a second water-soluble polymer;
X$^1$ is a first spacer moiety;
X$^2$ is a second spacer moiety;
X$^3$ is a third spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group; and
R$^{e2}$, when present, is a second electron altering group.

In one or more embodiments of the invention, a polymeric reagent of Formula IX is provided, the polymeric reagent having the formula:

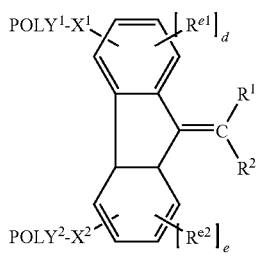

(Formula IX)

wherein:
POLY$^1$ is a first water-soluble polymer;
POLY$^2$ is a second water-soluble polymer;
X$^1$ is a first spacer moiety;
X$^2$ is a second spacer moiety;
R$^1$ is H or an organic radical;
R$^2$ is H or an organic radical;
(d) is either zero or one;
(e) is either zero or one;
R$^{e1}$, when present, is a first electron altering group; and
R$^{e2}$, when present, is a second electron altering group.

In one or more embodiments of the invention, a polymeric reagent of Formula X is provided, the polymeric reagent having the formula:

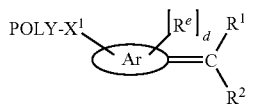

(Formula X)

wherein:

POLY is a water-soluble polymer;

X is a spacer moiety (that preferably does not include a

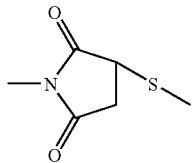

or

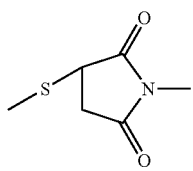

moiety);

is an aromatic-containing moiety;

$R^1$ is H or an organic radical;
$R^2$ is H or an organic radical;
(d) is either zero or one; and
$R^e$, when present, is an electron altering group.

In one or more embodiments of the invention, a conjugate of Formula I-C is provided, the conjugate having the formula:

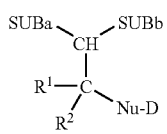

(Formula I-C)

wherein:

$R^1$ is H or an organic radical;
$R^2$ is H or an organic radical;
Nu-D is a residue of a nucleophile-containing biologically active agent (where Nu is the nucleophile, typically a thiol, at which attachment occurs); and with respect to SUBa and SUBb, one of the following:

(i) SUBa is selected from the group consisting of —$R^3$, —$R^{me1}$, —$X^1$-(POLY$^1$)$_a$, and —$R^{de1}$—$X^1$-(POLY$^1$)$_a$, wherein $R^3$ is H or an organic radical, —$R^{me1}$ is an electron altering group having a single attachment site, $R^{de1}$ is an electron altering group having two attachment sites, $X^1$ is a spacer moiety, each POLY$^1$ is a water-soluble polymer, and (a) is an integer having a value of 1 through 3;

SUBb is selected from the group consisting of —$R^4$, $R^{me2}$, —$X^2$-(POLY$^2$)$_b$, —$R^{de2}$—$X^2$-(POLY$^2$)$_b$, wherein $R^4$ is H or an organic radical, $R^{me2}$ is an electron altering group having a single attachment site, $R^{de2}$ is an electron altering group having two attachment sites, $X^2$ is a spacer moiety, each POLY$^2$ is a water-soluble polymer, and (b) is an integer having a value of 1 through 3;

with the proviso that at least one of SUBa and SUBb includes at least one water-soluble polymer and at least one of SUBa and SUBb includes at least one electron altering group (whether it be an electron altering group having a single attachment site or an electron altering group having two attachment sites); or (ii) SUBa and SUBb combine to form a structure of Formula Ia:

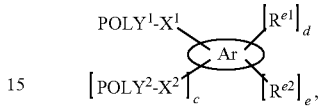

(Formula Ia)

wherein

is an aromatic-containing moiety, $X^1$ is a spacer moiety, POLY$^1$ is a water-soluble polymer, $X^2$ when present is a spacer moiety, POLY$^2$ when present is a water-soluble polymer, $R^{e1}$ when present is an electron altering group, $R^{e2}$ when present is an electron altering group, (c) is either zero or one, (d) is either zero or one, and (e) is either zero or one.

In one or more embodiments of the invention, a conjugate of Formula II-C is provided, the conjugate having the structure:

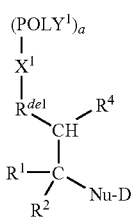

(Formula II-C)

wherein:

$R^1$ is H or an organic radical;
$R^2$ is H or an organic radical;
$R^4$ is H or an organic radical;
$R^{de1}$ is an electron altering group having two attachment sites;
$X^1$ is a spacer moiety;
POLY$^1$ is a water-soluble polymer;
(a) is an integer having a value of 1 through 3; and
Nu-D is a residue of a nucleophile-containing biologically active agent (where Nu is the nucleophile at which attachment occurs).

In one or more embodiments of the invention, a conjugate of Formula III-C is provided, the conjugate having the formula:

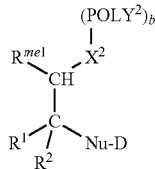

(Formula III-C)

wherein:

$R^1$ is H or an organic radical;

$R^2$ is H or an organic radical;

$R^{me1}$ is an electron altering group having two attachment sites;

$X^2$ is a spacer moiety;

$POLY^2$ is a water-soluble polymer;

(b) is an integer having a value of 1 through 3; and

Nu-D is a residue of a nucleophile-containing biologically active agent (where Nu is the nucleophile at which attachment occurs).

In one or more embodiments of the invention, a conjugate of Formula IV-C is provided, the conjugate having the following formula:

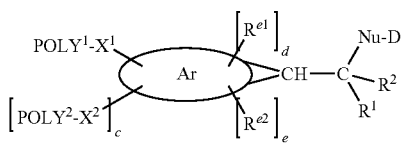

(Formula IV-C)

wherein:

$R^1$ is H or an organic radical;

$R^2$ is H or an organic radical;

is an aromatic-containing moiety;

$X^1$ is a spacer moiety;

$POLY^1$ is a water-soluble polymer;

$X^2$, when present, is a spacer moiety;

$POLY^2$, when present, is a water-soluble polymer;

$R^{e1}$, when present, is an electron altering group;

$R^{e2}$, when present, is an electron altering group;

(c) is either zero or one;

(d) is either zero or one;

(e) is either zero or one; and

Nu-D is a residue of a nucleophile-containing biologically active agent (where Nu is the nucleophile at which attachment occurs).

In one or more embodiments of the invention, a conjugate of Formula V-C is provided, the conjugate having the formula:

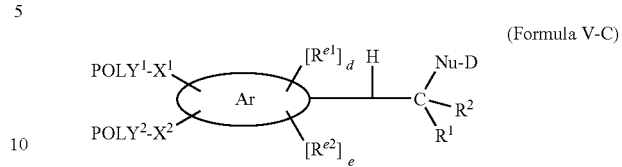

(Formula V-C)

wherein:

$POLY^1$ is a first water-soluble polymer;

$POLY^2$ is a second water-soluble polymer;

$X^1$ is a first spacer moiety;

$X^2$ is a second spacer moiety;

is an aromatic-containing moiety;

$R^1$ is H or an organic radical;

$R^2$ is H or an organic radical;

(d) is either zero or one;

(e) is either zero or one;

$R^{e1}$, when present, is a first electron altering group;

$R^{e2}$, when present, is a second electron altering group; and

Nu-D is a residue of a nucleophile-containing biologically active agent (where Nu is the nucleophile at which attachment occurs).

In one or more embodiments of the invention, a conjugate of Formula VI-C is provided, the conjugate having the formula:

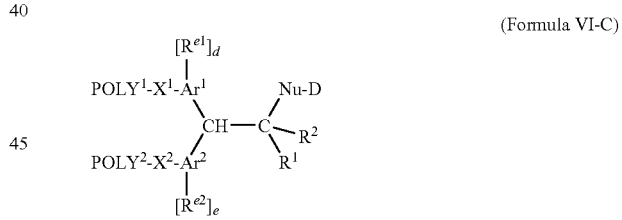

(Formula VI-C)

wherein:

$POLY^1$ is a first water-soluble polymer;

$POLY^2$ is a second water-soluble polymer;

$X^1$ is a first spacer moiety;

$X^2$ is a second spacer moiety;

$Ar^1$ is a first aromatic moiety;

$Ar^2$ is a second aromatic moiety;

$R^1$ is H or an organic radical;

$R^2$ is H or an organic radical;

(d) is either zero or one;

(e) is either zero or one;

$R^{e1}$, when present, is a first electron altering group;

$R^{e2}$, when present, is a second electron altering group;

Nu-D is a residue of a nucleophile-containing biologically active agent (where Nu is the nucleophile at which attachment occurs).

In one or more embodiments of the invention, a conjugate of Formula VII-C is provided, the conjugate having the formula:

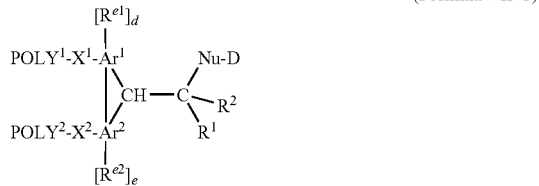

(Formula VII-C)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group;
R$^{e2}$, when present, is a second electron altering group; and
Nu-D is a residue of a nucleophile-containing biologically active agent (where Nu is the nucleophile at which attachment occurs).

In one or more embodiments of the invention, a conjugate of Formula VIII-C is provided, the conjugate having the formula:

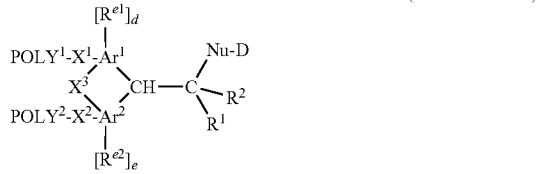

(Formula VIII-C)

wherein:
POLY$^1$ is a first water-soluble polymer;
POLY$^2$ is a second water-soluble polymer;
X$^1$ is a first spacer moiety;
X$^2$ is a second spacer moiety;
X$^3$ is a third spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group;
R$^{e2}$, when present, is a second electron altering group; and
Nu-D is a residue of a nucleophile-containing biologically active agent (where Nu is the nucleophile at which attachment occurs).

In one or more embodiments of the invention, a conjugate of Formula IX-C is provided, the conjugate having the formula:

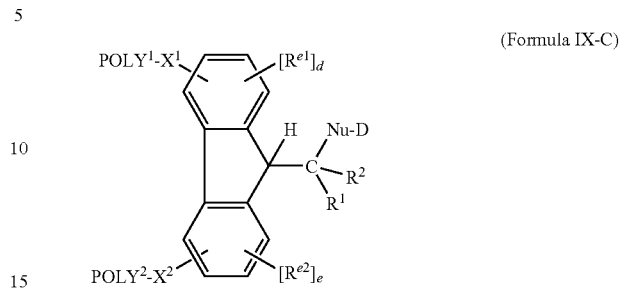

(Formula IX-C)

wherein:
POLY$^1$ is a first water-soluble polymer;
POLY$^2$ is a second water-soluble polymer;
X$^1$ is a first spacer moiety;
X$^2$ is a second spacer moiety;
R$^1$ is H or an organic radical;
R$^2$ is H or an organic radical;
(d) is either zero or one;
(e) is either zero or one;
R$^{e1}$, when present, is a first electron altering group;
R$^{e2}$, when present, is a second electron altering group; and
Nu-D is a residue of a nucleophile-containing biologically active agent (where Nu is the nucleophile at which attachment occurs).

In one or more embodiments of the invention, a conjugate of Formula X-C is provided, the conjugate having the formula:

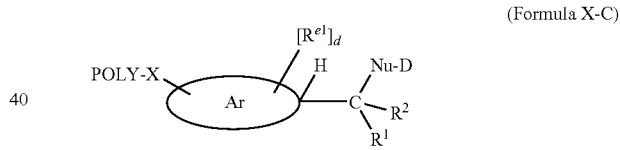

(Formula X-C)

wherein:
POLY is a water-soluble polymer;
X is a spacer moiety (that preferably does not include a

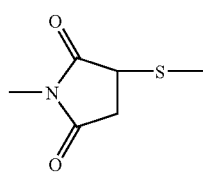

or

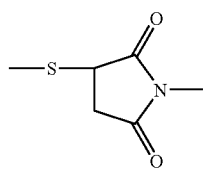

moiety);

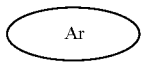

is an aromatic-containing moiety;

$R^1$ is H or an organic radical;

$R^2$ is H or an organic radical;

(d) is either zero or one;

$R^e$, when present, is an electron altering group; and

Nu-D is a residue of a nucleophile-containing biologically active agent (where Nu is the nucleophile at which attachment occurs).

In one or more embodiments of the invention, a polymeric reagent prepared in accordance with the methods described herein for preparing polymeric reagents is provided. Such a polymeric reagent shall be considered a purified polymeric reagent. At a minimum, a purified polymeric reagent shall, for example, be isolated from in vivo milieu (such as plasma). Preferably the polymeric reagent shall be in solid form.

In one or more embodiments of the invention, purified compositions comprising the polymeric reagents are provided.

In one or more embodiments of the invention, methods for preparing conjugates are provided.

In one or more embodiments of the invention, conjugates prepared using the novel polymeric reagents described herein are provided. Preferably, the conjugate is a "purified conjugate," meaning that the conjugate is isolated from in vivo milieu (such as plasma). Preferably the conjugate shall be in solid form.

In one or more embodiments of the invention, pharmaceutical preparations comprising the conjugates are provided.

In one or more embodiments of the invention, methods for administering the conjugates are provided.

DETAILED DESCRIPTION OF THE INVENTION

Figure 1A:
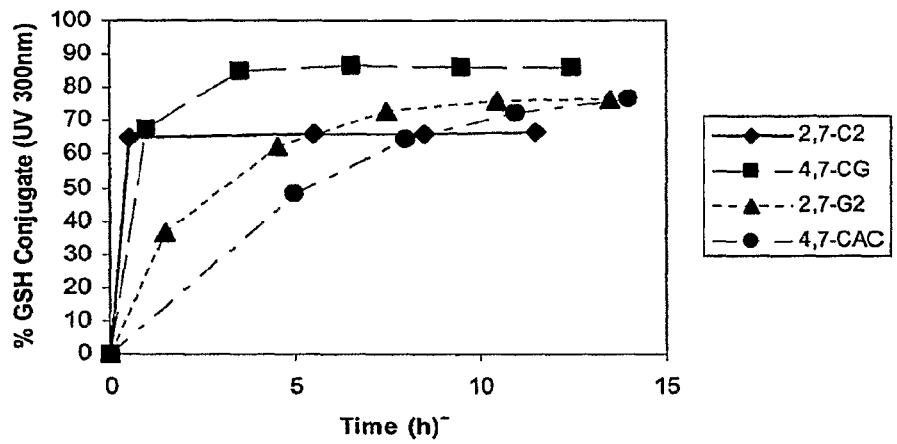
FIG. 1A shows the area percent of negatively charged PEG2-fulvene-GSH (thioether) conjugate vs. neutral PEG2-fulvene 20K reagent. Polymer was 0.5 mmol in 50 mM HEPES pH 7.4 with GSH 15 mM at 37° C., nitrogen sparged. Fulvene structure variations are indicated in key. Percentages determined by HPLC size exclusion chromatography.

Before describing the present invention in detail, it is to be understood that this invention is not limited to the particular polymers, synthetic techniques, active agents, and the like, as such may vary.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_m$—," depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled to can be determined by using a suitable detector. Such labels include, without limitation, fluorescers, chemiluminescers, moieties used in enzyme labeling, calorimetric (e.g., dyes), metal ions, radioactive moieties, and the like. Suitable detectors include photometers, films, spectrometers, and the like.

"Non-naturally occurring" with respect to a polymer or water-soluble polymer means a polymer that in its entirety is not found in nature. A non-naturally occurring polymer or water-soluble polymer may, however, contain one or more subunits or portions of a subunit that are naturally occurring, so long as the overall polymer structure is not found in nature.

The term "water-soluble polymer" is any polymer that is soluble in water at room temperature. Typically, a water-soluble polymer will transmit at least about 75%, more preferably at least about 95% of light, transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

Molecular weight in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-pint depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

As used herein, the term "carboxylic acid" is a moiety having a

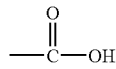

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. With regard to protecting groups suited for a carboxylic acid and any other functional group described herein, reference is made to Greene et al., "PROTECTIVE GROUPS IN ORGANIC SYNTHESIS" $3^{rd}$ Edition, John Wiley and Sons, Inc., New York, 1999.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive functional group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The terms "spacer" or "spacer moiety" are used herein to refer to an atom or a collection of atoms optionally used to link one moiety to another, such as a water-soluble polymer to an aromatic-containing moiety. The spacer moieties of the invention may be hydrolytically stable or may include one or more physiologically hydrolyzable or enzymatically degradable linkages.

An "organic radical" as used includes, for example, alkyl, substituted alkyl, alkenyl, substituted alkenyl, alkynyl, substituted alkynyl, aryl and substituted aryl.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 2-pentyl, 3-pentyl, 3-methyl-3-pentyl, and the like. As used herein, "alkyl" includes cycloalkyl when three or more carbon atoms are referenced and lower alkyl.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy; lower phenyl (e.g., 0-2 substituted phenyl); substituted phenyl; and the like. "Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyl, etc.), and more preferably $C_1$-$C_7$ alkyl.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-butynyl, isopentynyl, octynyl, decynyl, and so forth.

The term "alkylene" as used herein refers to a branched or unbranched alkyl group that is attached at two points on the alkyl group thus making it a linker. Typical preferred alkylene groups include ethylene ($-CH_2CH_2-$), propylene ($-CH_2CH_2CH_2-$), butylene ($-CH_2CH_2CH_2CH_2-$), isobutylene ($-CH_2CH(CH_3)CH_2-$), hexylene ($-CH_2CH_2CH_2CH_2CH_2CH_2-$), and the like.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl. An aromatic moiety (e.g., $Ar^1$, $Ar^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A "physiologically cleavable" or "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

A "degradable linkage" includes, but is not limited to, a physiologically cleavable bond, a hydrolyzable bond, and an enzymatically degradable linkage. Thus, a "degradable linkage" is a linkage that may undergo either hydrolysis or cleavage by some other mechanism (e.g., enzyme-catalyzed, acid-catalyzed, base-catalyzed, and so forth) under physiological conditions. For example, a "degradable linkage" can involve reverse conjugate addition.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes (carbamates), and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

As used herein, the term "ionizable hydrogen atom" ("$H_\alpha$") means a hydrogen atom that can be removed in the presence of a base, often a hydroxide or amine base. Typically, the "ionizable hydrogen atom" ("$H_\alpha$") will be a hydrogen atom attached to a carbon atom that, in turn, is attached to one or more aromatic moieties or another group or groups that in some way stabilize the carbanion that would form from loss of the ionizable hydrogen atom as a proton (or the transition state leading to said carbanion).

As used herein, "drug release rate" means a rate (stated as a half-life) in which half of the total amount of polymer-active agent conjugates in a system will cleave into the active agent and a polymeric residue.

"Optional" and "optionally" mean that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise. Thus, for example, the definition of "POLY," "spacer moiety," "$R^{e1}$" and so forth with respect to a polymeric reagent is equally applicable to a conjugate provided herein.

As previously stated, the present invention comprises (among other things) polymeric reagents useful in providing conjugates having a degradable linkage between a polymer and another moiety. Without wishing to be bound by theory, it is believed that the conjugates are believed to degrade in such as way as to minimize or eliminate entirely any residue or "tag" of the polymeric reagent used to form the conjugate. As a consequence, it is possible to regenerate or recover the original unconjugated and unmodified form of the active agent.

As discussed herein and as evidenced by the formulae provided herein, the polymeric reagents of the invention comprise one or more water-soluble polymers (e.g., "$POLY^1$" and "$POLY^2$" as set forth in various formulae provided herein), an aromatic-containing moiety bearing, an electron withdrawing group, and a vinylic functional group. The vinylic functional group (that is typically rendered more active by the presence of the electron withdrawing group(s)) reacts with a nucleophile on a nucleophile-containing active agent in a nucleophilic addition reaction to form the corresponding conjugate. Upon administration of the conjugate to a patient, release of the active agent is achieved by an elimination reaction (wherein an alpha hydrogen in the conjugate is activated for removal by the presence of the electron withdrawing group(s)). Exemplary nucleophilic-containing active agents thiol-containing active agents and amine-containing active agents. With respect to thiol-containing active agents, biologically active polypeptides having a free (e.g., not involved in disulfide bonding) thiol associated with the side chain of a cysteine residue are preferred. With respect to amine-containing active agents, biologically active polypeptides are preferred inasmuch as each has an N-terminal amine for reaction with the vinylic functional group. In addition, biologically active polypeptides having an amine associated with the side chain of a lysine residue are preferred. In addition, various components of the described polymeric reagents can be attached to the rest of the polymeric reagent through an optional spacer moiety (e.g., as "X", "$X^1$", "$X^2$" and "$X^3$" as set forth in various formulae provided herein). In addition one, two, three, four or more electron altering groups (whether they have a single attachment site or two attachment sites) (e.g., "$R^e$", "$R^{e1}$", "$R^{e2}$", "$R^{e3}$", "$R^{e4}$", "$R^{de}$", "$R^{de1}$", "$R^{de2}$", "$R^{de3}$", "$R^{de4}$" and so forth as set forth in various formulae provided herein) can be attached to or included within the aromatic-containing moiety (in both the polymeric reagent as well as the conjugate).

Before describing exemplary polymeric reagents of the invention, embodiments of a water-soluble polymer, an aromatic-containing moiety, an electron altering group, and a spacer moiety will first be discussed. The following descriptions of a water-soluble polymer, an aromatic moiety, an electron altering group, and a spacer moiety are applicable not only to the polymeric reagent, but to the corresponding conjugates formed using the described polymeric reagents.

With respect to a given water-soluble polymer, each water-soluble polymer (e.g., POLY, $POLY^1$ and $POLY^2$) can comprise any polymer so long as the polymer is water-soluble and non-peptidic. Although preferably a poly(ethylene glycol), a water-soluble polymer for use herein can be, for example, other water-soluble polymers such as other poly(alkylene glycols), such as poly(propylene glycol) ("PPG"), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. The water soluble polymer can be a homopolymer, copolymer, terpolymer, nonrandom block polymer, and random block polymer of any of the foregoing. In addition, a water-soluble polymer can be linear, but can also be in other forms (e.g., branched, forked, and the like) as will be described in further detail below. In the context of being present within an overall structure, a water-soluble polymer has from 1 to about 300 termini.

In instances where the polymeric reagent comprises two or more water-soluble polymers, each water-soluble polymer in the overall structure can be the same or different. It is preferred, however, that all water-soluble polymers in the overall structure are of the same type. For example, it is preferred that all water-soluble polymers within a given structure are each a poly(ethylene glycol).

Although the weight average molecular weight of any individual water-soluble polymer can vary, the weight average molecular weight of any given water-soluble polymer will typically be in the following range: 100 Daltons to about 150,000 Daltons. Exemplary ranges, however, include weight-average molecular weights in the following ranges:

about 880 Daltons to about 5,000 Daltons; in the range of greater than 5,000 Daltons to about 100,000 Daltons; in the range of from about 6,000 Daltons to about 90,000 Daltons; in the range of from about 10,000 Daltons to about 85,000 Daltons; in the range of greater than 10,000 Daltons to about 85,000 Daltons; in the range of from about 20,000 Daltons to about 85,000 Daltons; in the range of from about 53,000 Daltons to about 85,000 Daltons; in the range of from about 25,000 Daltons to about 120,000 Daltons; in the range of from about 29,000 Daltons to about 120,000 Daltons; in the range of from about 35,000 Daltons to about 120,000 Daltons; in the range of about 880 Daltons to about 60,000 Daltons; in the range of about 440 Daltons to about 40,000 Daltons; in the range of about 440 Daltons to about 30,000 Daltons; and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 440 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 16,000 Daltons, about 17,000 Daltons, about 18,000 Daltons, about 19,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total weight average molecular weight of any of the foregoing can also be used.

In one or more embodiments of the invention, the polymeric reagent will comprise a water-soluble polymer having a size in the range suited for the desired rate of release of the conjugate formed therefrom. For example, a conjugate having a relatively long release rate can be prepared from a polymeric reagent having a size suited for (a) extended circulation prior to degradation of the conjugate, and (b) moderately rapid in vivo clearance of the water-soluble polymer remainder upon degradation of the conjugate. Likewise, when the conjugate has a relatively fast release rate, then the polymeric reagent would typically have a lower molecular weight.

When a PEG is used as the water-soluble polymer in the polymeric reagent, the PEG typically comprises a number of ($OCH_2CH_2$) monomers [or ($CH_2CH_2O$) monomers, depending on how the PEG is defined]. As used throughout the description, the number of repeating units is identified by the subscript "n" in "($OCH_2CH_2$)$_n$." Thus, the value of (n) typically falls within one or more of the following ranges: from 2 to about 3400, from about 4 to about 1500, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

Each water-soluble polymer is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the water-soluble polymers, described herein as well as conjugates of active agents and the polymers are biocompatible and non-immunogenic.

In one form useful, free or nonbound PEG is a linear polymer terminated at each end with hydroxyl groups:

wherein (m') typically ranges from zero to about 4,000, preferably from about 20 to about 1,000.

The above polymer, alpha-,omega-dihydroxylpoly(ethylene glycol), can be represented in brief form as HO-PEG-OH where it is understood that the -PEG-symbol can represent the following structural unit:

where (m') is as defined as above.

Another type of free or nonbound PEG useful in the present invention is methoxy-PEG-OH, or mPEG in brief, in which one terminus is the relatively inert methoxy group, while the other terminus is a hydroxyl group. The structure of mPEG is given below

where (m') is as described above.

Multi-armed or branched PEG molecules, such as those described in U.S. Pat. No. 5,932,462, can also be used as the PEG polymer. For example, PEG can have the structure:

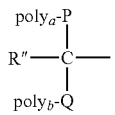

wherein:

poly$_a$ and Poly$_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

In addition, the PEG can comprise a forked PEG. An example of a free or nonbound forked PEG is represented by the following formula:

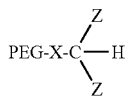

wherein: X is a spacer moiety and each Z is an activated terminal group linked to CH by a chain of atoms of defined length. The chain of atoms linking the Z functional groups to the branching carbon atom serve as a tethering group and may comprise, for example, alkyl chains, ether chains, ester chains, amide chains and combinations thereof. U.S. Pat. No. 6,362,254, discloses various forked PEG structures capable of use in the present invention.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, each water-soluble polymer in the polymeric reagent can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

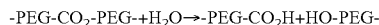

Other hydrolytically degradable linkages, useful as a degradable linkage within a polymer backbone, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Those of ordinary skill in the art will recognize that the foregoing discussion concerning substantially water-soluble polymers is by no means exhaustive and is merely illustrative, and that all polymeric materials having the qualities described above are contemplated. As used herein, the term "water-soluble polymer" refers both to a molecule as well as the residue of water-soluble polymer that has been attached to another moiety.

Each water-soluble polymer is attached (either directly or, for example, through a spacer moiety comprised of one or more atoms or an electron altering group having two attachment sites, such as an electron withdrawing group having two attachment sites) to an aromatic-containing moiety. Thus, the aromatic-containing moiety serves as a point of attachment for one or more water-soluble polymers.

Without wishing to be bound by theory, it is believed to be advantageous to have the aromatic-containing moiety serve as a point of attachment for one or more water-soluble polymers. Specifically, by having each water-soluble polymer attached (either directly or through a spacer moiety) to the aromatic-containing moiety, the often toxic effects associated with aromatic species may be reduced through a steric or blocking effect provided by the water-soluble polymer. This steric or blocking effect can reduce or eliminate potentially damaging metabolic processes that potentially occur when administering some aromatic substances. Thus, the presently described polymeric reagents having two or more water-soluble polymers can provide conjugates that are believed to have reduced toxicity. Such an advantage is believed to differentiate over other polymeric reagents (and corresponding conjugates) wherein, for example, a single branched water-soluble polymer is attached to an aromatic-containing moiety.

Although most any aromatic-containing moiety can be used, the aromatic-containing moiety must provide a site or sites for attachment of various components. In addition, it must be recognized that the aromatic-containing moiety does not itself have to completely aromatic. The aromatic-containing moiety can, for example, contain one or more separate aromatic moieties optionally linked to each other directly or through a spacer moiety comprising one or more atoms.

In some instances the aromatic-containing moiety will take the form of one of the following structures:

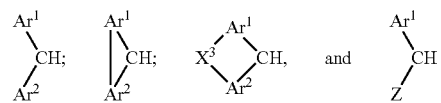

wherein: $Ar^1$ is a first aromatic moiety, $Ar^2$ is a second aromatic moiety, $X^3$ is a spacer moiety, and Z is an electron altering group, relative to H. Such electron altering groups groups are explained in further detail below. Preferred Z groups include, but are not limited to, —Cl, —F, —Br, —I, —$CF_3$, —$CH_2CF_3$, —$CH_2C_6F_5$, —CN, —$NO_2$, —S(O)R, —S(O)Aryl, —S($O_2$)R, —S($O_2$)Aryl, —S($O_2$)OR, —S($O_2$)OAryl, —S($O_2$)NHR, —S($O_2$)NHAryl, —C(O)R, —C(O)Aryl, —C(O)OR, —C(O)NHR, and the like, wherein R is H or an organic radical.

Exemplary aromatic moieties (which can be further substituted with one or more electron altering groups as will be further explained herein) include the following (where, in each case:

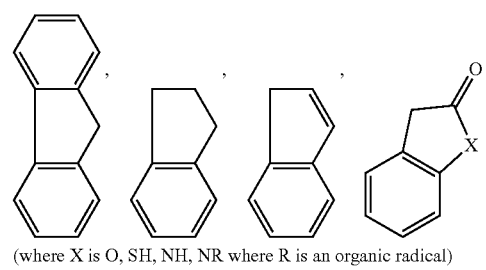

(where X is O, SH, NH, NR where R is an organic radical)

-continued
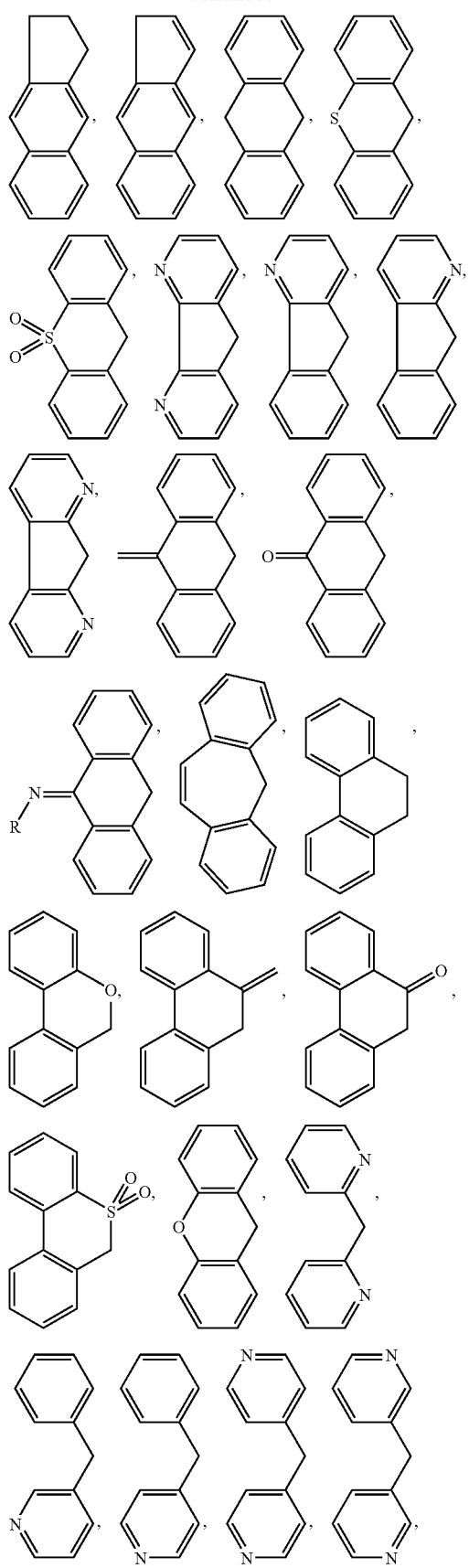
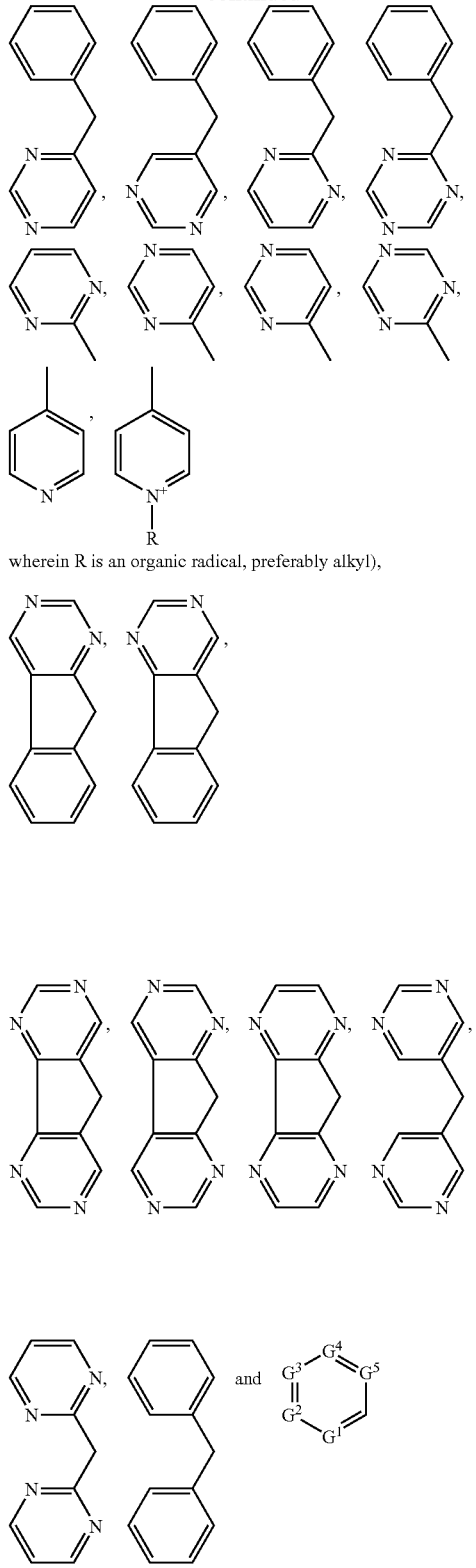
wherein R is an organic radical, preferably alkyl),
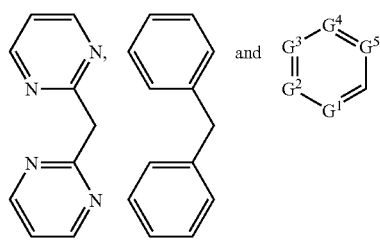
wherein each of $G^1$, $G^2$, $G^3$, $G^4$, and $G^5$ is independently N, C—H or substituted carbon with the proviso that where any of $G^1$, $G^2$, $G^3$, $G^4$, and $G^5$ of G is N, the adjacent atom must be C—H or a substituted carbon. Preferred aromatic moieties include

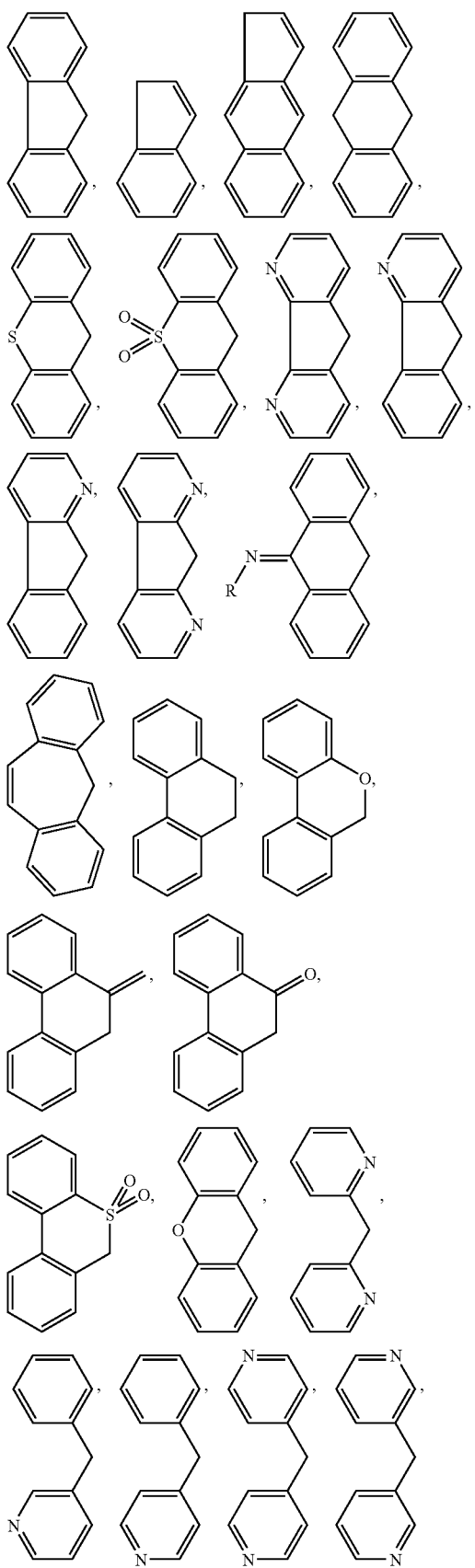

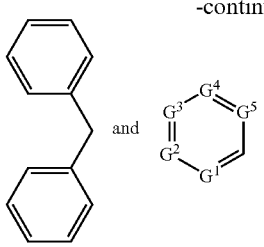

wherein each of $G^1$, $G^2$, $G^3$ $G^4$ and $G^5$ is independently N, C—H or substituted carbon with the proviso that where any of $G^1$, $G^2$, $G^3$, $G^4$ and $G^5$ of G is N, the adjacent atom must be C—H or a substituted carbon.

In one or more embodiments, the aromatic-containing moiety bearing an ionizable hydrogen atom optionally includes one or more electron altering groups ("$R^e$", "$R^{e1}$", "$R^{e2}$", "$R^{de}$", "$R^{de1}$", "$R^{de2}$" and so forth). An electron altering group is a group that is either electron donating (and therefore referred to as an "electron donating group"), or electron withdrawing (and therefore referred to as an "electron withdrawing group"). An electron donating group is a group having the ability to position electrons away from itself and closer to the vinylic functional group. An electron withdrawing group is a group having the ability to position electrons toward itself and away from the vinylic functional group. Hydrogen is used as the standard for comparison in the determination of whether a given group positions electrons away or toward itself.

While not wishing to be bound by theory, electron altering groups—by changing the position of electrons (i.e., the "electron density") influence the rates of the nucleophilic addition-based conjugation reaction and the elimination-based release of the active agent reaction. Thus, it is believed that electron withdrawing groups increase the acidity of an ionizable hydrogen atom (associated with the conjugate) while electron donating groups decrease the acidity of an ionizable hydrogen atom (associated with the conjugate). Electron donating and withdrawing groups affecting the acidity of an ionizable hydrogen atom include groups contained within the spacer moieties (e.g., $X^1$, $X^2$, $X^3$ and so forth) serving to link various constituents of the structures provided herein. Thus, the presence and electron altering group type will influence the rates of reactions associated with the addition/elimination reactions, thereby allowing for the ability to adjust—by selecting the appropriate electron altering groups(s) (typically determined by routine testing)—the rates to optimize the desired performance.

Exemplary electron withdrawing groups include halo (e.g., bromo, fluoro, chloro, and iodo), nitro, carboxy, ester, formyl, keto, azo, amidocarbonyl, amidosulfonyl, carboxamido, sulfonoxy, sulfonamide, ureido, and aryl. Exemplary electron donating groups include hydroxyl, lower alkoxy (e.g., methoxy, ethoxy and the like), lower alkyl (such as methyl, ethyl, and the like), amino, lower alkylamino, di-lower alkylamino, aryloxy (such as phenoxy and the like), arylalkoxy (such as phenoxy and the like), aminoaryls (such as p-dimethylaminophenyl and the like), mercapto, and alkylthio.

In one or more embodiments, the aromatic-containing moiety may include (in addition to one or more water-soluble polymers) one, two three, four, or more electron altering groups. Exemplary instances where the aromatic-containing moiety includes two electron altering groups are shown in the following structures below:

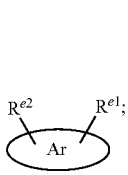

wherein

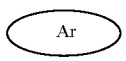

is an aromatic-containing moiety, $Ar^1$ is a first aromatic moiety, $Ar^2$ is a second aromatic moiety, $R^{e1}$ is an electron altering group, and $R^{e2}$ is an electron altering group, while the ionizable hydrogen atom (i.e., $H_\alpha$), the one or more water-soluble polymers, and any other constituents that may be present are not shown. When each of $R^{e1}$ and $R^{e2}$ is different, (a) $R^{e1}$ and $R^{e2}$ can be different electron withdrawing groups, (b) $R^{e1}$ and $R^{e2}$ can be different electron donating groups, (c) or $R^{e1}$ and $R^{e2}$ can be such that one is an electron withdrawing group and the other is an electron donating group. In many circumstances, however, each of $R^{e1}$ and $R^{e2}$ will be the same.

Typically, but not necessarily, placement of an electron altering group on the aromatic-containing moiety is often determined by the preferred entry point of electron altering groups added through aromatic electrophilic or nucleophilic substitution processes. For example, with a fluorene ring, typical positions for addition of electron altering groups by electrophilic aromatic substitution are the "2" and "7" positions. If these positions are occupied by a spacer moiety (which is attached to a water-soluble polymer) other positions on the fluorene ring will be substituted based on factors such as (a) the directing ability of the spacer moiety (e.g., $X^1$ and $X^2$), and (b) steric influences. Often, however, the "4" and "5" positions of a fluorene ring represent the more likely sites for attachment when the "2" and "7" positions are unavailable and especially when the alpha carbon, i.e., the 9-position in fluorene is substituted. For illustration, the positions in the fluorene ring are identified on the following structure:

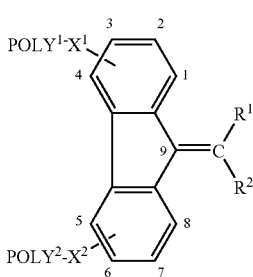

wherein, each of $POLY^1$, $POLY^2$, $X^1$, $X^2$, $R^1$ and $R^2$ is as defined with respect to Formula V, infra. Although exemplary positions of electron altering groups and other groups have been referred to with respect to a fluorene ring, the present discussion of positional location of electron altering groups is applicable to other aromatic systems as well. One of ordinary skill in the art can determine the positional locations in other ring systems.

As previously indicated, electron altering groups can influence the acidity of the ionizable hydrogen atom of the aromatic-containing moiety associated with the conjugate in different ways depending on the nature of the particular electron altering group. For example, due to the proximity of electron altering groups at positions "1" and "8" to the ionizable hydrogen atom in the fluorene ring in the corresponding conjugate, electron altering groups at these positions would have the greatest influence through bond (inductive) effects. When the $POLY^1$-$X^1$— and $POLY^2$-$X^2$— are attached at the 2 and 7 positions, however, addition of an electron altering group at the 4 or 5 positions is more likely, for the reasons mentioned above (i.e., directing effects of the spacer moieties and steric effects). Electron altering groups that interact with the ring through resonance effects, such as amido, carboxy, nitro, and alkoxy groups, can provide the resonance effect at a significant distance from the alpha hydrogen. As a consequence, their placement relatively close to the ionizable hydrogen atom may be less important. From another perspective, it may be advantageous to leave relatively close positions (e.g., the "1" and "4" positions) unsubstituted as the ionizable hydrogen atom that will ultimately become removed will likely be retarded by steric effects of electron altering groups at these positions. Again, although exemplary positions of electron altering groups and other groups have been referred to with respect to a fluorene ring, the present discussion of positional location is applicable to other ring systems as well; one of ordinary skill in the art can determine the corresponding positional locations in other ring systems.

To better understand the release reaction of a conjugate formed with a polymeric reagent of the invention (and to also demonstrate effect of electron altering groups on that process) and without any intent of being bound by theory, a proposed mechanism of the release process is provided. A schematic of the proposed mechanism is shown below utilizing a fluorene moiety as the aromatic-containing moiety. In the schematic, an exemplary conjugate of the invention is shown wherein a carbamate linkage connects the residue of the active agent ("Drug") to the rest of the molecule. The variables "$POLY^1$," "$POLY^2$," "$X^1$," "$X^2$," "$R^1$" and "$R^2$" are as previously defined.

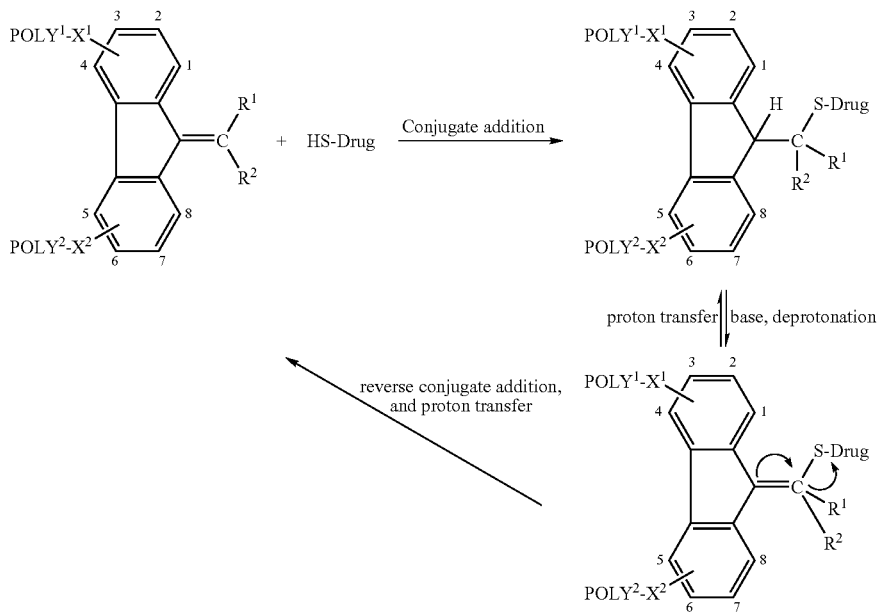

The release process is typically initiated by the attack of a basic molecule, ion, or species that has the capacity to accept a proton in a transfer process. In vivo, this may be any one of several kinds of ionic species or a protein, which has several basic atoms. Elimination occurs to form a substituted fulvene moiety (or corresponding structure when a non-fluorene structure is employed), thereby releasing the active agent or "drug" species, which may initially be attached to a carboxy group, which is rapidly lost under physiological conditions.

The release process can be concerted or stepwise. Regardless of the exact nature of the proton removal step, either a carbanion is formed as an intermediate or a transition state having carbanionic character is involved. Thus, electron donating groups attached to the aromatic rings, which retard the formation of carbanions, will retard the carbanion-formation process, thereby decreasing the release rate. Conversely, electron withdrawing groups, which facilitate the formation of carbanionic species and stabilize carbanionic transition states, will accelerate the carbanion formation process, thereby increasing the release rate.

Advantageously, by including one or more electron altering groups within the polymeric reagent, it is possible to more closely provide the desired rates of the conjugation and release of the active agent. By including one or more electron withdrawing groups, conjugation and release are believed to increase, while the presence of one or more electron donating group is believed to decrease the rates of conjugation and release. Thus, it is believed that the presence of one or more electron altering groups can provide relative stability or instability of a charged intermediate or transition state that may be involved in these reactions. Accordingly, by including one or more such electron altering groups in the polymeric reagents, it is possible to better customize a desired rate of conjugation and release.

It is possible to determine what effect such an electron altering group will have on the conjugation and release rates by preparing a polymeric reagent having the proposed electron altering group, preparing a conjugate using this polymeric reagent, testing the conjugate for drug release rate over time, and comparing the drug release rate to a conjugate prepared with a control polymeric reagent.

A spacer moiety (e.g., "X", "$X^1$", "$X^2$", "$X^3$", and so forth) is any atom or series of atoms connecting one part of a molecule to another. For purposes of the present disclosure, however, a series of atoms is not a spacer moiety when the series of atoms is immediately adjacent to a polymer and the series of atoms is but another monomer such that the proposed spacer moiety would represent a mere extension of the polymer chain. For example, given the partial structure "POLY-X—," and POLY is defined as "$CH_3O(CH_2CH_2O)_m$—" wherein (m) is 2 to 4000 and X is defined as a spacer moiety, the spacer moiety cannot be defined as "—$CH_2CH_2O$—" since such a definition would merely represent an extension of the polymer. In such a case, however, an acceptable spacer moiety could be defined as "—$CH_2CH_2$—"

Exemplary spacer moieties include, but are not limited to, —C(O)—, —S($O_2$)—, —S(O)—, —NH—S($O_2$)—, —S($O_2$)—NH—, —CH=CH—, —O—CH=CH—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —S—$CH_2$—, —$CH_2$—S—, —S—$CH_2$—$CH_2$—, —$CH_2$—S—$CH_2$—, —$CH_2$—$CH_2$—S—, —S—$CH_2$—$CH_2$—$CH_2$—, —$CH_2$—S—$CH_2$—$CH_2$—, —$CH_2$—$CH_2$—S—$CH_2$—, —$CH_2$—$CH_2$—$CH_2$—S—, —S—$CH_2$—$CH_2$—$CH_2$—$CH_2$—, —$CH_2$—S—$CH_2$—$CH_2$—$CH_2$—, —$CH_2$—$CH_2$—S—$CH_2$—$CH_2$—, —$CH_2$—$CH_2$—$CH_2$—S—$CH_2$—, —$CH_2$—$CH_2$—$CH_2$—$CH_2$—S—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—, —$CH_2$—$CH_2$—C(O)—NH—$CH_2$—, —$CH_2$—

—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—C(O)—NH—, —NH—C(O)—CH$_2$—CH$_2$—C(O)—NH—, —NH—C(O)—CH$_2$—CH$_2$—CH$_2$—C(O)—NH—, —NH—C(O)—CH$_2$—CH$_2$—CH$_2$—CH$_2$—C(O)—NH—, —NH—C(O)—CH=CH—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, —NH—C(O)—O—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment. Finally, it is noted that some spacer moieties include an atom or group of atoms that also function as an electron altering group; in such a cases, the inclusion of one or more additional "discrete" (i.e., not a part of a spacer moiety) electron altering groups may not be desired or necessary.

Preferred spacer moieties for X and X$^1$ include those selected from the group consisting of —C(O)—NH—CH$_2$—CH$_2$—, —CH$_2$—CH$_2$—NH—C(O)—, —C(O)—NH—CH$_2$—CH$_2$—CH$_2$—, —CH$_2$—CH$_2$—CH$_2$—NH—C(O)—, —C(O)—NH—CH$_2$—CH$_2$—CH$_2$—CH$_2$—, —CH$_2$—CH$_2$—CH$_2$—CH$_2$—NH—C(O)—, —C(O)—NH—, —NH—C(O)—, —C(O)—NH—CH$_2$—CH$_2$—CH$_2$—CH$_2$—, —CH$_2$—CH$_2$—CH$_2$—CH$_2$—CH$_2$—NH—C(O)—, —NH—C(O)—CH$_2$—CH$_2$—, —CH$_2$—CH$_2$—C(O)—NH—, —CH$_2$—CH$_2$—CH$_2$—C(O)—NH—, —NH—C(O)—CH$_2$—CH$_2$—CH$_2$—CH$_2$—, C(O)—NH—, —NH—C(O)—CH$_2$—CH$_2$—CH$_2$—CH$_2$—, —CH$_2$—, —CH$_2$—CH$_2$—CH$_2$—CH$_2$—CH$_2$—C(O)—NH—, —NH—C(O)—CH$_2$—CH$_2$—C(O)—, —C(O)—CH$_2$—CH$_2$—C(O)—NH—, —NH—C(O)—CH$_2$—CH$_2$—CH$_2$—CH$_2$—C(O)—, —C(O)—CH$_2$—CH$_2$—CH$_2$—CH$_2$—C(O)—NH—, —NH—C(O)—CH$_2$—CH$_2$—CH$_2$—CH$_2$—CH$_2$—C(O)—, —C(O)—CH$_2$—CH$_2$—CH$_2$—CH$_2$—CH$_2$—C(O)—NH—, —C(O)—CH$_2$—CH$_2$—, —CH$_2$—CH$_2$—C(O)—, —C(O)—CH$_2$—CH$_2$—CH$_2$—, —CH$_2$—CH$_2$—CH$_2$—C(O)—, —C(O)—CH$_2$—CH$_2$—CH$_2$—CH$_2$—, —CH$_2$—CH$_2$—CH$_2$—CH$_2$—C(O)—, —CH$_2$—CH$_2$—CH$_2$—C(O)—, —C(O)—CH$_2$—CH$_2$—CH$_2$—CH$_2$—CH$_2$—, —NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—, —C(O)—NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—C(O)—, —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—, —O—CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—O—, —C(O)—NH—CH$_2$—CH$_2$—, —CH$_2$—CH$_2$—NH—C(O)—, —C(O)—NH—CH$_2$—CH$_2$—O—, —O-alkylene-SO$_2$—, —O-alkylene-NHSO$_2$—, —SO$_2$NH-alkylene-O—, -alkylene-SO$_2$—, -alkylene-NHSO$_2$—, —SO$_2$NH-alkylene-, —SO$_2$—, —NHSO$_2$—, —SO$_2$NH—, and —O—CH$_2$—CH$_2$—NH—C(O)—. Preferred spacer moieties for X$^2$ include those selected from the group consisting of —C(O)—NH—CH$_2$—CH$_2$—, —CH$_2$—CH$_2$—NH—C(O)—, —C(O)—NH—CH$_2$—CH$_2$—CH$_2$—, —CH$_2$—CH$_2$—CH$_2$—NH—C(O)—, —C(O)—NH—CH$_2$—CH$_2$—CH$_2$—CH$_2$—, —CH$_2$—CH$_2$—CH$_2$—CH$_2$—NH—C(O)—, —C(O)—NH—, —NH—C(O)—, —C(O)—NH—CH$_2$—CH$_2$—CH$_2$—CH$_2$—, —CH$_2$—CH$_2$—CH$_2$—CH$_2$—NH—C(O)—, —NH—C(O)—CH$_2$—CH$_2$—, —CH$_2$—CH$_2$—C(O)—NH—, —CH$_2$—CH$_2$—CH$_2$—C(O)—NH—, —NH—C(O)—CH$_2$—CH$_2$—CH$_2$—CH$_2$—, —CH$_2$—C(O)—NH—, —NH—C(O)—CH$_2$—CH$_2$—C(O)—NH—, —C(O)—CH$_2$—CH$_2$—C(O)—NH—, —NH—C(O)—CH$_2$—CH$_2$—CH$_2$—C(O)—, —C(O)—CH$_2$—CH$_2$—CH$_2$—CH$_2$—C(O)—NH—, —NH—C(O)—CH$_2$—CH$_2$—CH$_2$—CH$_2$—, —CH$_2$—C(O)—, —C(O)—CH$_2$—CH$_2$—CH$_2$—C(O)—NH—, —NH—C(O)—CH$_2$—CH$_2$—CH$_2$—CH$_2$—, —CH$_2$—C(O)—, —C(O)—CH$_2$—CH$_2$—CH$_2$—, —CH$_2$—CH$_2$—CH$_2$—C(O)—, —C(O)—CH$_2$—CH$_2$—CH$_2$—, —CH$_2$—CH$_2$—CH$_2$—, —CH$_2$—CH$_2$—CH$_2$—CH$_2$—C(O)—, —C(O)—CH$_2$—CH$_2$—CH$_2$—CH$_2$—CH$_2$—, —CH$_2$—CH$_2$—CH$_2$—, —CH$_2$—CH$_2$—C(O)—, —NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—, —C(O)—NH—CH$_2$—CH$_2$—(OCH$_2$CH$_2$)$_{1-3}$—NH—C(O)—, —C(O)—NH—(CH$_2$CH$_2$O)$_{1-3}$—CH$_2$—CH$_2$—NH—C(O)—, —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—, —O—CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—

$CH_2$—O—, —C(O)—NH—$CH_2$—$CH_2$—, —$CH_2$—$CH_2$—NH—C(O)—, —C(O)—NH—$CH_2$—$CH_2$—O—, —O-alkylene-$SO_2$—, —O-alkylene-$NHSO_2$—, —$SO_2$NH-alkylene-O—, -alkylene-$SO_2$—, -alkylene-$NHSO_2$—, —$SO_2$NH-alkylene-, —$SO_2$—, —$NHSO_2$—, —$SO_2$NH—, and —O—$CH_2$—$CH_2$—NH—C(O)—.

Each spacer moiety, when present, in the overall structure can be the same or different than any other spacer moiety in the overall structure. With respect to $X^1$ and $X^2$, it is sometimes preferred that $X^1$ and $X^2$ are the same.

Preferred spacer moieties corresponding to X, $X^1$ and/or $X^2$ include amidocarboxy, carboxyamido, sulfonamide, ester and ureido.

In some embodiments, it is preferred that the spacer moiety (particularly X of Formulae X and X-C) satisfies one or more of the following: lacks sulfur atoms (e.g., lacks "—S—"); lacks phosphorous atoms; is a chain of greater than four atoms; and does not include —CO—$CH_2$—NH—CO—, —CO—CH($CH_3$)—NH—CO— and —CO—$CH_2$—NH—CO—NH. In some embodiments, it is preferred that the spacer moiety (particularly X of Formulae X and X-C) is an atom or groups of atoms with the proviso that the atom or group of atoms is lacks sulfur and phosphorous atoms and is not —NH—CO—O—, —NH—CO—$CH_2$—$NH_2$—CO—NH—, —NH—CO—, —NH—$CH_2$—, —NH—CO—NH—, —NH—CS—NH—, —CO—O—, —CO—NH—, and —$CH_2$—NH—. In some embodiment the spacer moiety (particularly X of Formulae X and X-C) is not -$R^5$-$R^6$, wherein $R^5$ is selected from the group consisting of —NH—, —S—, —CO—, —COO—, —$CH_2$—, —$SO_2$—, —$SO_3$—, —$PO_2$— and —$PO_3$—, and $R^6$ is a bond or a radical selected from the group consisting of —CO—, —COO—, —$CH_2$—, —CH($CH_3$)—, —CO—NH—, —CS—NH, —CO—$CH_2$—NH—CO—, —CO—CH($CH_3$)—NH—CO—, —CO—$CH_2$—NH—CO—NH—, —CO—$R^8$— (wherein $R^8$ is a straight or branched alkylene), a maleimido-containing radical, and triazinyl-containing radical.

In some instances, a spacer moiety and/or any electron altering group may include an amide functionality bonded directly to the aromatic-containing moiety (i.e., wherein the nitrogen of the amide is covalently bonded directed to the aromatic-containing moiety). In some embodiments however, it is preferred that both the spacer moiety and/or any electron altering group does not include an amide functionality (i.e., —NH—C(O)— or —C(O)—NH—) bonded directly to the aromatic-containing moiety. In still other embodiments, it is preferred to provide for "intramolecular trapping" wherein the vinylic functional group reacts with a nearby nucleophilic moiety (e.g., an —SH group) attached to the polymeric reagent. For example, with a fulvene moiety as provided in Formula IX, an —SH group located at position 2 or 8 can act as a nucleophile to which the vinylic functional group can attach, thereby providing for intramolecular trapping.

Exemplary polymeric reagents of the invention will now be discussed in further detail. It must be remembered that while stereochemistry is not specifically shown in any formulae or structures (whether for a polymeric reagent, conjugate, or any other formula or structure), the provided formulae and structures contemplate both enantiomers, as well as compositions comprising mixtures of each enantiomer in equal amounts (i.e., a racemic mixture) and unequal amounts. Thus, for example, a polymeric reagent of Formula VIc in which a single electron altering group ($R^{e1}$) is present includes both enantiomers and mixtures thereof.

An exemplary polymeric reagent of the invention has the following structure:

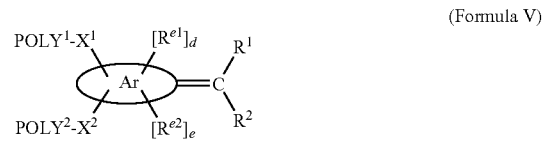
(Formula V)

wherein:

POLY$^1$ is a first water-soluble polymer;

POLY$^2$ is a second water-soluble polymer;

$X^1$ is a first spacer moiety;

$X^2$ is a second spacer moiety;

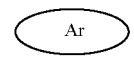

is an aromatic-containing moiety;

$R^1$ is H or an organic radical;

$R^2$ is H or an organic radical;

(d) is either zero or one;

(e) is either zero or one;

$R^{e1}$, when present, is a first electron altering group; and $R^{e2}$, when present, is a second electron altering group.

When the polymeric reagent corresponding to Formula V has no discrete electron altering groups [i.e., when (d) and (e) are both zero with regard to Formula V], a polymeric reagent of the following formula results:

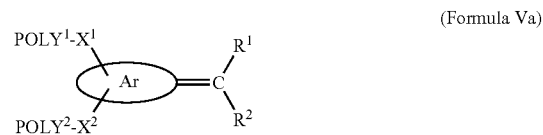
(Formula Va)

wherein each of POLY$^1$, POLY$^2$, $X^1$, $X^2$, $R^1$, $R^2$, and

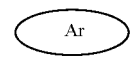

is as previously defined with respect to Formula V.

When the polymeric reagent corresponding to Formula V has a single discrete electron altering group [e.g., when (d) is one and (e) is zero with regard to Formula V], a polymeric reagent of the following formula results:

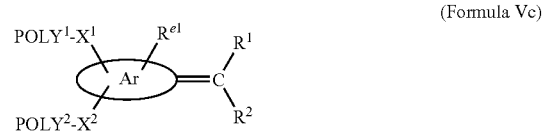
(Formula Vc)

wherein each of POLY$^1$, POLY$^2$, X$^1$, X$^2$, R$^1$, R$^2$,

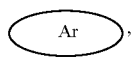

and R$^{e1}$ is a previously defined with respect to Formula V.

When the polymeric reagent corresponding to Formula V has two discrete electron altering groups [i.e., when (d) and (e) are both one with regard to Formula V], a polymeric reagent of the following formula results:

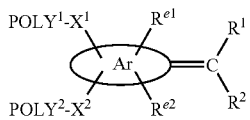
(Formula Vb)

wherein each of POLY$^1$, POLY$^2$, X$^1$, X$^2$, R$^1$, R$^2$,

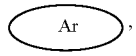

R$^{e1}$ and R$^{e2}$ is as previously defined with respect to Formula V.

In some cases, the polymeric reagent can include individual aromatic moieties that are only linked to each other through a carbon atom. Such a polymeric reagent has the following formula:

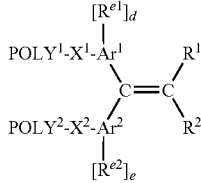
(Formula VI)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group; and
R$^{e2}$, when present, is a second electron altering group.

When the polymeric reagent corresponding to Formula VI has no discrete electron altering groups [i.e., when (d) and (e) are both zero with regard to Formula VI], a polymeric reagent of the following formula results:

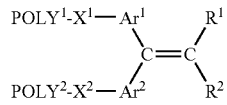
(Formula VIa)

wherein each of POLY$^1$, POLY$^2$, X$^1$, X$^2$, R$^1$, R$^2$, Ar$^1$ and Ar$^2$ is as previously defined with respect to Formula VI.

When the polymeric reagent corresponding to Formula VI has a single discrete electron altering group [e.g., when (d) is one and (e) is zero with regard to Formula VI], a polymeric reagent of the following formula results:

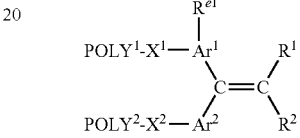
(Formula VIc)

wherein each of POLY$^1$, POLY$^2$, X$^1$, X$^2$, Ar$^1$, Ar$^2$, R$^1$, R$^2$ and R$^{e1}$ is as previously defined with respect to Formula VI.

When the polymeric reagent corresponding to Formula VI has two discrete electron altering groups [i.e., when (d) and (e) are both one with regard to Formula VI], a polymeric reagent of the following formula results:

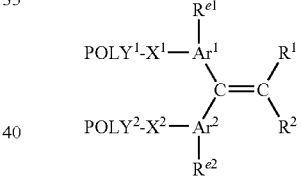
(Formula VIb)

wherein each of POLY$^1$, POLY$^2$, X$^1$, X$^2$, Ar$^1$, Ar$^2$, R$^1$, R$^2$, R$^{e1}$ and R$^{e2}$ is as previously defined with respect to Formula VI.

In still other cases, the polymeric reagent can include individual aromatic moieties that are linked to each other both through a carbon atom as well as another direct bond. Such a polymeric reagent has the following formula:

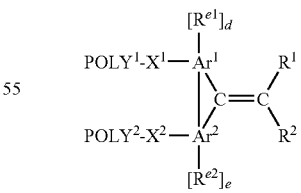
(Formula VII)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;

$R^1$ is H or an organic radical;

$R^2$ is H or an organic radical;

(d) is either zero or one;

(e) is either zero or one;

$R^{e1}$, when present, is a first electron altering group; and $R^{e2}$, when present, is a second electron altering group.

When the polymeric reagent corresponding to Formula VII has no discrete electron altering groups [i.e., when (d) and (e) are both zero with regard to Formula VII], a polymeric reagent of the following formula results:

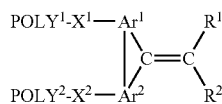

(Formula VIIa)

wherein each of $POLY^1$, $POLY^2$, $X^1$, $X^2$, $R^1$, $R^2$, $Ar^1$ and $Ar^2$ is as previously defined with respect to Formula VII.

When the polymeric reagent corresponding to Formula VII has a single discrete electron altering group [e.g., when (d) is one and (e) is zero with regard to Formula VII], a polymeric reagent of the following formula results:

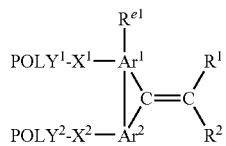

(Formula VIIc)

wherein each of $POLY^1$, $POLY^2$, $X^1$, $X^2$, $R^1$, $R^2$, $Ar^1$, $Ar^2$ and $R^{e1}$, is as previously defined with respect to Formula VII.

When the polymeric reagent corresponding to Formula VII has two discrete electron altering groups [i.e., when (d) and (e) are both one with regard to Formula VII], a polymeric reagent of the following formula results:

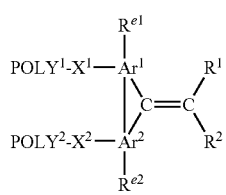

(Formula VIIb)

wherein each of $POLY^1$, $POLY^2$, $X^1$, $X^2$, $R^1$, $R^2$, $Ar^1$, $Ar^2$, $R^{e1}$ and $R^{e2}$ is as previously defined with respect to Formula VII.

In still other cases, the polymeric reagent can include individual aromatic moieties that are linked to each other both through a carbon atom as well as a spacer moiety of one or more atoms. Such a polymeric reagent has the following formula:

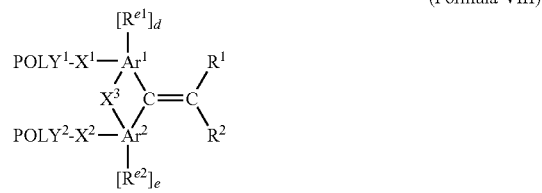

(Formula VIII)

wherein:

$POLY^1$ is a first water-soluble polymer;

$POLY^2$ is a second water-soluble polymer;

$X^1$ is a first spacer moiety;

$X^2$ is a second spacer moiety;

$X^3$ is a third spacer moiety;

$Ar^1$ is a first aromatic moiety;

$Ar^2$ is a second aromatic moiety;

$R^1$ is H or an organic radical;

$R^2$ is H or an organic radical;

(d) is either zero or one;

(e) is either zero or one;

$R^{e1}$, when present, is a first electron altering group; and $R^{e2}$, when present, is a second electron altering group.

When the polymeric reagent corresponding to Formula VIII has no discrete electron altering groups [i.e., when (d) and (e) are both zero with regard to Formula VIII], a polymeric reagent of the following formula results:

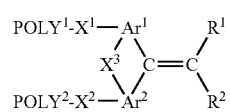

(Formula VIIIa)

wherein each of $POLY^1$, $POLY^2$, $X^1$, $X^2$, $X^3$, $R^1$, $R^2$, $Ar^1$ and $Ar^2$ is as previously defined with respect to Formula VIII.

When the polymeric reagent corresponding to Formula VIII has a single discrete electron altering group [e.g., when (d) is one and (e) is zero with regard to Formula VIII], a polymeric reagent of the following formula results:

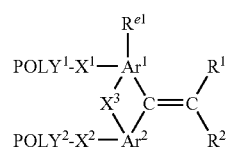

(Formula VIIIc)

wherein each of $POLY^1$, $POLY^2$, $X^1$, $X^2$, $X^3$, $R^1$, $R^2$, $Ar^1$, $Ar^2$, $R^{e1}$ is as previously defined with respect to Formula VIII.

When the polymeric reagent corresponding to Formula VIII has two discrete electron altering groups [i.e., when (d) and (e) are both one with regard to Formula VIII], a polymeric reagent of the following formula results:

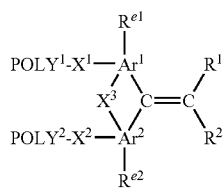

(Formula VIIIb)

wherein each of POLY$^1$, POLY$^2$, X$^1$, X$^2$, X$^3$, Ar$^1$, Ar$^2$, R$^1$, R$^2$, R$^{e1}$ and R$^{e2}$ is as previously defined with respect to Formula VIII.

A preferred polymeric reagent comprises the following structure:

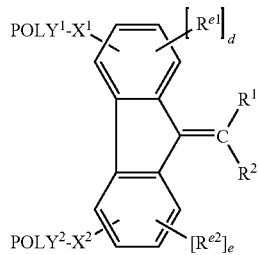

(Formula IX)

wherein:
POLY$^1$ is a first water-soluble polymer;
POLY$^2$ is a second water-soluble polymer;
X$^1$ is a first spacer moiety;
X$^2$ is a second spacer moiety;
R$^1$ is H or an organic radical;
R$^1$ is H or an organic radical;
(a) is either zero or one;
(b) is either zero or one;
R$^{e1}$, when present, is a first electron altering group; and
R$^{e2}$, when present, is a second electron altering group.

When the polymeric reagent corresponding to Formula IX has no discrete electron altering groups [i.e., when (d) and (e) are both zero with regard to Formula IX], a polymeric reagent of the following formula results:

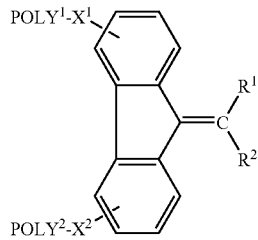

(Formula IXa)

wherein each of POLY$^1$, POLY$^2$, X$^1$, X$^2$, R$^1$ and R$^2$ is as previously defined with respect to Formula IX.

When the polymeric reagent corresponding to Formula IX has a single discrete electron altering group [e.g., when (d) is one and (e) is zero with regard to Formula IX], a polymeric reagent of the following formula results:

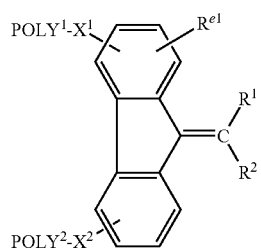

(Formula IXc)

wherein each of POLY$^1$, POLY$^2$, X$^1$, X$^2$, R$^1$, R$^2$ and R$^{e1}$ is as previously defined with respect to Formula IX.

When the polymeric reagent corresponding to Formula IX has two discrete electron altering groups [i.e., when (d) and (e) are both one with regard to Formula IX], a polymeric reagent of the following formula results:

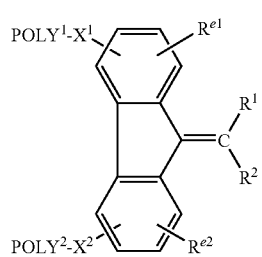

(Formula IXb)

wherein each of POLY$^1$, POLY$^2$, X$^1$, X$^2$, R$^1$, R$^2$, R$^{e1}$ and R$^{e2}$ is as previously defined with respect to Formula IX.

Still another preferred polymeric reagent is of the following structure:

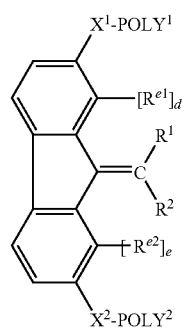

(Formula IXd)

wherein each of POLY$^1$, POLY$^2$, X$^1$, X$^2$, R$^1$, R$^2$, R$^{e1}$, R$^{e2}$, (d) and (e) is as previously defined with respect to Formula IX, with the proviso that R$^{e1}$ is H when (d) is zero and R$^{e2}$ is H when (e) is zero.

Still another preferred polymeric reagent is of the following structure:

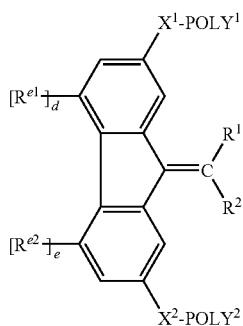

(Formula IXe)

wherein each of POLY$^1$, POLY$^2$, X$^1$, X$^2$, R$^1$, R$^2$, R$^{e1}$, R$^{e2}$, (d) and (e) is as previously defined with respect to Formula IX, with the proviso that R$^{e1}$ is H when (d) is zero and R$^{e2}$ is H when (e) is zero.

Still another preferred polymeric reagent is of the following structure:

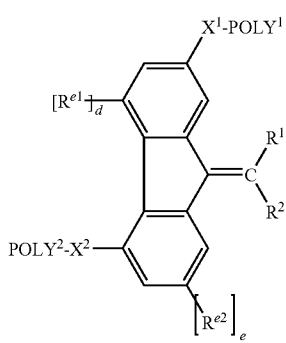

(Formula IXf)

wherein each of POLY$^1$, POLY$^2$, X$^1$, X$^2$, R$^1$, R$^2$, R$^{e1}$, R$^{e2}$, (d) and (e) is as previously defined with respect to Formula IX, with the proviso that R$^{e1}$ is H when (d) is zero and R$^{e2}$ is H when (e) is zero.

Still another preferred polymeric reagent is of the following structure:

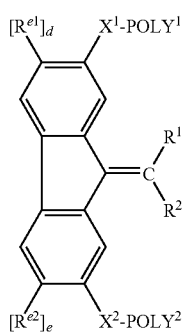

(Formula IXg)

wherein each of POLY$^1$, POLY$^2$, X$^1$, X$^2$, R$^1$, R$^2$, R$^{e1}$, R$^{e2}$, (d) and (e) is as previously defined with respect to Formula IX, with the proviso that R$^{e1}$ is H when (d) is zero and R$^{e2}$ is H when (e) is zero.

Typically, each of POLY$^1$ and POLY$^2$ in each the polymeric reagents of Formulae V, Va, Vc, Vb, VI, VIa, VIc, VIb, VII, VIIa, VIIc, VIIb, VIII, VIIIa, VIIIc, IIIVb, IX, IXa, IXb, IXc, IXd, IXe, IXf and IXg are the same. It is possible, however, to have polymeric reagents wherein each of POLY$^1$ and POLY$^2$ is different. In addition, each of POLY$^1$ and POLY$^2$ will be typically (although not necessarily) a poly(alkylene oxide) such as a poly(ethylene glycol). Further, for a given poly(ethylene glycol), each poly(ethylene glycol) can be terminally capped with an end-capping moiety selected from the group consisting of hydroxyl, alkoxy, substituted alkoxy, alkenoxy, substituted alkenoxy, alkynoxy, substituted alkynoxy, aryloxy and substituted aryloxy. Preferred terminal capping groups, however, include methoxy. Exemplary weight average molecular weights for each poly(ethylene glycol) that serves as a POLY$^1$ and POLY$^2$ in Formulae V, Va, Vc, Vb, VI, VIa, VIc, VIb, VII, VIIa, VIIc, VIIb, VIII, VIIIa, VIIIc, VIIIb, IX, IXa, IXb, IXc, IXd, IXe, IXf and IXg include one or more of the following: in the range of from about 120 Daltons to about 6,000 Daltons; in the range of from about 6,000 Daltons to about 100,000 Daltons; in the range of from about 10,000 Daltons to about 85,000 Daltons; and in the range of from about 20,000 Daltons to about 85,000 Daltons. Exemplary architectures for a given poly(ethylene glycol) that serves as a POLY$^1$ and POLY$^2$ in Formulae V, Va, Vc, Vb, VI, VIa, VIc, VIb, VII, VIIa, VIIc, VIIb, VIII, VIIIa, VIIIc, VIIIb, IX, IXa, IXb, IXc, IXd, IXe, IXf and IXg include linear and branched. Exemplary first and second spacer moieties for each of Formulae V, Va, Vc, Vb, VI, VIa, VIc, VIb, VII, VIIa, VIIc, VIIb, VIII, VIIIa, VIIIc, VIIIb, IX, IXa, IXb, IXc, IXd, IXe, IXf and IXg include X$^1$ and X$^2$ spacer moieties independently selected from the group consisting of —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—, —O—CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—O—, —C(O)—NH—CH$_2$—CH$_2$—, —CH$_2$—CH$_2$—NH—C(O)—, —C(O)—NH—CH$_2$—CH$_2$—O—, and —O—CH$_2$—CH$_2$—NH—C(O)—. It is also preferred, with respect to Formulae V, Va, Vc, Vb, VI, VIa, VIc, VIb, VII, VIIa, VIIc, VIIb, VIII, VIIIa, VIIIc, VIIIb, IX, IXa, IXb, IXc, IXd, IXe, IXf and IXg that each of R$^1$ and R$^2$ is H, although lower alkyl (such as methyl and ethyl) is also contemplated. In addition, with respect to any electron altering groups present in any of Formulae V, Vc, Vb, VI, VIc, VIb, VII, VIIc, VIIb, VIII, VIIIc, VIIIb, IX, IXb, IXc, IXd, IXe, IXf and IXg each electron altering group is preferably halo, lower alkyl, aryl, substituted aryl, substituted arylakyl, alkoxy, aryloxy, alkylthio, arylthio, CF$_3$, —CH$_2$CF$_3$, —CH$_2$C$_6$F$_5$, —CN, —NO$_2$, —S(O)R, —S(O)Ar, —S(O$_2$)R, —S(O$_2$)Ar, —S(O$_2$)OR, —S(O$_2$)OAr, —S(O$_2$)NHR, —S(O$_2$)NHAr, —C(O)R, —C(O)Ar, —C(O)OR, —C(O)NHR, and the like, wherein Ar is aryl and R is H or an organic radical.

Another exemplary polymeric reagent has the following formula:

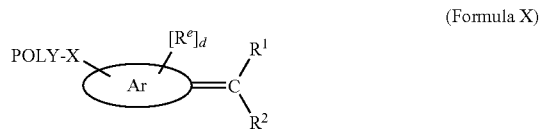

(Formula X)

wherein:
POLY is a water-soluble polymer;
X is a spacer moiety (that preferably does not include a

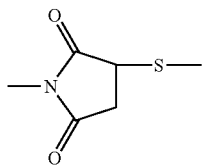

or

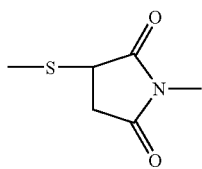

moiety);

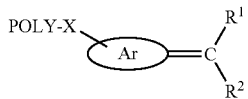

is an aromatic-containing moiety;
$R^1$ is H or an organic radical;
$R^2$ is H or an organic radical;
$R^e$ is an electron altering group; and
(d) is either zero or one.

Another exemplary polymeric reagent comprises the following structure:

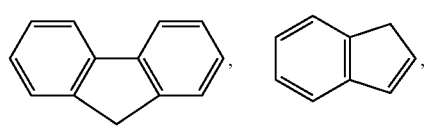
(Formula Xa)

wherein each of POLY, X, $R^1$ and $R^2$ is as previously defined with respect to Formula X.

The polymeric reagents corresponding to Formulae X and Xa will typically (although not necessarily) have POLY be a poly(alkylene oxide) such as a poly(ethylene glycol). Further, the poly(ethylene glycol) can be terminally capped with an end-capping moiety selected from the group consisting of hydroxyl, alkoxy, substituted alkoxy, alkenoxy, substituted alkenoxy, alkynoxy, substituted alkynoxy, aryloxy and substituted aryloxy. Preferred terminal capping groups, however, include methoxy. Exemplary weight average molecular weights for a poly(ethylene glycol) that serves as a POLY in Formulae X and Xa include one or more of the following: in the range of from about 120 Daltons to about 6,000 Daltons; in the range of from about 6,000 Daltons to about 100,000 Daltons; in the range of from about 10,000 Daltons to about 85,000 Daltons; and in the range of from about 20,000 Daltons to about 85,000 Daltons. Exemplary architectures for a poly(ethylene glycol) that serves as a POLY in Formulae X and Xa include linear and branched. Exemplary second spacer moieties for Formulae X and Xa include spacer moieties selected from the group consisting of —NH—C(O)—CH$_2$—, —CH$_2$—C(O)—NH—, —NH—C(O)—CH$_2$—O—, —O—CH$_2$—C(O)—NH—, —CH$_2$—CH$_2$—NH—C(O)—CH$_2$—CH$_2$—C(O)—NH—, —NH—C(O)—CH$_2$—CH$_2$—CH$_2$—C(O)—NH—CH$_2$—CH$_2$—, —O—CH$_2$—CH$_2$—NH—C(O)—CH$_2$—CH$_2$—CH$_2$—C(O)—NH—, —NH—C(O)—CH$_2$—CH$_2$—CH$_2$—C(O)—NH—CH$_2$—CH$_2$—O—, —C(O)—NH—CH$_2$—CH$_2$—, —CH$_2$—CH$_2$—NH—C(O)—, —C(O)—NH—CH$_2$—CH$_2$—O—, and —O—CH$_2$—CH$_2$—NH—C(O)—. With respect to Formulae X and Xa, each of $R^1$ and $R^2$ is preferably H although lower alkyl (such as methyl and ethyl) is also contemplated. With respect to Formula Xa, it is preferred that $R^e$ is halo, lower alkyl, aryl, substituted aryl, substituted arylakyl, alkoxy, aryloxy, alkylthio, arylthio, CF$_3$, —CH$_2$CF$_3$, —CH$_2$C$_6$F$_5$, —CN, —NO$_2$, —S(O)R, —S(O)Ar, —S(O$_2$)R, —S(O$_2$)Ar, —S(O$_2$)OR, —S(O$_2$)OAr, —S(O$_2$)NHR, —S(O$_2$)NHAr, —C(O)R, —C(O)Ar, —C(O)OR, —C(O)NHR, and the like, wherein Ar is aryl and R is H or an organic radical.

In some embodiments, it is preferred that the aromatic moiety for Formula X (and the corresponding conjugate represented by Formula X-C) is not one of the following:

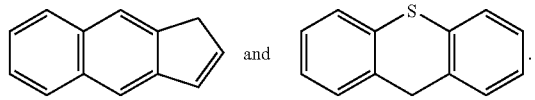

Examples of polymeric reagents of the invention include the following:

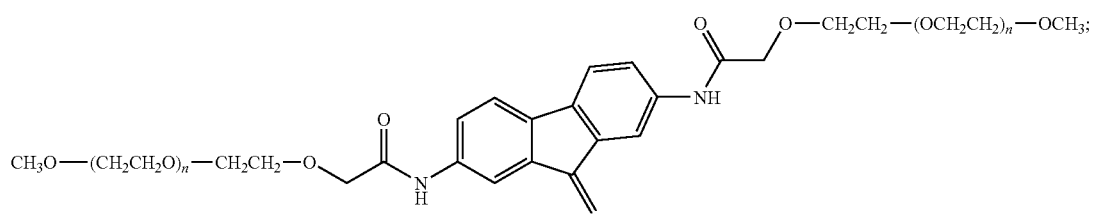

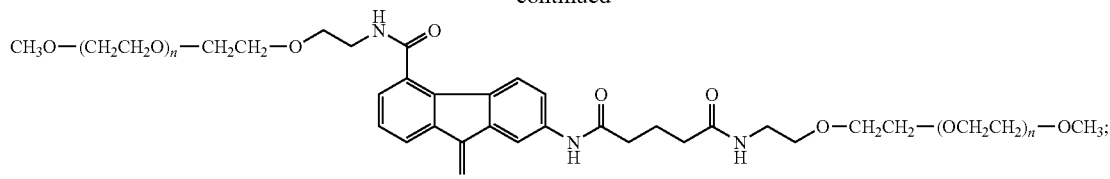

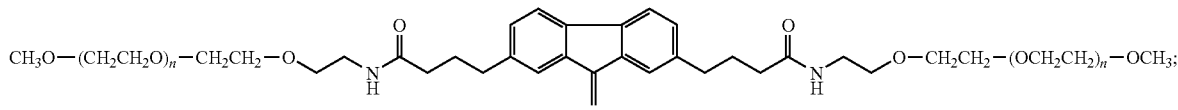

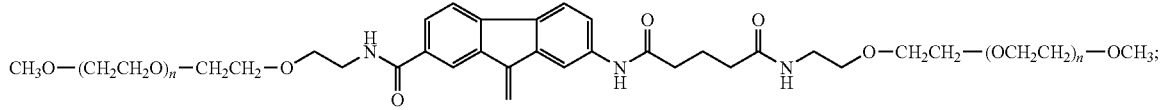

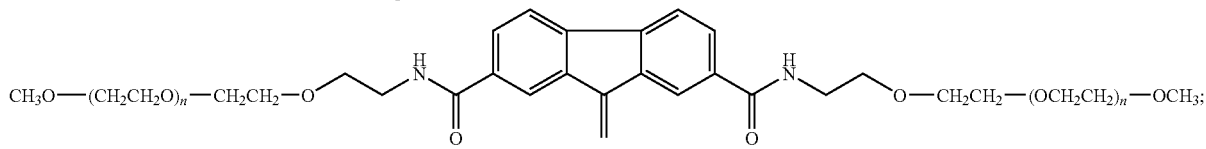

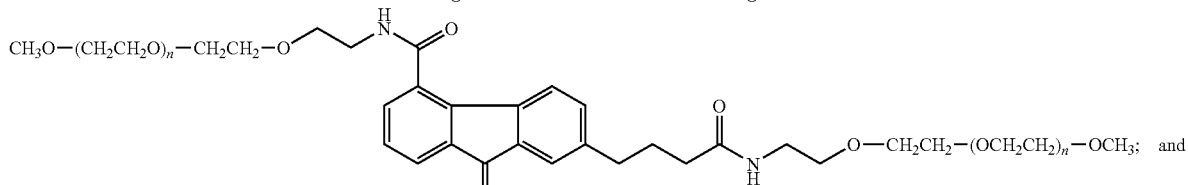

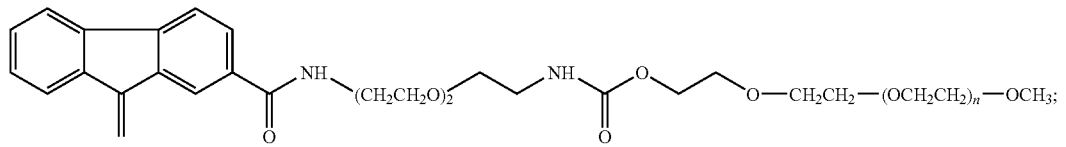

40 wherein each (n) is from 4 to 1500.

The polymeric reagents of the invention can be prepared in any number of ways. Consequently, the polymers provided herein are not limited to the specific technique or approach used in their preparation. Exemplary approaches for preparing the presently described polymer reagents, however, will be discussed in detail below In one method for preparing a polymeric reagent, the method comprises: (a) attaching to an aromatic-containing moiety bearing a first attachment site, a second attachment site and an optional third attachment site, in one or more steps, a vinylic functional group to the first attachment site; and (b) reacting a water-soluble polymer bearing a reactive group with the second attachment site and, when present, the optional third attachment site to result in (i) the second attachment site bearing a water-soluble polymer through a spacer moiety, and (ii) the optional third attachment site, when present, bearing a second water-soluble polymer through a spacer moiety, In some instances, (a) is performed before step (b) while in other instances, (b) is performed before step (a).

Thus, in this method for preparing a polymeric reagent, a required component is an aromatic-containing moiety bearing a first attachment site, a second attachment site and an optional third attachment site. An exemplary aromatic-containing moiety, for illustrative purposes, is shown below.

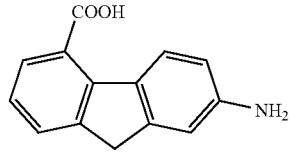

This aromatic-containing moiety, is an example of an aromatic-containing moiety having three attachment sites: a reactive methylene group at the 9 position, an amino group at 7 positions and a carboxylic acid. The aromatic-containing moiety can be provided in a base or salt form.

Having provided the aromatic-containing moiety, a step in the method broadly includes the step of attaching, in one or more steps, a vinylic functional group to the first attachment site. Here, it is possible to carry out the sequence of formylation, reduction, acetate formation, and elimination (preferably followed by ion exchange chromatography for recovery).

Another step in the method includes reacting a water-soluble polymer bearing a reactive group with the second attachment site and, when present, the optional third attachment site. Here, known methods can be used and the method is not limited to the specific approach. For example, an amine reactive PEG (such as an N-succinimidyl ester-terminated mPEG, formed, for example, from the reaction of N-hydroxysuccinimide and CH$_3$O—CH$_2$CH$_2$—(OCH$_2$CH$_2$)—OCH$_2$CH$_2$—OCH$_2$COOH with dicyclohexyl carbodiimide (DCC) or diisopropyl carbodiimide (DIC) as condensing agent and optionally in the presence of a base) can be reacted with amine bearing aromatic-containing moiety. Alternatively, benzotriazole carbonate-terminated mPEG (mPEG-BTC) can also be used to attach a water-soluble polymer to an amino group.

The steps of the method take place in an appropriate solvent. One of ordinary skill in the art can determine whether any specific solvent is appropriate for any given reaction. Typically, however, the solvent is preferably a nonpolar solvent or a polar aprotic solvent. Nonlimiting examples of nonpolar solvents include benzene, xylene, dioxane, tetrahydrofuran (THF), t-butyl alcohol and toluene. Particularly preferred nonpolar solvents include toluene, xylene, dioxane, tetrahydrofuran, and t-butyl alcohol. Exemplary polar aprotic solvents include, but are not limited to, DMSO (dimethyl sulfoxide), HMPA (hexamethylphosphoramide), DMF (dimethylformamide), DMA (dimethylacetamide), NMP (N-methylpyrrolidinone).

The sulfonyl groups attached to each ring, being highly electronegative groups, can influence the rates of conjugation and release. Hence, the drug release rates of these conjugates would be relatively fast Electron altering groups may be added in one or more additional steps. For example, aromatic nitration by combining nitric acid in the presence of sulfuric acid results in a nitro group (i.e., —NO$_2$) being attached to the aromatic system. In addition, halogenation methods such as combining the aromatic system with a halogen in the present of a metal catalyst (such as iron) results in a halo group being attached to the aromatic system. With regard to halogenation methods wherein a metal ion is present, it is preferred (for reasons explained herein) to first carry out the step of adding the halo group to the aromatic system and subsequently remove any metal ions and then attach one or more water-soluble polymers to the aromatic system. Further, alkylation and acylation methods such as a Friedel-Crafts reaction can be used to add an electron altering alkyl or acyl group (respectively) to the aromatic system by adding an alkyl halide (e.g., isobutyl chloride) or acyl halide (e.g., propionyl chloride) to the aromatic system in the presence of a metal catalyst (such as aluminum). Again, because a metal catalyst is typically required to carry out such reactions, it is preferred to first carry out the step of adding the alkyl group to the aromatic system and subsequently remove any metal ions and then attach one or more water-soluble polymers to the aromatic system.

During preparation and handling of the polymeric reagents (as well the preparation and handling of the corresponding conjugates), it is preferred to prevent the introduction of metal ions. For example, because metal ions are well known to be coordinated by PEGs, the avoidance of metal ions is preferred. In addition, metal ions are known to catalyze PEG chain oxidation. In particular, when PEG is attached to an electron rich aromatic system, the presence of a metal ion coordinated to the PEG chain may provide a route for electron transfer from the aromatic nucleus to the PEG-metal ion complex and facilitate PEG chain cleavage. Thus, the invention includes methods and compositions wherein metal ions are substantially absent.

These and other approaches for preparing the polymeric reagents described herein can be used.

Once prepared, the polymeric reagents can be isolated. Known methods can be used to isolate the polymeric reagent, but it is particularly preferred to use chromatography, e.g., size exclusion chromatography. Alternately or in addition, the method includes the step of purifying the polymeric reagent once it is formed. Again, standard art-known purification methods can be used to purify the polymeric reagent.

The polymeric reagents of the invention are sensitive to moisture and oxygen and are ideally stored under an inert atmosphere, such as under argon or under nitrogen, and at low temperature. In this way, potentially degradative processes associated with, for example, atmospheric oxygen, are reduced or avoided entirely. In some cases, to avoid oxidative degradation, antioxidants, such as butylated hydroxyl toluene (BHT), can be added to the polymeric reagent prior to storage. In addition, it is preferred to minimize the amount of moisture associated with the storage conditions to reduce potentially damaging reactions associated with water. Moreover, it is preferred to keep the storage conditions dark in order to prevent certain degradative processes that involve light. Thus, preferred storage conditions include one or more of the following: storage under dry argon or another dry inert gas; storage at temperatures below about −15° C.; storage in the absence of light; and storage with a suitable amount (e.g., about 50 to about 500 parts per million) of an antioxidant such as BHT.

The above-described polymeric reagents are useful for conjugation to biologically active agents. For example, a thiol group (e.g., —SH) on an active agent will react with the vinylic functional group to form a degradable linkage. Thus, the invention comprises a conjugate formed with any polymeric reagent described herein. For each of the conjugates shown below, the nucleophile of the active agent is a thiol to thereby provide a thioether bond. It will be appreciated that other nucleophiles work suffice as well.

Exemplary conjugates include those of the following formula:

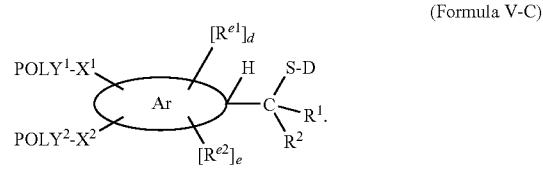

(Formula V-C)

wherein:
POLY$^1$ is a first water-soluble polymer;
POLY$^2$ is a second water-soluble polymer;
X$^1$ is a first spacer moiety;
X$^2$ is a second spacer moiety;

Ar is an aromatic-containing moiety;
R$^1$ is H or an organic radical;
R$^2$ is H or an organic radical;
(d) is either zero or one;
(e) is either zero or one;
R$^{e1}$, when present, is a first electron altering group;
R$^{e2}$, when present, is a second electron altering group; and
D is a residue of a thiol-containing biologically active agent. Conjugates corresponding to this Formula V-C can be prepared using polymeric reagents corresponding to Formula I.

When the conjugate corresponding to Formula V-C has no discrete electron altering groups [i.e., when (d) and (e) are both zero with regard to Formula V-C], a conjugate of the following formula results:

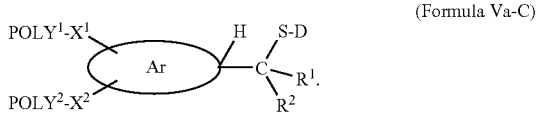
(Formula Va-C)

wherein each of POLY$^1$, POLY$^2$, X$^1$, X$^2$ $\bigcirc$ Ar $\bigcirc$,

R$^1$, R$^2$, and D is as previously defined with respect to Formula V-C. Conjugates corresponding to this Formula Va-C can be prepared using polymeric reagents corresponding to Formula Va.

When the conjugate corresponding to Formula V-C has a single discrete electron altering group [e.g., when (d) is one and (e) is zero with regard to Formula V-C], a conjugate of the following formula results:

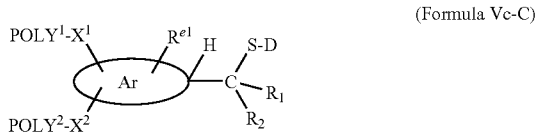
(Formula Vc-C)

wherein each of POLY$^1$, POLY$^2$, X$^1$, X$^2$, $\bigcirc$ Ar $\bigcirc$,

R$^1$, R$^2$, D and R$^{e1}$ is as previously defined with respect to Formula V-C. Conjugates corresponding to this Formula Vc-C can be prepared using polymeric reagents corresponding to Formula Vc.

When the conjugate corresponding to Formula V-C has two discrete electron altering groups [i.e., when (d) and (e) are both one with regard to Formula V-C], a conjugate of the following formula results:

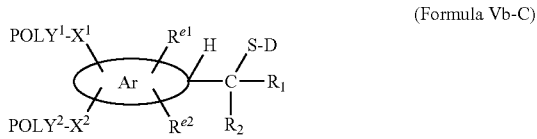
(Formula Vb-C)

wherein each of POLY$^1$, POLY$^2$, X$^1$, X$^2$, R$^1$, R$^2$, $\bigcirc$ Ar $\bigcirc$, D, R$^{e1}$ and R$^{e2}$ is as previously defined with respect to Formula I-C. Conjugates corresponding to this Formula Vb-C can be prepared using polymeric reagents corresponding to Formula Vb.

In some cases, the conjugate can include individual aromatic moieties that are only linked to each other through a carbon atom. Such a conjugate has the following formula:

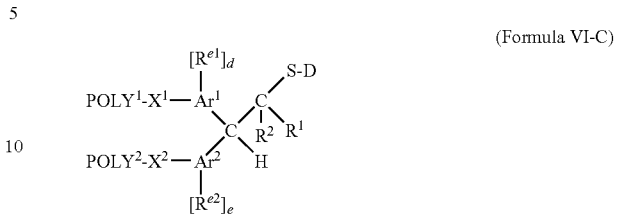
(Formula VI-C)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group;
R$^{e2}$, when present, is a second electron altering group; and
D is a residue of a thiol-containing biologically active agent. Conjugates corresponding to this Formula VI-C can be prepared using polymeric reagents corresponding to Formula VI.

When the conjugate corresponding to Formula VI-C has no discrete electron altering groups [i.e., when (d) and (e) are both zero with regard to Formula VI-C], a conjugate of the following formula results:

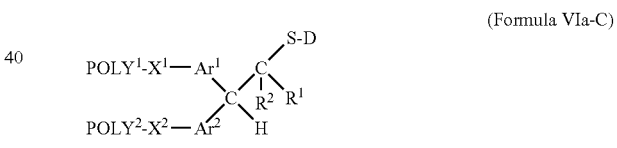
(Formula VIa-C)

wherein each of POLY$^1$, POLY$^2$, X$^1$, X$^2$, R$^1$, R$^2$, Ar$^1$, Ar$^2$ and D is as previously defined with respect to Formula II-C. Conjugates corresponding to this Formula VIa-C can be prepared using polymeric reagents corresponding to Formula VIa.

When the conjugate corresponding to Formula VI has a single discrete electron altering group [e.g., when (d) is one and (e) is zero with regard to Formula VI], a conjugate of the following formula results:

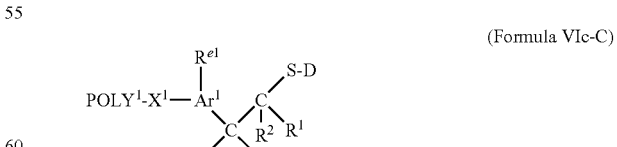
(Formula VIc-C)

wherein each of POLY$^1$, POLY$^2$, X$^1$, X$^2$, Ar$^1$, Ar$^2$, H$_\alpha$, R$^1$, R$^2$, R$^{e1}$ and D is as previously defined with respect to Formula VI-C. Conjugates corresponding to this Formula VIc-C can be prepared using polymeric reagents corresponding to Formula VIc.

When the conjugate corresponding to Formula VI-C has two discrete electron altering groups [i.e., when (d) and (e) are both one with regard to Formula VI-C], a conjugate of the following formula results:

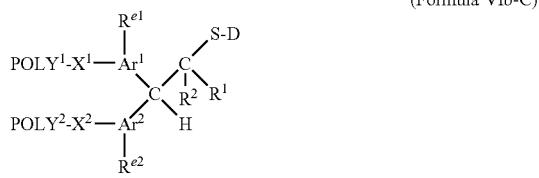

(Formula VIb-C)

wherein each of POLY$^1$, POLY$^2$, X$^1$, X$^2$, Ar$^1$, Ar$^2$, H, R$^1$, R$^2$, D, R$^{e1}$ and R$^{e2}$ is as previously defined with respect to Formula VI-C. Conjugates corresponding to this Formula VIb-C can be prepared using polymeric reagents corresponding to Formula VIb.

In still other cases, the conjugate can include individual aromatic moieties that are linked to each other both through a carbon atom as well as another direct bond. Such a conjugate has the following formula:

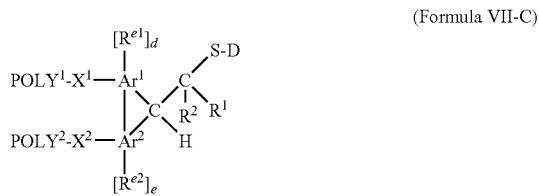

(Formula VII-C)

wherein:
POLY$^1$ is a first water-soluble polymer;
POLY$^2$ is a second water-soluble polymer;
X$^1$ is a first spacer moiety;
X$^2$ is a second spacer moiety;
Ar$^1$ is a first aromatic moiety;
Ar$^2$ is a second aromatic moiety;
R$^1$ is H or an organic radical;
R$^2$ is H or an organic radical;
(d) is either zero or one;
(e) is either zero or one;
R$^{e1}$, when present, is a first electron altering group;
R$^{e2}$, when present, is a second electron altering group; and
D is a residue of a thiol-containing biologically active agent. Conjugates corresponding to this Formula VII-C can be prepared using polymeric reagents corresponding to Formula VII.

When the conjugate corresponding to Formula VII-C has no discrete electron altering groups [i.e., when (d) and (e) are both zero with regard to Formula VII-C], a conjugate of the following formula results:

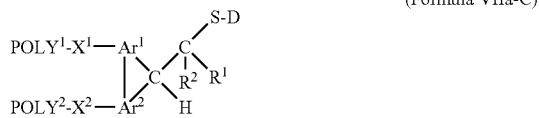

(Formula VIIa-C)

wherein each of POLY$^1$, POLY$^2$, X$^1$, X$^2$, R$^1$, R$^2$, Ar$^1$, Ar$^2$ and D is as previously defined with respect to Formula VII-C.

Conjugates corresponding to this Formula VIIa-C can be prepared using polymeric reagents corresponding to Formula VIIa.

When the conjugate corresponding to Formula VII-C has a single discrete electron altering group [e.g., when (d) is one and (e) is zero with regard to Formula VII-C], a conjugate of the following formula results:

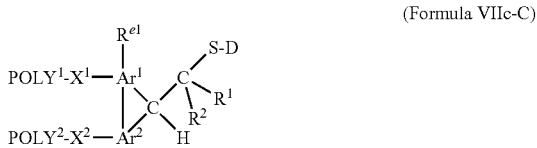

(Formula VIIc-C)

wherein each of POLY$^1$, POLY$^2$, X$^1$, X$^2$, R$^1$, R$^2$, Ar$^1$, Ar$^2$, R$^{e1}$, Y$^1$, Y$^2$ and D is as previously defined with respect to Formula VII-C. Conjugates corresponding to this Formula VIIc-C can be prepared using polymeric reagents corresponding to Formula VIc.

When the conjugate corresponding to Formula VII-C has two discrete electron altering groups [i.e., when (d) and (e) are both one with regard to Formula VII-C], a conjugate of the following formula results:

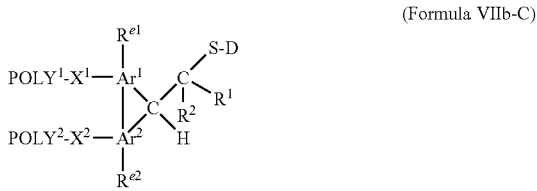

(Formula VIIb-C)

wherein each of POLY$^1$, POLY$^2$, X$^1$, X$^2$, R$^1$, R$^2$, Ar$^1$, Ar$^2$, R$^{e1}$, R$^{e2}$ and D is as previously defined with respect to Formula VII-C. Conjugates corresponding to this Formula VIIb-C can be prepared using polymeric reagents corresponding to Formula VIIb.

In still other cases, the conjugate can include individual aromatic moieties that are linked to each other both through a carbon atom as well as a spacer moiety of one or more atoms. Such a conjugate has the following formula:

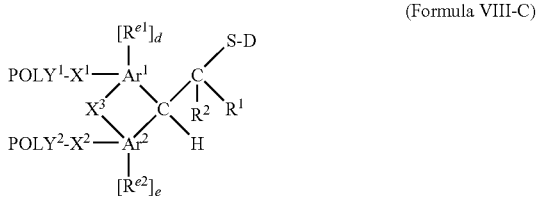

(Formula VIII-C)

wherein:
POLY$^1$ is a first water-soluble polymer;
POLY$^2$ is a second water-soluble polymer;
X$^1$ is a first spacer moiety;
X$^2$ is a second spacer moiety;
X$^3$ is a third spacer moiety;
Ar$^1$ is a first aromatic moiety;
Ar$^2$ is a second aromatic moiety;
R$^1$ is H or an organic radical;
R$^2$ is H or an organic radical;

(d) is either zero or one;

(e) is either zero or one;

$R^{e1}$, when present, is a first electron altering group;

$R^{e2}$, when present, is a second electron altering group; and

D is a residue of a thiol-containing biologically active agent. Conjugates corresponding to this Formula VIII-C can be prepared using polymeric reagents corresponding to Formula VIII.

When the conjugate corresponding to Formula VIII-C has no discrete electron altering groups [i.e., when (d) and (e) are both zero with regard to Formula VIII-C], a conjugate of the following formula results:

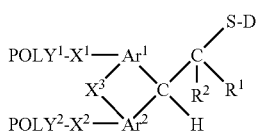

(Formula VIIIa-C)

wherein each of $POLY^1$, $POLY^2$, $X^1$, $X^2$, $X^3$, $R^1$, $R^2$, $Ar^1$, $Ar^2$ and D is as previously defined with respect to Formula VIII-C. Conjugates corresponding to this Formula VIIIa-C can be prepared using polymeric reagents corresponding to Formula VIIIa.

When the conjugate corresponding to Formula VIII-C has a single discrete electron altering group [e.g., when (d) is one and (e) is zero with regard to Formula VIII-C], a conjugate of the following formula results:

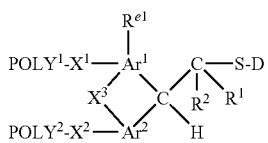

(Formula VIIIc-C)

wherein each of $POLY^1$, $POLY^2$, $X^1$, $X^2$, $X^3$, $R^1$, $R^2$, $Ar^1$, $Ar^2$, $R^{e1}$ and D is as previously defined with respect to Formula VIII-C. Conjugates corresponding to this Formula VIIIc-C can be prepared using polymeric reagents corresponding to Formula VIIIc.

When the conjugate corresponding to Formula VIII-C has two discrete electron altering groups [i.e., when (d) and (e) are both one with regard to Formula VIII-C], a conjugate of the following formula results:

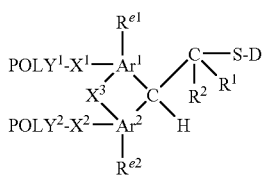

(Formula VIIIb-C)

wherein each of $POLY^1$, $POLY^2$, $X^1$, $X^2$, $X^3$, $Ar^1$, $Ar^2$, $R^1$, $R^2$, $R^{e1}$, $R^{e2}$ and D is as previously defined with respect to Formula VIII-C. Conjugates corresponding to this Formula VIIIb-C can be prepared using polymeric reagents corresponding to Formula VIIIb.

A preferred conjugate comprises the following structure:

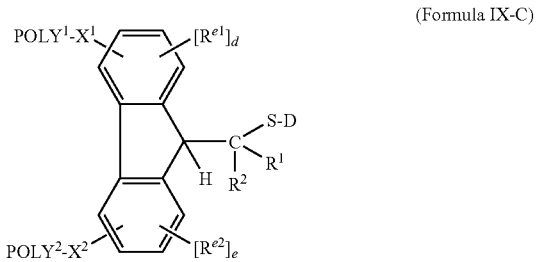

(Formula IX-C)

wherein:

$POLY^1$ is a first water-soluble polymer;

$POLY^2$ is a second water-soluble polymer;

$X^1$ is a first spacer moiety;

$X^2$ is a second spacer moiety;

$R^1$ is H or an organic radical;

$R^2$ is H or an organic radical;

(d) is either zero or one;

(e) is either zero or one;

$R^{e1}$, when present, is a first electron altering group;

$R^{e2}$, when present, is a second electron altering group; and

D is a residue of a thiol-containing biologically active agent. Conjugates corresponding to this Formula IX-C can be prepared using polymeric reagents corresponding to Formula IX.

When the conjugate corresponding to Formula IX-C has no discrete electron altering groups [i.e., when (d) and (e) are both zero with regard to Formula IX-C], a conjugate of the following formula results:

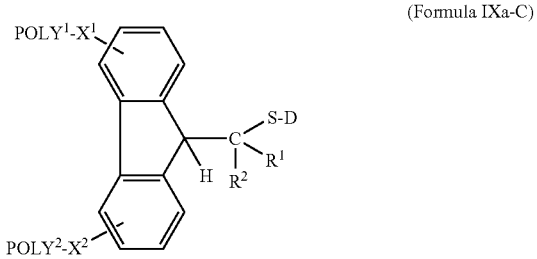

(Formula IXa-C)

wherein each of $POLY^1$, $POLY^2$, $X^1$, $X^2$, $R^1$, $R^2$ and D is as previously defined with respect to Formula IX-C. Conjugates corresponding to this Formula IXa-C can be prepared using polymeric reagents corresponding to Formula IXa.

When the conjugate corresponding to Formula IX-C has a single discrete electron altering group [e.g., when (d) is one and (e) is zero with regard to Formula IX-C], a conjugate of the following formula results:

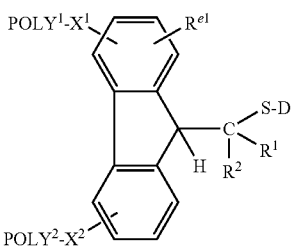
(Formula IXc-C)

wherein each of POLY$^1$, POLY$^2$, X$^1$, X$^2$, R$^1$, R$^2$, R$^{e1}$ and D is as previously defined with respect to Formula IX-C. Conjugates corresponding to this Formula IXc-C can be prepared using polymeric reagents corresponding to Formula IXc.

When the conjugate corresponding to Formula IX-C has two discrete electron altering groups [i.e., when (d) and (e) are both one with regard to Formula IX-C], a conjugate of the following formula results:

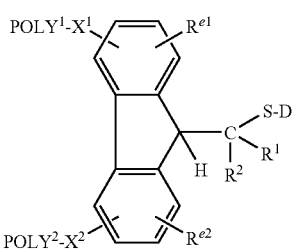
(Formula IXb-C)

wherein each of POLY$^1$, POLY$^2$, X$^1$, X$^2$, R$^1$, R$^2$, R$^{e1}$, R$^{e2}$ and D is as previously defined with respect to Formula IX-C. Conjugates corresponding to this Formula IXb-C can be prepared using polymeric reagents corresponding to Formula IXb.

Still another preferred conjugate is of the following structure:

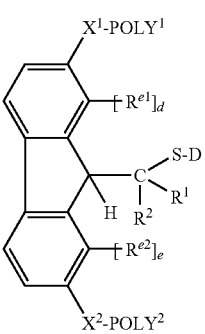
(Formula IXd-C)

wherein each of POLY$^1$, POLY$^2$, X$^1$, X$^2$, R$^1$, R$^2$, R$^{e1}$, R$^{e2}$, (d), (e) and D is as previously defined with respect to Formula IX-C, with the proviso that R$^{e1}$ is H when (d) is zero and R$^{e2}$ is H when (e) is zero. Conjugates corresponding to this Formula IXd-C can be prepared using polymeric reagents corresponding to Formula IXd.

Still another preferred conjugate is of the following structure:

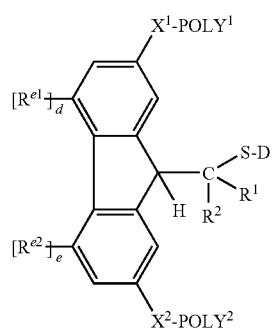
(Formula IXe-C)

wherein each of POLY$^1$, POLY$^2$, X$^1$, X$^2$, R$^1$, R$^2$, R$^{e1}$, R$^{e2}$ and D is as previously defined with respect to Formula IX-C, with the proviso that R$^{e1}$ is H when (d) is zero and R$^{e2}$ is H when (e) is zero. Conjugates corresponding to this Formula IXe-C can be prepared using polymeric reagents corresponding to Formula IXe.

Still another preferred conjugate is of the following structure:

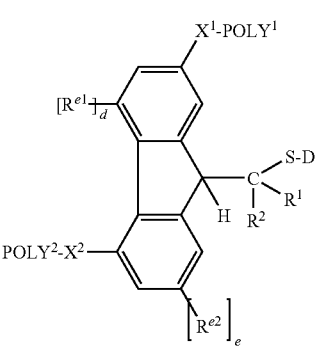
(Formula IXf-C)

wherein each of POLY$^1$, POLY$^2$, X$^1$, X$^2$, R$^1$, R$^2$, R$^{e1}$, R$^{e2}$, (d), (e) and D is as previously defined with respect to Formula IX-C, with the proviso that R$^{e1}$ is H when (d) is zero and R$^{e2}$ is H when (e) is zero. Conjugates corresponding to this Formula IXf-C can be prepared using polymeric reagents corresponding to Formula IXf.

Still another preferred conjugate is of the following structure:

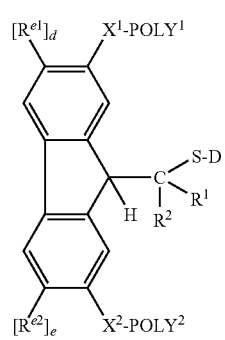
(Formula IXg-C)

wherein each of POLY$^1$, POLY$^2$, X$^1$, X$^2$, R$^1$, R$^2$, R$^{e1}$, R$^{e2}$, (d), (e) and D is as previously defined with respect to Formula IX-C, with the proviso that $R^{e1}$ is H when (d) is zero and $R^{e2}$ is H when (e) is zero. Conjugates corresponding to this Formula IXg-C can be prepared using polymeric reagents corresponding to Formula IXg.

Another exemplary conjugate of the invention has the following formula:

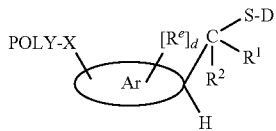
(Formula X-C)

wherein:
POLY is a water-soluble polymer;
X is a spacer moiety (that preferably does not include a

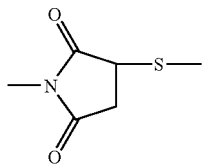

or

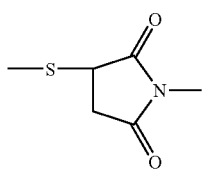

moiety);

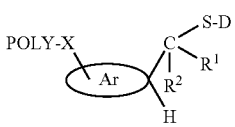

is an aromatic moiety;
$R^1$ is H or an organic radical;
$R^2$ is H or an organic radical;
$R^e$ is an electron altering group;
(d) is either zero or one; and
D is a residue of a thiol-containing biologically active agent. Conjugates corresponding to this Formula X-C can be prepared using polymeric reagents corresponding to Formula X.

Another exemplary conjugate comprises the following structure:

(Formula Xa-C)

wherein each of POLY, X, $R^1$, $R^2$, $Y^1$, $Y^2$ and D is as previously defined with respect to Formula X. Conjugates corresponding to this Formula Xa-C can be prepared using polymeric reagents corresponding to Formula Xa.

Examples of conjugates of the invention include:

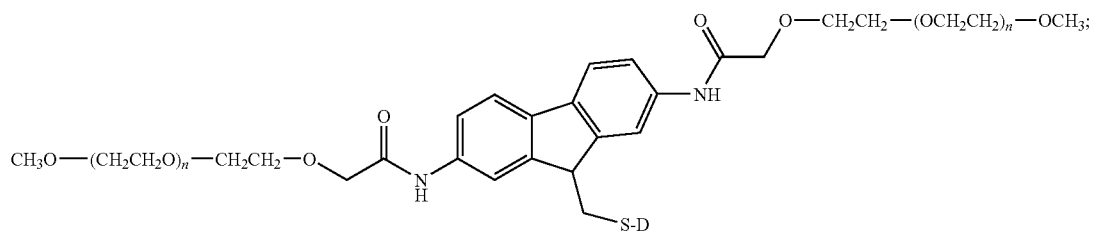

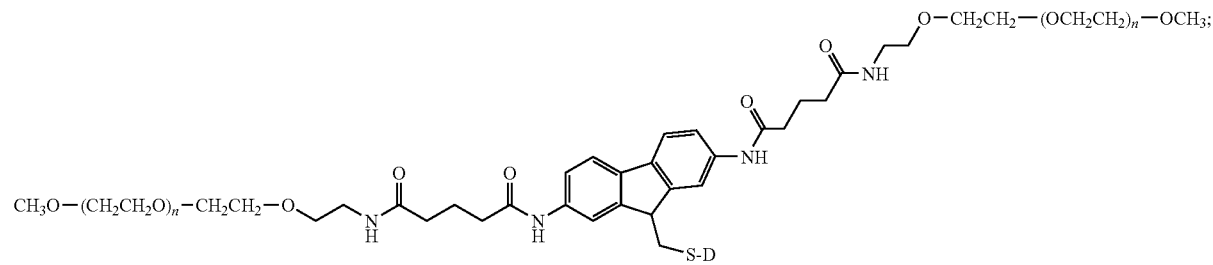

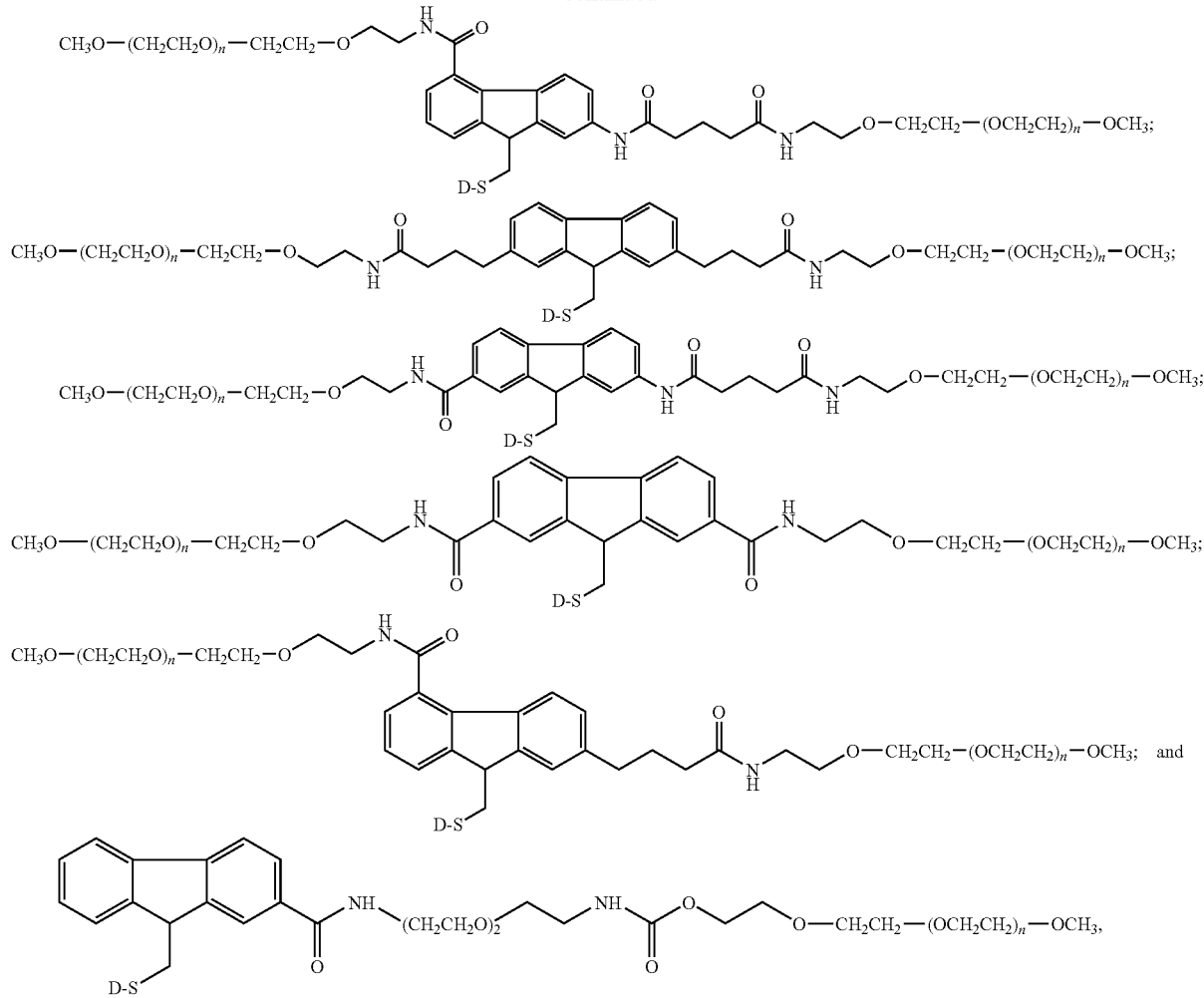

wherein each (n) is from 4 to 1500.

The biologically active agent to which a polymeric reagent as described herein can be conjugated, is a nucleophile-containing biologically active agent (such as an amine- or thiol containing biologically active agent). In some embodiments, the biologically active agent will be a small molecule (e.g., a biologically active agent that has a molecular weight of less than about 3,500 Daltons. In other embodiments, the biologically active agent will be a macromolecule, such as a polypeptide, having a molecular weight greater than about 3,500 Daltons. Pharmacologically active polypeptides represent a preferred type of biologically active agent. It should be understood that for purposes of the present discussion, the term "polypeptide" will be generic for oligopeptides and proteins.

The invention also provides for a method of preparing a conjugate comprising the step of contacting a polymeric reagent of the invention with a biologically active agent under conditions suitable to form a covalent attachment between the polymer and the biologically active agent. Typically, the polymer is added to the active agent or surface at an equimolar amount (with respect to the desired number of groups suitable for reaction with the reactive group) or at a molar excess. For example, the polymeric reagent can be added to the target active agent at a molar ratio of about 1:1 (polymeric reagent: active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture preferably undergoes a process to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

With respect to polymer-active agent conjugates, the conjugates can be separated to obtain/isolate different conjugated species. Alternatively, and more preferably for lower molecular weight (e.g., less than about 20 kiloDaltons, more preferably less than about 10 kiloDaltons) polymers, the product mixture can be separated to obtain the distribution of water-soluble polymer segments per active agent. For example, the product mixture can be separated to obtain an average of anywhere from one to five PEGs per active agent (e.g., polypeptide). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100 kDa protein is randomly conjugated to a polymeric reagent having a molecular weight of about 20 kDa, the resulting reaction mixture will likely contain unmodified protein (MW 100 kDa), mono-PEGylated protein (MW 120 kDa), di-PEGylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content [Sims et al. (1980) *Anal. Biochem,* 107:60-63], and (iv) sodium dodecyl sulfphate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

Following conjugation, and optionally additional separation steps, the conjugate mixture can be concentrated, sterile filtered, and stored at a low temperature, typically from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized powder is absent residual buffer. Alternatively, a buffer exchange step may be used employing a formulation buffer, so that the lyophilized conjugate is in a form suitable for reconstitution into a formulation buffer and ultimately for administration to a mammal.

The polymeric reagents and conjugates are preferably in the form of a dry composition, meaning that there is less than 5% water in the composition. In addition the polymeric reagents and conjugates are preferably in the solid form.

A biologically active agent for use in coupling to a polymer as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are hereby incorporated by reference in their entireties.

EXPERIMENTAL

The practice of the invention will employ, unless otherwise indicated, conventional techniques of organic synthesis and the like, which are understood by one of ordinary skill in the art and are explained in the literature. In the following examples, efforts have been made to ensure accuracy with respect to numbers used (e.g., amounts, temperatures, and so forth), but some experimental error and deviation should be accounted for. Unless otherwise indicated, temperature is in degrees Celsius and pressure is at or near atmospheric pressure at sea level. Unless specified, all chemical reagents may be obtained from commercial suppliers. All generated NMR was obtained from a 300 or 400 MHz NMR spectrometer manufactured by Bruker (Billerica, Mass.). All processing is carried out in glass or glass-lined vessels and contact with metal-containing vessels or equipment is avoided.

FMOC 9-fluorenylmethoxycarbonyl
HCl hydrochloric acid
HEPES 4-(2-hydroxyethyl)-1-piperazineethanesulfonic acid
NMR Nuclear Magnetic Resonance
DCC 1,3-dicyclohexylcarbodiimide
DMF dimethylformamide
DMSO dimethyl sulfoxide
MW molecular weight
K or kDa kiloDaltons
HPLC High Performance Liquid Chromatography
THF tetrahydrofuran

Example 1

Preparation of 4-(mPEG$_{10,000Da}$-carboxyamide)-7-(mPEG$_{10,000Da}$ amidoglutaric amide)dibenzofulvene (or 4,7-CG-PEG2-fulvene 20K, or CG-PEG2-fulvene 20K)

4-(mPEG$_{10,000Da}$-carboxyamide)-7-(mPEG$_{10,000Da}$ amidoglutaricamide) dibenzofulvene was prepared in accordance with the reaction scheme provided below.

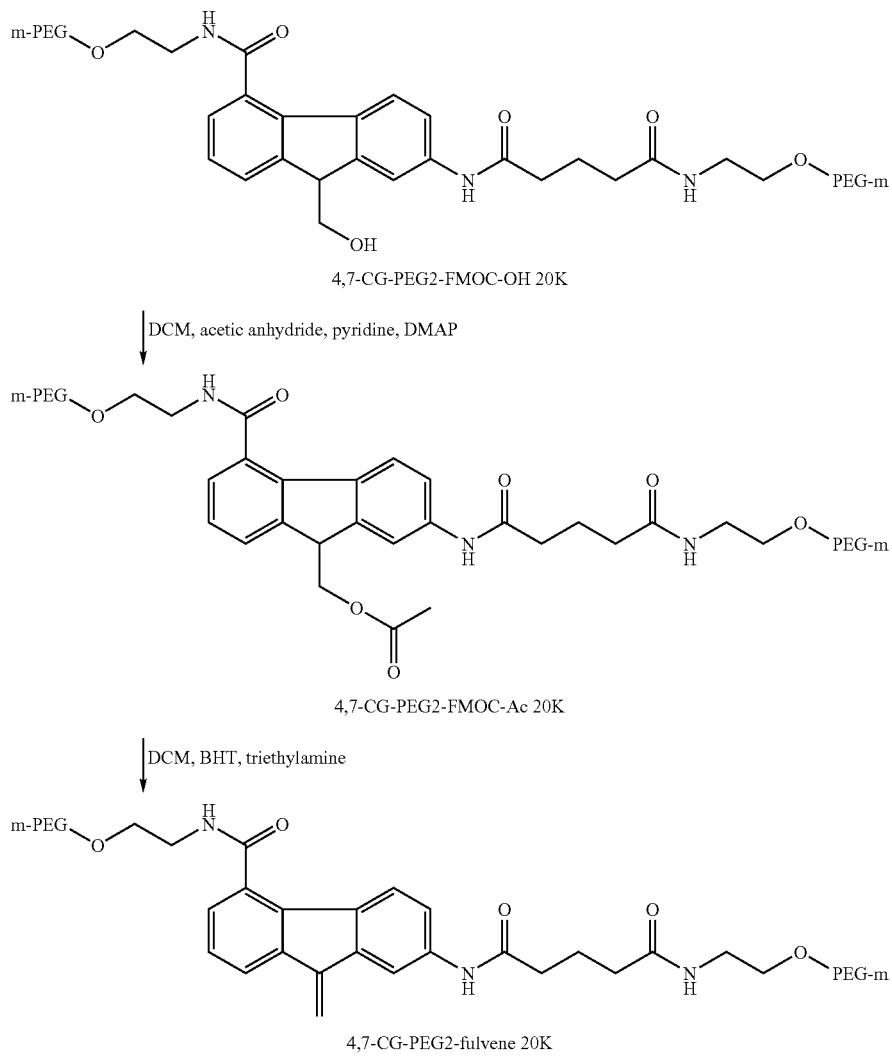

The synthesis was started with a sufficient amount of 9-hydroxymethyl-4-(mPEG$_{10,000Da}$)-7-(mPEG$_{10,000Da}$ amidoglutaric amide)fluorene, prepared in accordance with the procedure described in U.S. Patent Application Publication No. 2006/0293499 [referred therein as "9-hydroxymethyl-4-(mPEG(10,000)-carboxyamide)-7-(mPEG10,000) amidoglutaric amide)fluorene"].

Step 1. Preparation of 9-acetoxymethyl-4-(mPEG$_{10,000Da}$)-7-(mPEG$_{10,000Da}$ amidoglutaric amide)fluorene (or 4,7-CG-PEG2-FMOC-Ac 20K, or CG-PEG2-FMOC-Ac 20K)

9-Hydroxymethyl-4-(mPEG$_{10,000Da}$)-7-(mPEG$_{10,000Da}$ amidoglutaric amide)fluorene (5.5 g, 0.28 mmol) was dissolved in anhydrous dichloromethane (55 mL). Acetic anhydride (10 eq., 2.8 mmol, 0.27 mL), anhydrous pyridine (5 eq., 1.4 mmol, 0.12 mL) and 4-(dimethylamino)pyridine were added while stirring. The reaction was reacted at room temperature for four hours. The solvent was removed at reduced pressure and then the product mixture was dissolved in warm anhydrous isopropanol (100 mL). The polymer was precipitated by addition of anhydrous diethyl ether (100 mL) and cooling. The product was filtered, washed with additional diethyl ether and residual solvents removed under vacuum. Yield was 5.2 g, 95%, off-white powder. $^1$H-NMR (CD$_2$Cl$_2$): δ (ppm) 8.8 (1H, s, NH); 8.2 (1H, s, Ar); 7.9 (1H, d, Ar); 7.7 (1H, d, Ar); 7.4 (2H, m, Ar); 7.3 (1H, m, Ar); 6.7 (1H, bs, NH); 6.4 (1H, bs, NH); 4.4 (2H, m, CH$_2$); 4.2 (1H, m, CH); 3.6 (s, PEG backbone); 3.3 (6H, s, —OCH$_3$); 2.5 (2H, t, CH$_2$); 2.3 (2H, t, CH$_2$); 2.2 (3H, S, CH$_3$) 2.0 (2H, m, CH$_2$).

Step 2. Preparation of 4-(mPEG$_{10,000Da}$-carboxyamide)-7-(mPEG$_{10,000Da}$ amidoglutaric amide)dibenzofulvene (or 4,7-CG-PEG2-fulvene 20K, or CG-PEG2-fulvene 20K)

9-Acetoxymethyl-4-(mPEG$_{10,000Da}$)-7-(mPEG$_{10,000Da}$ amidoglutaric amide)fluorene (5.0 g, 0.25 mmol) was dissolved in anhydrous dichloromethane ("DCM," 120 mL). 2,6-Di-tert-butyl-4-methylphenol ("BHT," 50 mg) and triethylamine (15 mL) were added to the solution. The reaction was stirred at 21° C. for 29 hours. The solvent was removed at reduced pressure and then the product mixture was dissolved in warm anhydrous isopropanol (175 mL). The polymer was precipitated by slow addition of anhydrous diethyl ether (75 mL) and cooling. The product was filtered, washed with additional isopropanol and diethyl ether (containing BHT 4.5 mg) then residual solvents removed under vacuum. The dissolution and precipitation of product was repeated. Yield was 4.4 g, 88%, off-white to pale yellow powder. $^1$H-NMR (CD$_2$Cl$_2$): δ (ppm) 8.8 (1H, s, NH); 8.3 (1H, s, Ar); 7.8 (2H, dd, Ar); 7.4 (2H, m, Ar); 7.3 (1H, m, Ar); 6.7 (1H, bs, NH); 6.5 (1H, bs, NH); 6.1 (2H, d, CH$_2$); 3.6 (s, PEG backbone); 3.3 (6H, s, —OCH$_3$); 2.5 (2H, t, CH$_2$); 2.3 (2H, t, CH$_2$); 2.0 (2H, m, CH$_2$).

Another polymeric reagent was prepared using this same approach except mPEG-NH$_2$ (prepared in high purity using conventional methods) having a weight average molecular weight of 20,000 Da was substituted for mPEG-NH$_2$ (10,000 Da) in the preparation of 9-hydroxymethyl-4-(mPEG$_{10,000Da}$)-7-(mPEG$_{10,000Da}$ amidoglutaric amide)fluorene. The resulting polymeric reagent had a total molecular weight of about 40,000 Daltons.

Example 2

Preparation of 2,7-di(mPEG$_{10,000Da}$-amidoglutaric amide)dibenzofulvene (or 2,7-G2-PEG2-fulvene 20K, or G2-PEG2-fulvene 20K)

2,7-di(mPEG$_{10,000Da}$-amidoglutaric amide)dibenzofulvene was prepared in accordance with the reaction scheme provided below.

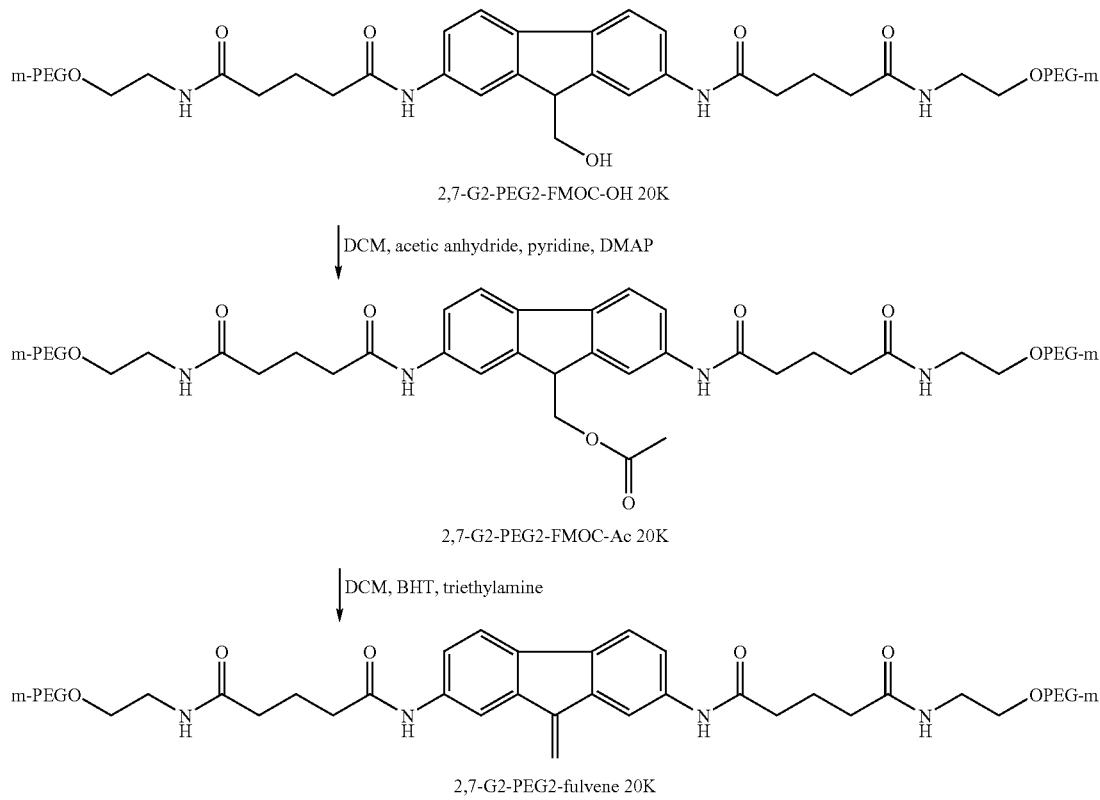

The synthesis was started with up to 225 g of 9-hydroxymethyl-2,7-di(mPEG$_{10,000Da}$-amidoglutaric amide)fluorene, prepared in accordance with the procedure described in U.S. Patent Application Publication No. 2006/0293499. From this, the corresponding 9-acetoxymethyl derivative was prepared following the general procedure set forth in Step 1, Example 1, described above. 9-Acetoxymethyl-2,7-di(mPEG$_{10,000Da}$-amidoglutaric amide)fluorene (or 2,7-G2-PEG2-FMOC-Ac 20K, or G2-PEG2-FMOC-Ac 20K) was prepared and was an off-white powder. $^1$H-NMR (CD$_2$Cl$_2$): δ (ppm) 8.8 (2H, s, NH); 8.0 (2H, s, Ar); 7.6 (2H, m, Ar); 7.5 (2H, m, Ar); 6.4 (2H, bs, NH); 4.3 (2H, m, CH$_2$); 4.2 (1H, t, CH); 3.6 (s, PEG backbone); 3.3 (6H, s, —OCH$_3$); 2.4 (4H, t, CH$_2$); 2.3 (4H, t, CH$_2$); 2.1 (3H, s, CH$_3$) 2.0 (4H, m, CH$_2$).

Next, 9-acetoxymethyl-2,7-di(mPEG$_{10,000Da}$-amidoglutaric amide)fluorene was converted to 2,7-di(mPEG$_{10,000Da}$-amidoglutaric amide)dibenzofulvene (or 2,7-G2-PEG2-fulvene 20K, or G2-PEG2-fulvene 20K) following the general procedure set forth in Step 2, Example 1, described above. 2,7-di(mPEG$_{10,000Da}$-Amidoglutaric amide)dibenzofulvene was thus prepared and was an off-white to yellow powder. $^1$H-NMR (CD$_2$Cl$_2$): δ (ppm) 8.7 (2H, s, NH); 8.1 (2H, s, Ar); 7.6 (2H, m Ar); 7.4 (2H, m, Ar); 6.5 (2H, bs, NH); 6.1 (2H, s, CH$_2$); 3.6 (s, PEG backbone); 3.3 (6H, s, —OCH$_3$); 2.5 (4H, t, CH$_2$); 2.3 (4H, t, CH$_2$); 2.0 (4H, m, CH$_2$).

Another polymeric reagent was prepared using this same approach except mPEG-NH$_2$ (prepared in high purity using conventional methods) having a weight average molecular weight of 20,000 was substituted for mPEG-NH$_2$ (10,000 Da) in the preparation of 9-hydroxymethyl-2,7-di(mPEG$_{10,000Da}$-amidoglutaric amide)fluorene. The resulting polymeric reagent had a total molecular weight of about 40,000 Daltons.

Example 3

Preparation of 4-(mPEG$_{10,000Da}$-carboxyamide)-7-(3-(mPEG$_{10,000Da}$)carbamoyl-propyl) dibenzofulvene (or 4,7-CAC-PEG2-fulvene 20K, or CAC-PEG2-fulvene 20K)

4-(mPEG$_{10,000Da}$-carboxyamide)-7-(3-(mPEG$_{10,000Da}$) carbamoyl-propyl) dibenzofulvene was prepared in accordance with the reaction scheme provided below.

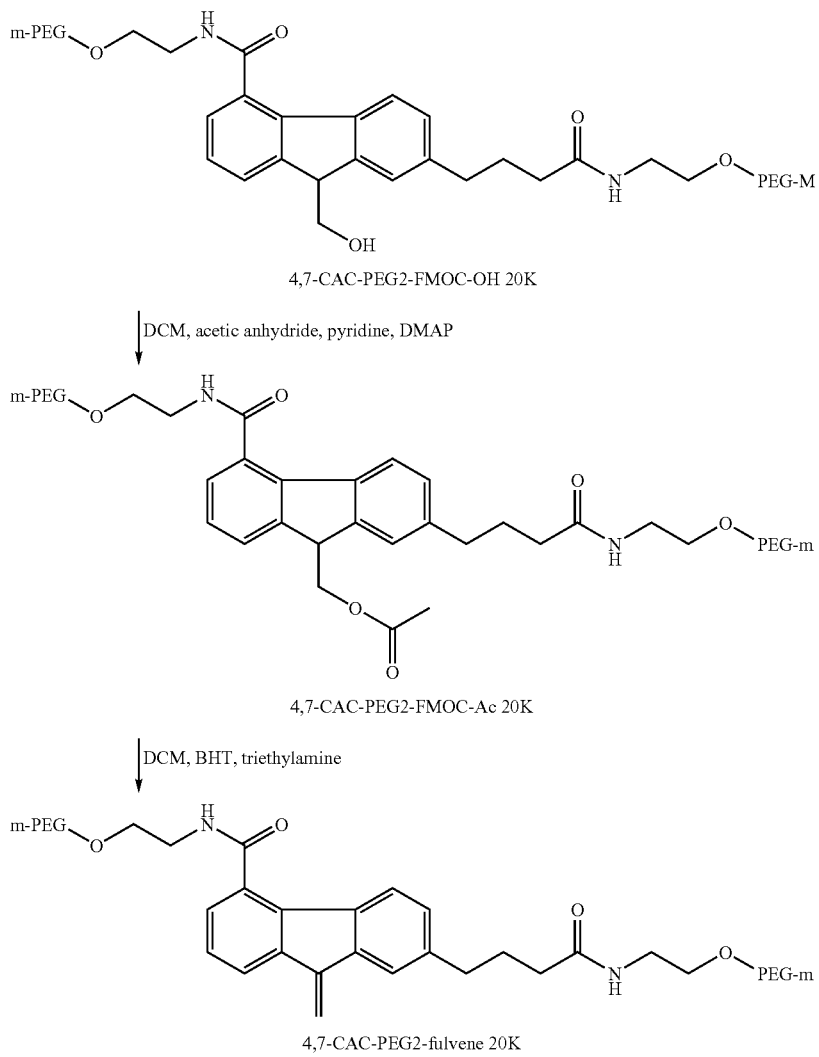

The synthesis was started with a sufficient amount of 9-hydroxymethyl-4-(mPEG$_{10,000Da}$-carboxyamide)-7-(3-(mPEG$_{10,000Da}$)carbamoyl-propyl)fluorene, prepared in accordance with the procedure described in U.S. Patent Application Publication No. 2006/0293499. From this, the corresponding 9-acetoxymethyl derivative was prepared following the general procedure set forth in Step 1, Example 1, described above. 9-Acetoxymethyl-4-(mPEG$_{10,000Da}$-carboxyamide)-7-(3-(mPEG$_{10,000Da}$)carbamoyl-propyl)fluorene (or 4,7-CAC-PEG2-FMOC-Ac 20K, or CAC-PEG2-FMOC-Ac 20K) was prepared and was an off-white powder. $^1$H-NMR (CD$_2$Cl$_2$): δ (ppm) 7.9 (1H, d, Ar); 7.7 (1H, d, Ar); 7.4 (2H, m, Ar); 7.3 (1H, t, Ar); 7.2 (1H, d, Ar); 6.7 (1H, bs, NH); 6.1 (1H, bs, NH); 4.4-4.3 (2H, m, CH$_2$); 4.2 (1H, t, CH); 3.6 (s, PEG backbone); 3.3 (6H, s, —OCH$_3$); 2.7 (2H, t, CH$_2$); 2.2 (2H, m, CH$_2$); 2.1 (3H, s, CH$_3$); 2.0 (2H, m, CH$_2$).

Next, 9-acetoxymethyl-4-(mPEG$_{10,000Da}$-carboxyamide)-7-(3-(mPEG$_{10,000Da}$)carbamoyl-propyl)fluorene was converted to 4-(mPEG$_{10,000Da}$-carboxyamide)-7-(3-(m PEG$_{10,000Da}$)carbamoyl-propyl)dibenzofulvene (or 4,7-CAC-PEG2-fulvene 20K, or CAC-PEG2-fulvene 20K) following the general procedure set forth in Step 2, Example 1, described above. 4-(mPEG(10,000)-Carboxyamide)-7-(3-(mPEG(10,000))carbamoyl-propyl)dibenzofulvene was thus prepared and was an off-white powder. $^1$H-NMR (CD$_2$Cl$_2$): δ (ppm) 7.8 (1H, m, Ar); 7.6 (1H, s, Ar); 7.4 (1H, m Ar); 7.3 (1H, m, Ar); 7.2 (1H, d, Ar); 6.8 (1H, bs, NH); 6.1 (1H, bs, NH); 6.1 (1H, d, CH$_2$); 3.6 (s, PEG backbone); 3.3 (6H, s, —OCH$_3$); 2.7 (2H, t, CH$_2$); 2.2 (2H, t, CH$_2$); 2.0 (2H, m, CH$_2$).

Example 4

Preparation of 2,7-di(mPEG$_{10,000Da}$-carboxyamide) dibenzofulvene (or 2,7-C2-PEG2-fulvene 20K, or C2-PEG2-fulvene 20K)

2,7-di(mPEG$_{10,000Da}$-Carboxyamide)dibenzofulvene was prepared in accordance with the reaction scheme provided below.

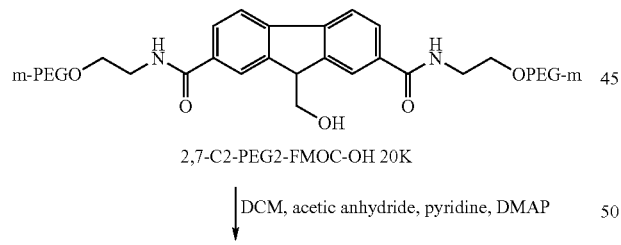

2,7-C2-PEG2-FMOC-OH 20K

↓ DCM, acetic anhydride, pyridine, DMAP

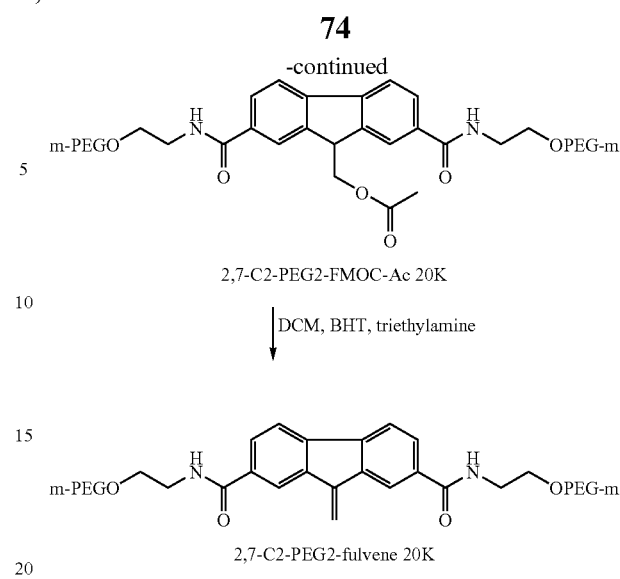

2,7-C2-PEG2-FMOC-Ac 20K

↓ DCM, BHT, triethylamine 2,7-C2-PEG2-fulvene 20K

The synthesis was started with a sufficient amount of 9-hydroxymethyl-2,7-di(mPEG$_{10,000Da}$-carboxyamide)fluorene, prepared in accordance with the procedure described in U.S. Patent Application Publication No. 2006/0293499. From this, the corresponding 9-acetoxymethyl derivative was prepared following the general procedure set forth in Step 1, Example 1, described above. 9-Acetoxymethyl-2,7-di(mPEG$_{10,000Da}$-carboxyamide)fluorene (or 2,7-C2-PEG2-FMOC-Ac 20K, or C2-PEG2-FMOC-Ac 20K) was prepared and was an off-white powder, approximately 70% substitution. $^1$H-NMR (CD$_2$Cl$_2$): δ (ppm) 8.1 (2H, s, Ar); 7.8 (4H, m, Ar); 6.9 (2H, bs, NH); 4.5 (2H, m, CH$_2$); 4.3 (1H, m, CH); 3.6 (s, PEG backbone); 3.3 (6H, s, —OCH$_3$); 2.1 (3H, s, CH$_3$).

Next, 9-acetoxymethyl-2,7-di(mPEG$_{10,000Da}$-carboxyamide)fluorene was converted to 2,7-di(mPEG$_{10,000Da}$-carboxyamide)dibenzofulvene (or 2,7-C2-PEG2-fulvene 20K, or C2-PEG2-fulvene 20K) following the general procedure set forth in Step 2, Example 1, described above. 2,7-di(mPEG$_{10,000Da}$-Carboxyamide)dibenzofulvene was thus prepared and was an off-white powder, approximately 70% substitution. $^1$H-NMR (CD$_2$Cl$_2$): δ (ppm) 8.3 (2H, s, Ar); 7.9 (4H, m, Ar); 7.0 (2H, bs, NH); 6.3 (2H, s, CH$_2$); 3.6 (s, PEG backbone); 3.3 (6H, s, —OCH$_3$).

Example 5

Preparation of Bromo-2,7-di(mPEG$_{10,000Da}$-amidoglutaric amide)dibenzofulvene (or Br-2,7-G2-PEG2-fulvene 20K, or Br-G2-PEG2-fulvene 20K)

Bromo-2,7-di(mPEG$_{10,000Da}$-amidoglutaric amide)dibenzofulvene was prepared in accordance with the reaction scheme provided below.

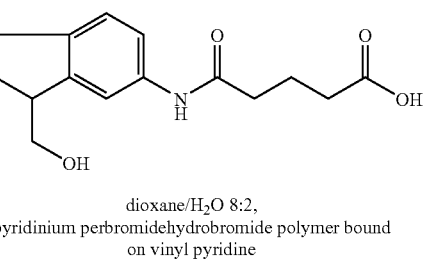

↓ dioxane/H$_2$O 8:2, pyridinium perbromidehydrobromide polymer bound on vinyl pyridine

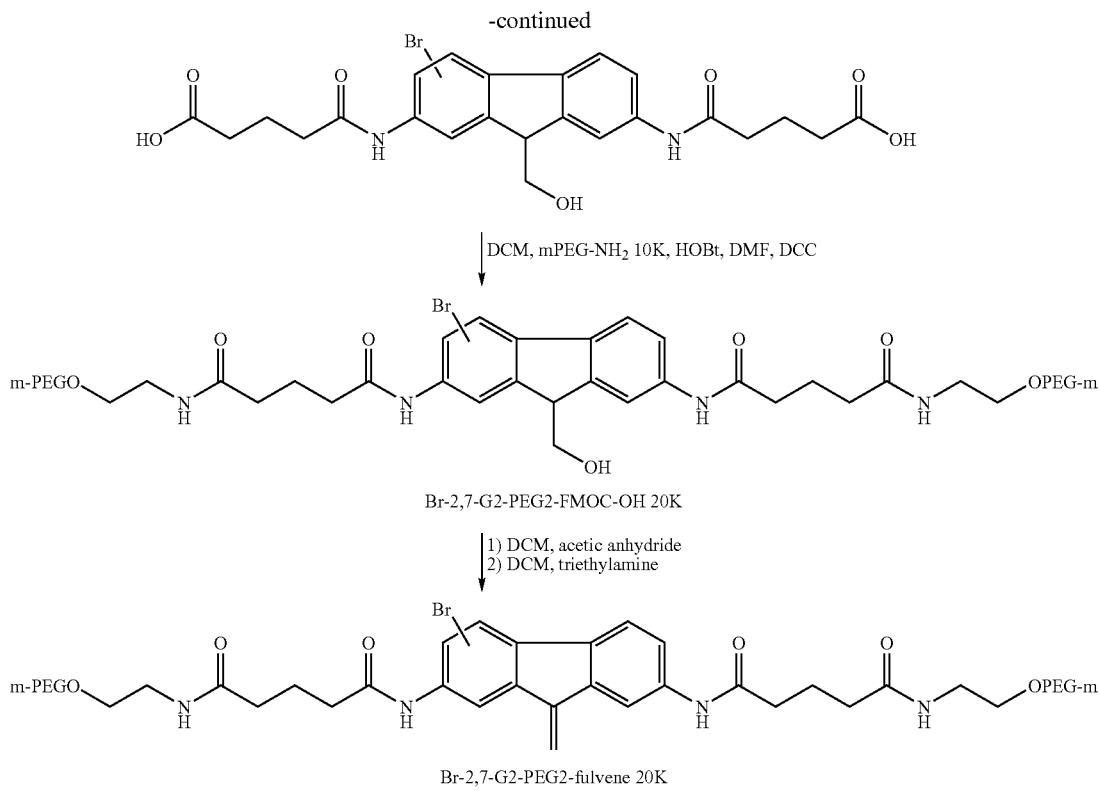

Br-2,7-G2-PEG2-fulvene 20K 9-hydroxymethyl-2,7-di(amidoglutaric acid)fluorene (1.5 g, 3.3 mmol) was dissolved in 1,4-dioxane (45 mL) and deionized water (30 mL). Pyridine hydrobromide perbromide (bound on vinyl pyridine polymer, ~2 mmol $Br_3$/g resin, 2.5 g) was added and stirred in the dark for two hours. The reaction suspension was filtered and washed with 1,4-dioxane/water (20 mL) and then 1,4-dioxane (20 mL). The product was extracted with half-saturated sodium chloride and ethyl acetate (2×400 mL). The organic solvent was dried over anhydrous sodium sulphate, filtered and evaporated at reduced pressure. The resulting crude product was separated by chromatography C18 silica using a 50 mM ammonium acetate pH 4.75 and methanol gradient elution. Yield was 0.4 g, off-white powder. $^1$H-NMR ($d_6$-DMSO): δ (ppm) 8.1 (1H, s, Ar); 7.9 (1H, s, Ar); 7.8 (2H, m, Ar); 7.6 (1H, d, Ar); 4.0 (1H, t, CH); 3.7 (2H, m, $CH_2$); 2.4 (4H, m, $CH_2$); 2.2 (4H, m, $CH_2$); (1.8, m, $CH_2$).

Bromo-2,7-di(mPEG$_{10,000Da}$-amidoglutaric amide)dibenzofulvene (or Br-2,7-G2-PEG2-fulvene 20K, or Br-G2-PEG2-fulvene 20K) was prepared by methods similar to the non-brominated derivative (i.e., 2,7-G2-PEG2-fulvene 20K). Briefly, mPEG$_{10,000Da}$-$NH_2$ is reacted with bromo-2,7-di(mPEG$_{10,000Da}$-amidoglutaric amide)dibenzofulvene in accordance with the procedure described in U.S. Patent Application Publication No. 2006/0293499 to provide BR-2,7-G2-PEG2-FMOC-OH 20K. BR-2,7-G2-PEG2-FMOC-OH 20K, in turn, was used to form the corresponding 9-acetoxymethyl derivative following the general procedure set forth in Step 1, Example 1, described above. The 9-acetoxymethyl derivative, in turn, was converted to bromo-2,7-di(mPEG$_{10,000Da}$-amidoglutaric amide)dibenzofulvene following the general procedure set forth in Step 2, Example 1, described above. Bromo-2,7-di(mPEG$_{10,000Da}$-amidoglutaric amide)dibenzofulvene was thus prepared and was off-white powder. $^1$H-NMR ($CD_2Cl_2$): δ (ppm) 9.0 (1H, bs, NH); 8.6 (1H, s, NH); 8.2 (1H, s, Ar); 8.0 (1H, m, Ar); 7.8 (1H, s, Ar); 7.6 (2H, s, Ar); 6.2 (2H, m, $CH_2$); 3.6 (s, PEG backbone); 3.3 (6H, s, —$OCH_3$); 2.6 (4H, m, $CH_2$); 2.4 (4H, m, $CH_2$); 2.0 (4H, m, $CH_2$).

Example 6

Figure 1B:
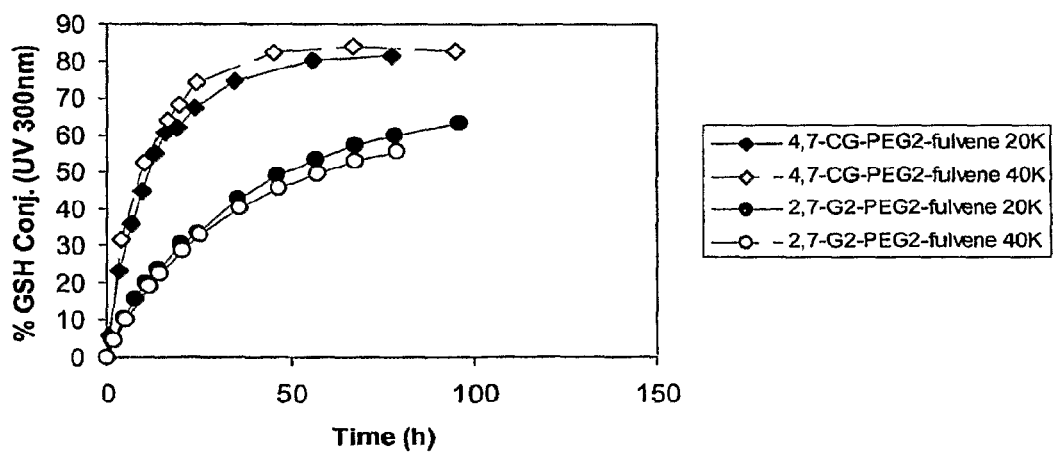
FIG. 1B shows the area percent of negatively charged PEG2-fulvene-GSH (thioether) conjugate vs. neutral PEG2-fulvene 20K or 40K reagent as indicated. Polymer was 0.5 mmol in 50 mM HEPES pH 6.8 with GSH 2.5 mM at 37° C., nitrogen sparged. Fulvene structure variations are indicated in key. Percentages determined by HPLC size exclusion chromatography.
Figure 2:
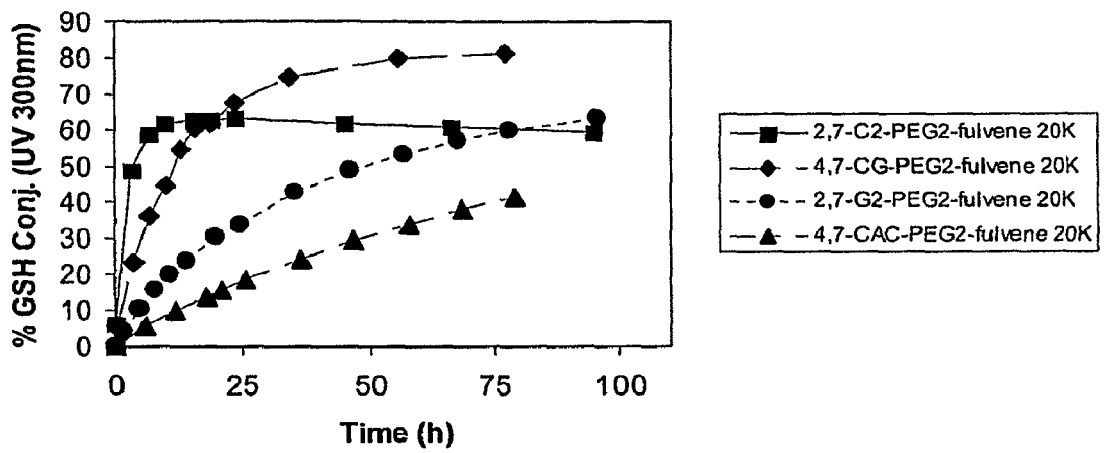
FIG. 2 shows the area percent of negatively charged PEG2-fulvene-GSH (thioether) conjugate vs. neutral PEG2-fulvene 20K reagent. Polymer was 0.5 mmol in 50 mM HEPES pH 6.8 with GSH 2.5 mM at 37° C., nitrogen sparged. Fulvene structure variations are indicated in key. Percentages determined by HPLC size exclusion chromatography.

Preparation of Glutathione (GSH) Conjugates with Exemplary Polymeric Reagents and Release Data 4-(mPEG$_{10,000Da}$-carboxyamide)-7-(mPEG$_{10,000Da}$ amidoglutaric amide)dibenzofulvene (10 mg, ~90% fulvene substituted), prepared as described in Example 1, was dissolved in a buffer solution of 50 mM HEPES pH 7.4+15 mM L-glutathione reduced (GSH) and incubated at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection). Results are presented in FIG. 1A ("4,7-CG"). Another polymer sample (10 mg) was prepared in 50 mM HEPES pH 6.8+2.5 mM GSH and incubated at 37° C. At various intervals an aliquot was injected on a HPLC system and separated by mass and charge characteristic on a size-exclusion column. Results are presented in FIG. 1B ("4,7-CG-PEG2-fulvene 20K") and FIG. 2 ("4,7-CG-PEG2-fulvene 20K").

Another polymeric reagent 4-(mPEG$_{20,000Da}$-carboxyamide)-7-(mPEG$_{20,000Da}$ amidoglutaric amide)dibenzofulvene (10 mg, ~90% fulvene substituted), prepared as described in Example 1, was dissolved in a buffer solution of 50 mM HEPES pH 6.8+2.5 mM L-glutathione reduced (GSH) and incubated at 37° C. At various intervals an aliquot was injected on a HPLC system and separated by mass and charge characteristic on a size-exclusion column. Results are presented in FIG. 1B ("4,7-CG-PEG2-fulvene 40K").

2,7-Di(mPEG$_{10,000Da}$-amidoglutaric amide)dibenzofulvene (10 mg, ~90% fulvene substituted), prepared as described in Example 2, was dissolved in a buffer solution of 50 mM HEPES pH 7.4+15 mM L-glutathione reduced (GSH) and incubated at 37° C. A various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. Results are presented in FIG. 1A ("2,7-G2"). Another polymer sample (10 mg) was prepared in 50 mM HEPES pH 6.8+2.5 mM GSH and incubated at 37° C. At various intervals an aliquot was injected on a HPLC system and separated by mass and charge characteristic on a size-exclusion column. Results are presented in FIG. 1B ("2,7-G2-PEG2-fulvene 20K") and FIG. 2 ("2,7-G2-PEG2-fulvene 20K").

Another polymeric reagent 2,7-di(mPEG$_{20,000Da}$-amidoglutaric amide)dibenzofulvene (10 mg, ~90% fulvene substituted), prepared as described in Example 1, was dissolved in a buffer solution of 50 mM HEPES pH 6.8+2.5 mM L-glutathione reduced (GSH) and incubated at 37° C. At various intervals an aliquot was injected on a HPLC system and separated by mass and charge characteristic on a size-exclusion column. Results are presented in FIG. 1B ("2,7-G2-PEG2-fulvene 40K").

4-(mPEG$_{10,000Da}$-carboxyamide)-7-(3-(mPEG$_{10,000Da}$)carbamoyl-propyl)dibenzofulvene (10 mg, ~90% fulvene substituted), prepared as described in Example 3, was dissolved in a buffer solution of 50 mM HEPES pH 7.4+15 mM L-glutathione reduced (GSH) and incubated at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. Results are presented in FIG. 1 ("4,7-CAC"). Another polymer sample (10 mg) was prepared in 50 mM HEPES pH 6.8+2.5 mM GSH and incubated at 37° C. At various intervals an aliquot was injected on a HPLC system and separated by mass and charge characteristic on a size-exclusion column. Results are presented in FIG. 2 ("4,7-CAC-PEG2-fulvene 20K").

2,7-Di(mPEG$_{10,000Da}$-carboxyamide)dibenzofulvene (10 mg, ~70% fulvene substituted), prepared as described in Example 4, was dissolved in a buffer solution of 50 mM HEPES pH 7.4+15 mM L-glutathione reduced (GSH) and incubated at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. Results are presented in FIG. 1 ("2,7-C2"). Another polymer sample (10 mg) was prepared in 50 mM HEPES pH 6.8+2.5 mM GSH and incubated at 37° C. At various intervals an aliquot was injected on a HPLC system and separated by mass and charge characteristic on a size-exclusion column. Results are presented in FIG. 2 ("2,7-C2-PEG2-fulvene 20K").

Example 7

Preparation of 9-hydroxymethyl-2-amido-triethylene glycol amine fluorene

9-Hydroxymethyl-2-amido-triethylene glycol amine fluorene was prepared in accordance with the reaction scheme provided below.

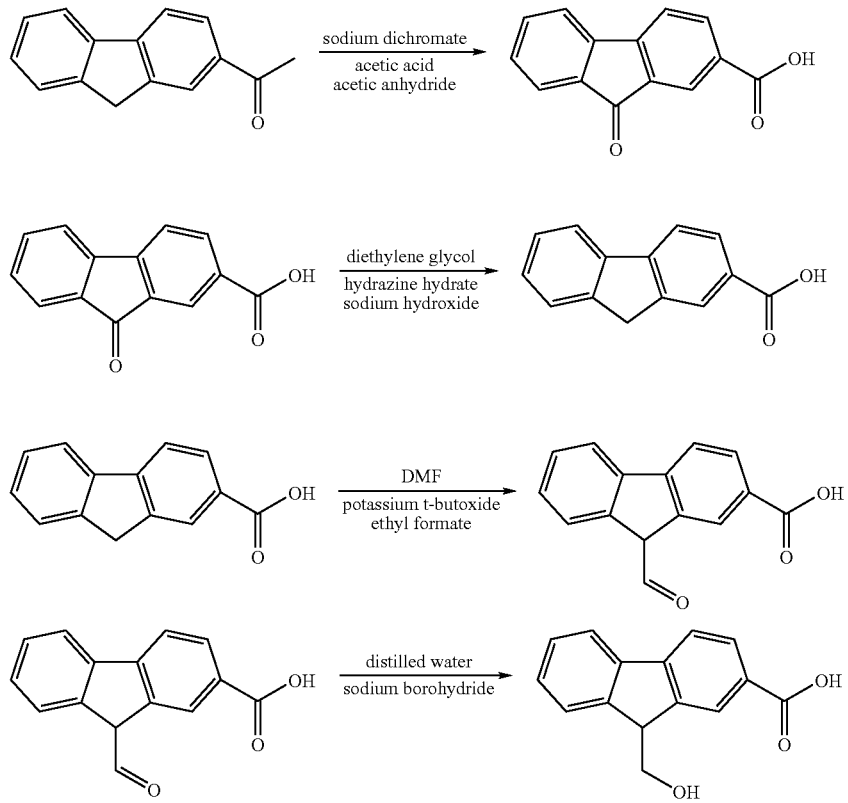

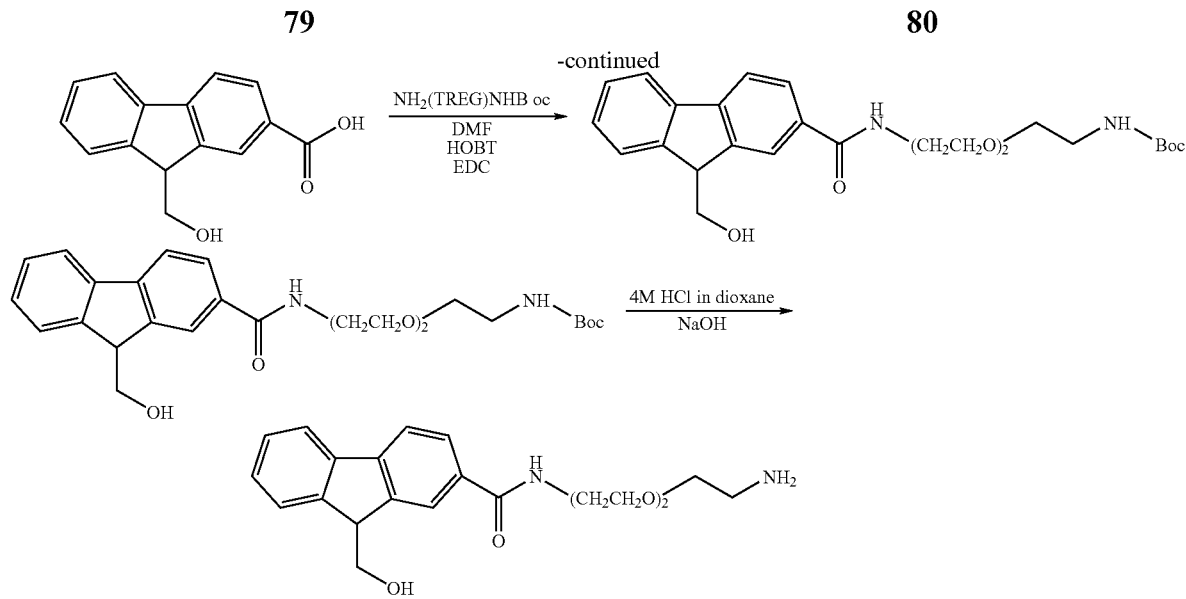

Preparation of 2-carboxyfluorenone

2-Acetylfluorene (25.5 g, 0.12 mole) was dissolved in glacial acetic acid (325 mL). Sodium dichromate dihydrate (345 g, 1.16 mole) and acetic anhydride (138.4 mL, 1.46 mole) were added to the solution. The temperature of the reaction solution was increased to 120° C. (with reflux apparatus). The reaction was allowed to proceed for 16 hours. The reaction solution was cooled and diluted with distilled water (1.8 L). The solution was heated to approximately 80° C. and filtered. The precipitate was dissolved in 1M sodium hydroxide. The solution was washed with dichloromethane (3×160 mL). The aqueous solution was heated to approximately 80° C. and acidified with concentrated hydrochloric acid (pH approximately 2). The material was filtered and placed under vacuum to dry with phosphorus pentoxide present. The NMR spectrum was consistent with the loss of the acetyl methyl singlet and retention of other characteristic peaks.

Preparation of 2-carboxyfluorene

2-Carboxyfluorenone (12.3 g, 0.05 mole) and diethylene glycol were added to a 500 mL round bottom flask. Sodium hydroxide (7.65 g, 0.19 mole) and hydrazine hydrate (9.16 mL, 0.23 mole) were added to the solution. The temperature of the reaction was increased to 125° C. Heating was continued for three hours and then the vessel was cooled to room temperature. Distilled water (1.5 L) was added. The product was precipitated with concentrated hydrochloric acid. The product was filtered and rinsed with distilled water (2 L). The solids were dissolved in 0.5 M sodium hydroxide (2.8 L) and heated to 70° C. The product was precipitated with concentrated hydrochloric acid (pH approximately 2). The product was filtered and washed with distilled water (1.5 L). The 2-carboxyfluorene was dried overnight under reduced pressure with phosphorus pentoxide present. NMR confirmed the structure by the appearance of two new protons at $\delta 4.01$ ppm.

Preparation of 2-carboxy-9-formylfluorene

2-Carboxyfluorene (2.8 g, 0.014 mole) was dissolved in anhydrous dimethylformamide (DMF, 133 mL). Potassium t-butoxide (12.5 g, 0.11 mole) and ethyl formate (400 mL) were added to the reaction solution. The temperature of the solution was increased to 60° C. for 5-10 minutes. The reaction solution was cooled to room temperature. Total reaction time was three hours. Ethyl formate was distilled off and 1M hydrochloric acid (150 mL) was added to the reaction mixture. The solid was filtered and washed with distilled water. The precipitate was dried overnight under reduced pressure with phosphorous pentoxide present. NMR confirmed the structure by the appearance of one new proton at $\delta 11.47$ ppm (aldehyde hydrogen).

Preparation of 2-carboxy-9-hydroxymethylfluorene

2-Carboxy-9-formylfluorene (2.77 g, 0.012 mole) and distilled water (110 mL) were added to a round bottom flask. Sodium borohydride (8.65 g, 0.228 mole) was added slowly to the reaction solution. After approximately twenty minutes additional sodium borohydride (8.65 g, 0.228 mol) was added. After approximately 16 hours at room temperature, 1 M hydrochloric acid was added until the pH of the solution was approximately 2. The product was filtered and rinsed with distilled water. The 2-carboxy-9-hydroxymethylfluorene was dried under reduced pressure with either phosphorus pentoxide or drierite present. NMR confirmed the structure by the disappearance of the aldehyde proton and the appearance of a multiplet (three protons) centered at $\delta 4.05$ ppm, which is consistent with the proton at C-9 and the methylene of the hydroxymethyl group.

Preparation of 9-hydroxymethyl-2-amido-triethylene glycol Boc amine flourene 2-Carboxy-9-hydroxymethylfluorene (1.10 g, 4.6 mmol) was added to a round bottom flask. In a separate flask, Boc-triethylene gycol-amine ["NH$_2$(TREG)NHBoc," 1.59 g, 6.4 mmol] was dissolved in DMF (7.0 mL). The solution was dried with molecular sieves (1.5 g). The solution was then transferred (6.54 mL, 5.98 mmole) to the flask containing 2-carboxy-9-hydroxymethylfluorene. DMF (5 mL), 1-hydroxybenzotriazole, anhydrous (0.62 g, 4.6 mmol), and 1-ethyl-3-(3-dimethylamino-propyl) carbodiimide (EDC), 98% (1.17 g, 5.98 mmole) were added. The reaction was continued for 3 hours 15 minutes at room temperature.

Dichloromethane (140 mL) was added to the reaction mixture. The product was washed with 0.25 M sulfuric acid/1% sodium chloride (3×140 mL). The DCM layer was dried with sodium sulfate (20 g) and filtered. The DCM was distilled and the product was placed under reduced pressure overnight.

Preparation of 9-hydroxymethyl-2-amido-triethylene glycol amine fluorene

9-Hydroxymethyl-2-amido-triethylene glycol Boc amine fluorene (2.15 g, 4.57 mmol) was dissolved in 4M HCl in dioxane (20 mL). The reaction was reacted for 3 hours 15 minutes. The solvents were distilled off. Distilled water (100 mL) and sodium chloride (10 g) were added to the product. The pH of the solution was adjusted to 12.6 with 1M sodium hydroxide. The product was extracted with dichloromethane (60 mL). The DCM extract was washed with saturated sodium chloride solution (2×80 mL). The DCM layer was dried with sodium sulfate (20 g) and filtered. The solvent was distilled off, and the 9-hydroxymethyl-2-amido-triethylene glycol amine was dried overnight under reduced pressure.

NMR confined the structure by the appearance of a multiplets centered at δ4.06 ppm (1H, amide NH), δ3.61 ppm (2H, amine NH), and δ3.56 (8H, C$\underline{H}_2$C$\underline{H}_2$O).

Example 8

Preparation of 2-mPEG$_{5000Da}$ amido-TEG-dibenzofulvene 2-mPEG$_{5000Da}$ Amido-TEG-dibenzofulvene was prepared in accordance with the reaction scheme provided below.

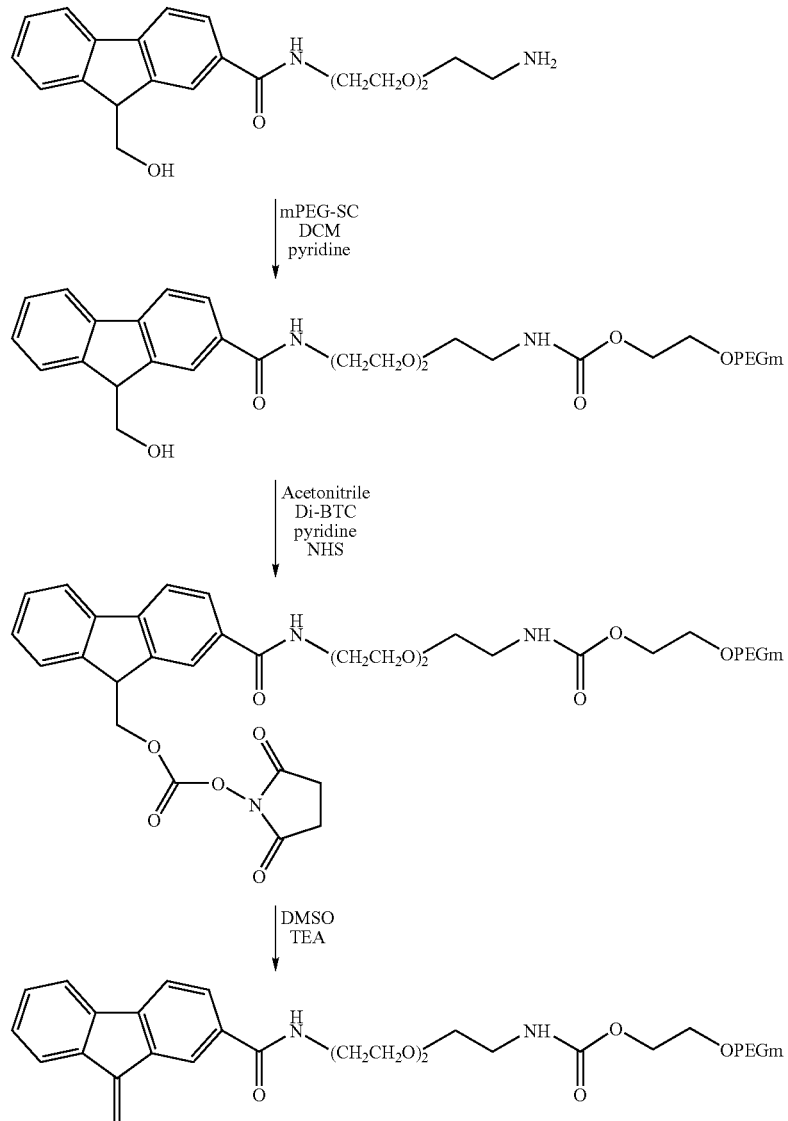

Preparation of 2-mPEG$_{5000Da}$ amido-TEG-9-MeOH fluorene mPEG-succinimidyl carbonate 5K (4.23 g, 0.85 mmol) and 9-hydroxymethyl-2-amido-triethylene glycol amine (0.36 g, 0.97 mmol) were dissolved in anhydrous dichloromethane (42 mL). Pyridine (65 μL, 0.80 mmol) was added to the reaction solution. The reaction was conducted overnight at room temperature. The reaction solution was distilled to a viscous residue. The polymer was precipitated by adding the viscous solution to anhydrous ethyl ether. The precipitate was filtered and dried under reduced pressure. NMR confirmed the structure by the appearance of a multiplets centered at δ7.6-8.1 ppm (7H, aromatic protons) and δ3.6 ppm (approximately 55,400H, $CH_2CH_2O$ polymer backbone).

Preparation of 2-mPEG$_{5000Da}$ amido-TEG-FMOC-NHS carbonate 2-mPEG$_{5000Da}$ amido-TEG-9-MeOH fluorene (1.39 g, 0.28 mmole) was dissolved in anhydrous acetonitrile (45 mL). The solvent was distilled until solid appeared. The solid material was dissolved in anhydrous acetonitrile (6 mL). Dibenzotriazoyl carbonate ("Di-BTC," 0.2170 g, 55.85 weight percent Di-BTC, 0.41 mmol) and pyridine (10.6 μL) were added. Anhydrous acetonitrile (6 mL) was added to the reaction solution. The reaction was continued for 3 hours at room temperature. N-Hydroxysuccinimide ("NHS," 0.57 g, 4.95 mmol) was added to the reaction solution. The solution was allowed to react overnight (16 hours) at room temperature. The reaction solution was added to anhydrous ethyl ether (150 mL). The resulting precipitate was filtered and washed with anhydrous ethyl ether (50 mL). The material was dried using an argon stream. NMR confirmed the structure by the appearance of the characteristic singlet for the succinimide ring protons.

Preparation of 2-mPEG$_{5000Da}$ amido-TEG-dibenzofulvene 2-mPEG$_{5000Da}$ amido-TEG-FMOC-NHS carbonate (0.52 g, 0.10 mmol) was dissolved in dimethyl sulfoxide (10 mL) at 40° C. Triethylamine (0.45 mL, 3.23 mmol) was added to reaction solution. The reaction remained at 40° C. for one hour. The solution was transferred to anhydrous ethyl ether (300 mL). The material was filtered and washed with anhydrous ethyl ether (50 mL). The product was placed under reduced pressure to dry. NMR confirmed the structure by the appearance of the doublet for the two vinylic protons at δ7.6-8.1 ppm.

4-(mPEG$_{10,000Da}$-carboxyamide)-7-(mPEG$_{10,000D}$a amidoglutaric amide)dibenzofulvene (20 mg, ~90% fulvene substituted), prepared as described in Example 1, was dissolved in 2.0 mL nitrogen sparged buffer solution of 100 mM HEPES pH 6.8+30 mM L-glutathione reduced (GSH) and incubated at 37° C. for 3.5 hours. The conjugates were then dialyzed (MWCO 10 kD, at room temperature) two times with 500 mL of nitrogen sparged 25 mM HEPES pH 6.9 then 2 times with 500 mL of nitrogen sparged 25 mM HEPES pH 7.4.

Figure 3:
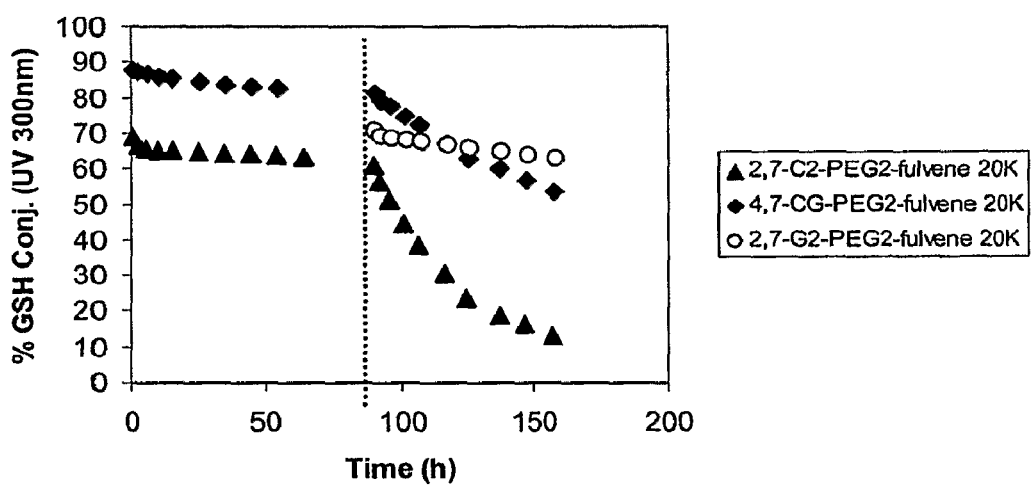
FIG. 3 shows the area percent of negatively charged PEG2-fulvene-GSH (thioether) conjugate vs. neutral PEG2 20K polymer. GSH conjugate was preformed with PEG2-fulvene 20K by incubation 0.5 mmol polymer in 100 mM HEPES pH 6.8 with GSH 30 mM at 37° C., nitrogen sparged for 3.5 hours. The conjugates were then dialyzed (MWCO 10 kD, room temperature) 2 times 500 mL of 25 mM HEPES pH 6.9 then 2 times 500 mL of 25 mM HEPES pH 7.4. The dialyzed GSH conjugates were then incubated at 37° C. and assayed by HPLC at intervals. At the indicated time, excess 2-mercaptoethanol (5 microL/mL conjugate solution) was added and assay intervals were continued. Fulvene structure variations are indicated in key. Percentages determined by HPLC size exclusion chromatography.

The dialyzed GSH conjugate solutions were nitrogen sparged, incubated at 37° C. and injected at various intervals on an HPLC system that separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. After ninety hours, an excess of 2-mercaptoethanol (5 microL/mL PEG solution) was added the sample was nitrogen sparged and incubation continued at 37° C. The sample was analyzed by HPLC at various intervals. Results are presented in FIG. 3 ("4,7-CG-PEG2-fulvene 20K").

2,7-Di(mPEG$_{10,000Da}$-amidoglutaric amide)dibenzofulvene (20 mg, ~90% fulvene substituted), prepared as described in Example 2, was dissolved in 2.0 mL nitrogen sparged buffer solution of 100 mM HEPES pH 6.8+30 mM L-glutathione reduced (GSH) and incubated at 37° C. for 3.5 hours. The conjugates were then dialyzed (MWCO 10 kD, at room temperature) 2 times with 500 mL of nitrogen sparged 25 mM HEPES pH 6.9 then 2 times with 500 mL of nitrogen sparged 25 mM HEPES pH 7.4.

The dialyzed GSH conjugate solutions were nitrogen sparged, incubated at 37° C. and injected at various intervals on an HPLC system that separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. After ninety hours, an excess of 2-mercaptoethanol (5 microL/mL PEG solution) was added the sample was nitrogen sparged and incubation continued at 37° C. The sample was analyzed by HPLC at various intervals. Results are presented in FIG. 3 ("2,7-G2-PEG2-fulvene 20K").

4-(mPEG$_{10,000Da}$-carboxyamide)-7-(3-(mPEG$_{10,000Da}$) carbamoyl-propyl)dibenzofulvene (20 mg, ~90% fulvene substituted), prepared as described in Example 3, was dissolved in 2.0 mL nitrogen sparged buffer solution of 100 mM HEPES pH 6.8+30 mM L-glutathione reduced (GSH) and incubated at 37° C. for 3.5 hours. The conjugates were then dialyzed (MWCO 10 kD, at room temperature) 2 times with 500 mL of nitrogen sparged 25 mM HEPES pH 6.9 then 2 times with 500 mL of nitrogen sparged 25 mM HEPES pH 7.4.

The dialyzed GSH conjugate solutions were nitrogen sparged, incubated at 37° C. and injected at various intervals on an HPLC system that separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. After ninety hours, an excess of 2-mercaptoethanol (5 microL/mL PEG solution) was added the sample was nitrogen sparged and incubation continued at 37° C. The sample was analyzed by HPLC at various intervals (data not shown).

2,7-Di(mPEG$_{10,000Da}$-carboxyamide)dibenzofulvene (20 mg, ~70% fulvene substituted), prepared as described in Example 4, was dissolved in 2.0 mL nitrogen sparged buffer solution of 100 mM HEPES pH 6.8+30 mM L-glutathione reduced (GSH) and incubated at 37° C. for 3.5 hours. The conjugates were then dialyzed (MWCO 10 kD, at room temperature) 2 times with 500 mL of nitrogen sparged 25 mM HEPES pH 6.9 then 2 times with 500 mL of nitrogen sparged 25 mM HEPES pH 7.4.

The dialyzed GSH conjugate solutions were nitrogen sparged, incubated at 37° C. and injected at various intervals on an HPLC system that separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. After ninety hours, an excess of 2-mercaptoethanol (5 microL/mL PEG solution) was added the sample was nitrogen sparged and incubation continued at 37° C. The sample was analyzed by HPLC at various intervals. Results are presented in FIG. 3 ("2,7-C2-PEG2-fulvene 20K").

Release data for the $t_{1/2}$ values were obtained from the slope of the linear fit to a plot of ln([conjugate]) vs. time, according to the first order rate law. Where $t_{1/2}=\ln(2)/m$; and m=slope of the first order plot.

Figure 4:
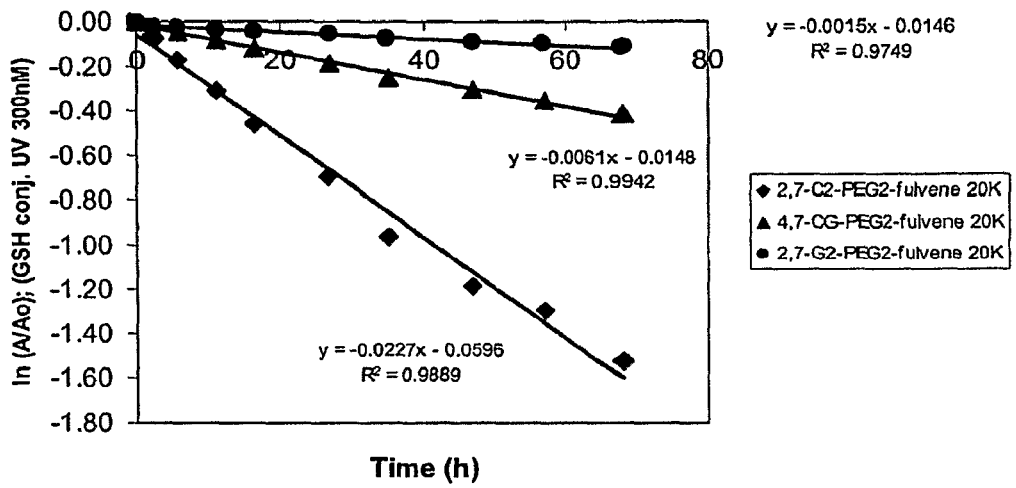
FIG. 4 shows a first order plot of PEG2-fulvene-GSH (thioether) conjugate release. Data obtained after addition of excess 2-mercaptoethanol to pre-dialyzed GSH conjugate. Conditions were 25 mM HEPES pH 7.4 at 37° C. Fulvene structure variations are indicated in key. Percentages determined by HPLC size exclusion chromatography.

Release data for the 4-(mPEG$_{10,000Da}$-carboxyamide)-7-(mPEG$_{10,000Da}$ amidoglutaric amide)dibenzofulvene-L-glutathione (thioether) conjugate at 37° C.: 25 mM HEPES pH 7.4+excess 2-mercaptoethanol (5 microL/mL PEG solution), $t_{1/2}$=4.7 days (for one experiment). Results are presented in FIG. 4 ("4,7-CG-PEG2-fulvene 20K").

Release data for the 2,7-di(mPEG$_{10,000Da}$-amidoglutaric amide)dibenzofulvene-L-glutathione (thioether) conjugate at 37° C.: 25 mM HEPES pH 7.4+excess 2-mercaptoethanol (5 microL/mL PEG solution), $t_{1/2}$=19.3 days (for one experiment). Results are presented in FIG. 4 ("2,7-G2-PEG2-fulvene 20K").

Release data for the 2,7-Di(mPEG$_{10,000Da}$-carboxyamide) dibenzofulvene-L-glutathione (thioether) conjugate at 37° C.: 25 mM HEPES pH 7.4+excess 2-mercaptoethanol (5 microL/mL PEG solution), $t_{1/2}$=30 hours (for one experiment). Results are presented in FIG. 4 ("2,7-C2-PEG2-fulvene 20K").

Release data for the 4-(mPEG$_{10,000Da}$-carboxyamide)-7-(3-(mPEG$_{10,000Da}$)carbamoyl-propyl)dibenzofulvene-L-glutathione (thioether) conjugate at 37° C.: 25 mM HEPES pH 7.4+excess 2-mercaptoethanol (5 microL/mL PEG solution), $t_{1/2}$=not calculated was observed to release more slowly than the 2,7-Di(mPEG(10,000)-amidoglutaric amide)dibenzofulvene-L-glutathione (thioether) conjugate described above (for one experiment, data not shown).

Example 7

Figure 5:
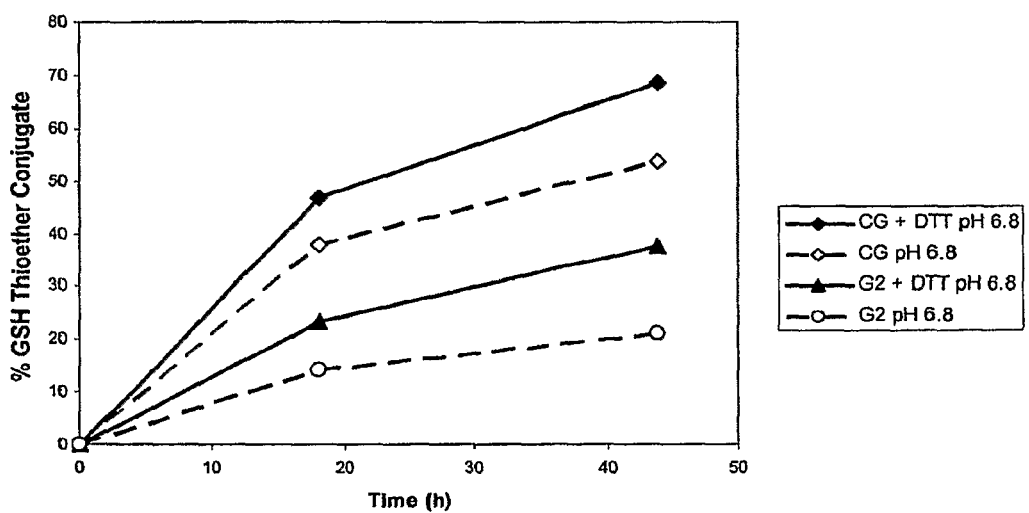
FIG. 5 shows a plot of the percentage of conjugation of various fulvene-based polymer reagents with 3-mercaptopropionic acid over time. Fulvene structure variations are indicated in key. Percentages determined by HPLC size exclusion chromatography.

Preparation of 3-Mercaptopropionic Acid Conjugates with Exemplary Polymeric Reagents 4-(mPEG$_{10,000Da}$-carboxyamide)-7-(mPEG$_{10,000Da}$ amidoglutaric amide)dibenzofulvene (10 mg, ~90% fulvene substituted), prepared as described in Example 1, was dissolved in a buffer solution of 50 mM HEPES+10 mM 3-mercaptopropionic acid pH 6.8 and incubated at 37° C. (designated as "CG pH 6.8" in FIG. 5). At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. Another polymer sample (designated as "CG+DTT pH 6.8" in FIG. 5," 10 mg) was prepared in 50 mM HEPES+10 mM 3-mercaptopropionic acid+1 mM dithiothreitol pH 6.8 and incubated at 37° C. At various intervals an aliquot was injected on a HPLC system and separated by mass and charge characteristic on a size-exclusion column. Results are presented in FIG. 5.

2,7-Di(mPEG$_{10,000Da}$-amidoglutaric amide)dibenzofulvene (10 mg, ~90% fulvene substituted), prepared as described in Example 2, was dissolved in a buffer solution of 50 mM HEPES+10 mM 3-mercaptopropionic acid pH 6.8 and incubated at 37° C. (designated as "G2 pH 6.8" in FIG. 5). At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. Another polymer sample (designated as "G2+DTT pH 6.8" in FIG. 5, "10 mg) was prepared in 50 mM HEPES+10 mM 3-mercaptopropionic acid+1 mM dithiothreitol pH 6.8 and incubated at 37° C. At various intervals an aliquot was injected on a HPLC system and separated by mass and charge characteristic on a size-exclusion column. Results are presented in FIG. 5.

4-(mPEG$_{10,000Da}$-carboxyamide)-7-(3-(mPEG$_{10,000Da}$) carbamoyl-propyl)dibenzofulvene (10 mg, ~90% fulvene substituted), prepared as described in Example 3, was dissolved in a buffer solution of 50 mM HEPES+12 mM 3-mercaptopropionic acid pH 6.8 and incubated at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection (Data not shown).

2,7-Di(mPEG$_{10,000Da}$-carboxyamide)dibenzofulvene (10 mg, ~70% fulvene substituted), prepared as described in Example 3, was dissolved in a buffer solution of 50 mM HEPES+12 mM 3-mercaptopropionic acid pH 6.8 and incubated at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 05 mL/min, refractive index and UV (300 nm) detection (Data not shown).

Example 8

Preparation of Cysteine Conjugates with Exemplary Polymeric Reagents 2,7-Di(mPEG$_{10,000Da}$-amidoglutaric amide)dibenzofulvene (10 mg, ~90% fulvene substituted), prepared as described in Example 2, was dissolved in a nitrogen sparged buffer solution of 25 mM HEPES+5 mM N-α-Boc-cysteine pH 7.4 and incubated at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. Results demonstrated significant cysteine formation similar to observations with GSH and 3-mercaptopropionic acid (data not shown).

Example 9

Evaluated Reactivity of Exemplary PEG2-Fulvene Polymeric Reagents with Relevant Amines 4-(mPEG$_{20,000Da}$-carboxyamide)-7-(mPEG$_{20,000Da}$ amidoglutaric amide)dibenzofulvene (10 mg, ~90% fulvene substituted), prepared as described in Example 1, was dissolved in a buffer solution of 1% glycine+25 mM HEPES pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 24 hours incubation (data not shown).

4-(mPEG$_{10,000Da}$-carboxyamide)-7-(mPEG$_{10,000Da}$ amidoglutaric amide)dibenzofulvene (10 mg, ~90% fulvene substituted), prepared as described in Example 1, was dissolved in a buffer solution of 1% N-α-Boc-histidine+25 mM HEPES pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 24 hours incubation (data not shown).

4-(mPEG$_{20,000Da}$-carboxyamide)-7-(mPEG$_{20,000Da}$ amidoglutaric amide)dibenzofulvene (10 mg, ~90% fulvene substituted), prepared as described in Example 1, was dissolved in a buffer solution of 1% N-α-Boc-histidine+25 mM HEPES pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 24 hours incubation (data not shown).

2,7-Di(mPEG$_{10,000Da}$-amidoglutaric amide)dibenzofulvene (10 mg, ~90% fulvene substituted), prepared as described in Example 2, was dissolved in a buffer solution of 5% glycine pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 1 day, 3 days, or 5 days incubation (data not shown).

2,7-Di(mPEG$_{20,000Da}$-amidoglutaric amide)dibenzofulvene (10 mg, ~90% fulvene substituted), prepared as described in Example 2, was dissolved in a buffer solution of 65 mM N-α-Boc-histidine+50 mM HEPES pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 24 hours incubation (data not shown).

2,7-Di(mPEG$_{10,000Da}$-amidoglutaric amide)dibenzofulvene (10 mg, ~90% fulvene substituted), prepared as described in Example 2, was dissolved in a buffer solution of 50 mM HEPES+50 mM histidine pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 1 day, 3 days, or 5 days incubation (data not shown).

2,7-Di(mPEG$_{10,000Da}$-amidoglutaric amide)dibenzofulvene (10 mg, ~90% fulvene substituted), prepared as described in Example 2, was dissolved in a buffer solution of 50 mM HEPES+50 mM lysine pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 1 day, 3 days, or 5 days incubation (data not shown).

2,7-Di(mPEG$_{10,000Da}$-amidoglutaric amide)dibenzofulvene (10 mg, ~90% fulvene substituted), prepared as described in Example 2, was dissolved in a buffer solution of 50 mM HEPES+50 mM glycine pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 1 day, 3 days, or 5 days incubation (data not shown).

4-(mPEG$_{10,000Da}$-carboxyamide)-7-(3-(mPEG$_{10,000Da}$) carbamoyl-propyl)dibenzofulvene (10 mg, ~90% fulvene substituted), prepared as described in Example 3, was dissolved in a buffer solution of 65 mM N-α-Boc-histidine+50 mM HEPES pH 7.4 at 37° C. At various intervals an aliquot was injected on a HPLC system and separated by mass and charge characteristic on a size-exclusion column (Agilent 1200 HPLC system, Waters Ultrahydrogel 250, 10 mM HEPES, 75° C., 0.5 mL/min, refractive index and UV (300 nm) detection. No evidence of reaction was observed after 24 hours incubation (data not shown).

What is claimed is:

1. A purified polymeric reagent in solid form, the polymeric reagent having the structure:

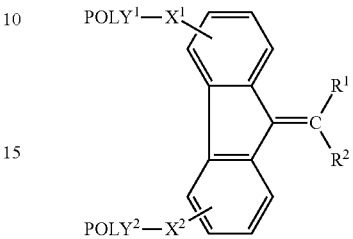

wherein:
POLY$^1$ is a poly(alkylene oxide);
POLY$^2$ is a poly(alkylene oxide);
X$^1$ is a first spacer moiety of atoms;
X$^2$ is a second spacer moiety of atoms;
R$^1$ is H or an organic radical; and
R$^2$ is H or an organic radical.

2. The purified polymeric reagent of claim 1, wherein POLY$^1$ and POLY$^2$ are the same.

3. The purified polymeric reagent of claim 1, wherein each poly(alkylene oxide) is terminally capped with an end-capping moiety selected from the group consisting hydroxy, alkoxy, substituted alkoxy, alkenoxy, substituted alkenoxy, alkynoxy, substituted alkynoxy, aryloxy and substituted aryloxy.

4. The purified polymeric reagent of claim 3, wherein each poly(alkylene oxide) is terminally capped with methoxy.

5. The purified polymeric reagent of claim 1, wherein each poly(alkylene oxide) has a weight-average molecular weight in the range of from about 120 Daltons to about 6,000 Daltons.

6. The purified polymeric reagent of claim 1, wherein each poly(alkylene oxide) has a weight-average molecular weight in the range of from about 6,000 Daltons to about 100,000 Daltons.

7. The purified polymeric reagent of claim 6, wherein each poly(alkylene oxide glycol) has a weight-average molecular weight in the range of from about 10,000 Daltons to about 85,000 Daltons.

8. The purified polymeric reagent of claim 7, wherein each poly(alkylene oxide) has a weight-average molecular weight in the range of from about 20,000 Daltons to about 85,000 Daltons.

9. The purified polymeric reagent of claim 1, wherein each poly(alkylene oxide) is linear.

10. The purified polymeric reagent of claim 1, wherein each of the first spacer moiety and second spacer moiety is selected from the group consisting of —NH—C(O)—CH$_2$—, —NH—C(O)—CH$_2$—O—, —CH$_2$—C(O)—NH—, and O—CH$_2$—C(O)—NH—.

* * * * *